(12) United States Patent
Szydlowski et al.

(10) Patent No.: US 9,023,410 B2
(45) Date of Patent: *May 5, 2015

(54) METHOD AND SYSTEM FOR RECOVERING AND PREPARING GLACIAL WATER

(71) Applicants: Allen Szydlowski, Santiago (CL); Ian Szydlowski, New York, NY (US); Juan Carlos Szydlowski, Santiago (CL)

(72) Inventors: Allen Szydlowski, Santiago (CL); Ian Szydlowski, New York, NY (US); Juan Carlos Szydlowski, Santiago (CL)

( * ) Notice: Subject to any disclaimer, the term of this patent is extended or adjusted under 35 U.S.C. 154(b) by 0 days.

This patent is subject to a terminal disclaimer.

(21) Appl. No.: 14/271,233

(22) Filed: May 6, 2014

(65) Prior Publication Data

US 2014/0237951 A1    Aug. 28, 2014

Related U.S. Application Data

(60) Continuation-in-part of application No. 13/647,255, filed on Oct. 8, 2012, now Pat. No. 8,715,756, which is a continuation of application No. 13/213,818, filed on Aug. 19, 2011, now Pat. No. 8,282,972, which is a division of application No. 11/551,125, filed on Oct. 19, 2006, now Pat. No. 8,007,845, which is a continuation-in-part of application No. 14/023,331, filed on Sep. 10, 2013, which is a continuation-in-part of application No. 13/222,940, filed on Aug. 31, 2011, now abandoned, which is a continuation-in-part of application No. 14/047,663, filed on Oct. 7, 2013, which is a continuation-in-part of application No. 13/767,675, filed on Feb. 14, 2013, now Pat. No. 8,702,460, which is a continuation of application No. 13/025,796, filed on Feb. 11, 2011, now Pat. No. 8,403,718.

(60) Provisional application No. 60/728,956, filed on Oct. 21, 2005, provisional application No. 61/378,811, filed on Aug. 31, 2010, provisional application No. 61/303,519, filed on Feb. 11, 2010.

(51) Int. Cl.
*A23L 2/00* (2006.01)
*B65B 3/06* (2006.01)
*C12G 1/00* (2006.01)
*C12C 5/00* (2006.01)
*G01N 33/18* (2006.01)

(52) U.S. Cl.
CPC ... *B65B 3/06* (2013.01); *A23L 2/00* (2013.01); *C12G 1/00* (2013.01); *C12C 5/002* (2013.01); *G01N 2033/1873* (2013.01); *G01N 33/18* (2013.01)

(58) Field of Classification Search
USPC .......................................... 426/66, 106, 397
See application file for complete search history.

(56) References Cited

FOREIGN PATENT DOCUMENTS

WO   WO 00/39408   *  7/2000   ............... E03B 3/30

* cited by examiner

*Primary Examiner* — Rena L Dye
*Assistant Examiner* — Chaim Smith
(74) *Attorney, Agent, or Firm* — Sheridan Ross P.C.

(57) ABSTRACT

Methods and systems for grouping, recovering, and processing ice and water derived therefrom obtained from an ice source, i.e., a glacier, ice sheet, ice cap, etc., are described herein, and in particular, the conveyance thereof in a non-rigid, water-impermeable device, to facilitate water derived from the ice, having specific characteristics, to be traded, stored, conveyed, or transported according to its specific characteristics.

17 Claims, 37 Drawing Sheets

|   |   |   |   |
|---|---|---|---|
| C | C | C | C |
| C | R | C | R |
| C | C | C | C |

FIG. 28

|   |   |   |   |   |
|---|---|---|---|---|
| ↓ 270 | C | C | C | C |
|   | A | R | C | R |
|   | C | C | C | C |

FIG. 27

| | | |
|---|---|---|
| C | C | C |
| C | R | C |
| C | C / R | C |
| C | R | C |
| C | C | C |

FIG. 29

METHOD AND SYSTEM FOR RECOVERING AND PREPARING GLACIAL WATER

CROSS REFERENCE TO RELATED APPLICATIONS

This application is a Continuation-in-Part Application of and claims the benefit of priority from U.S. patent application Ser. No. 13/647,255 filed on Oct. 8, 2012, which is a Continuation Application of U.S. patent application Ser. No. 13/213,818 filed on Aug. 19, 2011, now U.S. Pat. No. 8,282,972, which is a Divisional Application of U.S. patent application Ser. No. 11/551,125 filed on Oct. 19, 2006, now U.S. Pat. No. 8,007,845, which is a Non-Provisional of U.S. Patent Application Ser. No. 60/728,956 filed on Oct. 21, 2005, the entire disclosures of which are hereby incorporated by reference in their entireties. This application is a Continuation-in-Part Application of and claims the benefit of priority from U.S. patent application Ser. No. 14/023,331 filed Sep. 10, 2013, which is a Continuation-in-Part Application of U.S. patent application Ser. No. 13/222,940 filed Aug. 31, 2011, which claims priority from U.S. Provisional Patent Application Ser. No. 61/378,811, filed Aug. 31, 2010, entitled "Method and System for Trading Water"; the entire disclosures of which are hereby expressly incorporated by reference in their entireties. This application is a Continuation-in-Part Application of and claims the benefit of priority from U.S. patent application Ser. No. 14/047,663 filed Oct. 7, 2013, which is a Continuation-in-Part Application of U.S. patent application Ser. No. 13/767,675 filed Feb. 14, 2013, now U.S. Pat. No. 8,702,460, which is a Continuation Application of and claims the benefit of priority from U.S. patent application Ser. No. 13/025,796 filed on Feb. 11, 2011, now U.S. Pat. No. 8,403,718, which claims priority from U.S. Provisional Patent Application Ser. No. 61/303,519 filed on Feb. 11, 2010, entitled "Method and System for a Towed Vessel Suitable for Transporting Liquids," the entire disclosures of which are hereby expressly incorporated herein by reference in their entireties.

FIELD OF THE INVENTION

The present invention relates to a method and system for preparing drinking water from an ice sheet or glacial body. Specifically, the present invention provides a way to categorize and group ice or water contained in an ice source, then convey ice or water in standard shipping containers on ships, vessels, oil tanker transport ships, barges, boats, trains, trucks, and other modes of transportation, and finally prepare water derived from the categorized and grouped ice to be consumed as a beverage having unique characteristics and properties.

BACKGROUND

It has been known for many years to utilize, e.g., Greenland inland ice as a drinking water resource within the field of refreshing drinks or soft drinks based on the recognition that upon melting, the inland ice may be distributed to consumers as some of the purest naturally occurring water in the world. However, known methods have been disadvantageous, because some of the natural purity of the ice has been lost in the preparation of the ice as drinking water, after ice has been taken out from its natural occurrence, such as an iceberg. It has been necessary to melt the ice and then bottle or pack the water in containers permitting transport and distribution of the water to consumers.

This type of processing has been applicable not only to inland ice as can be found in Greenland, but is also useful in harvesting water from a glacier. Inland ice and glaciers are formed by yearly snowfall. Snowfall accumulates and compresses in an ice shelves over the course of many years to depths reaching over 4,000 meters in some areas. As the ice layers are compressed, and in the course of thousands of years, the ice moves towards ice rims and glaciers or other terminal points of the ice shelves. The glaciers calve and at short intervals yield an iceberg, which floats out to sea. These icebergs have typically been "caught" shortly thereafter before they are decomposed into undrinkable seawater. The ice is processed for the production of drinking water of a very high purity.

Glacial ice advances then retreats from year to year depending upon the climate around the glacier and typical snow accumulation. Glacier movements and shape shifting occur over very long periods of time (i.e., hundreds to thousands of years), but within historic memory such transformations in fewer than 100 years are not known. Presently, about 10 percent of the land in the world is covered with glaciers or ice shelves. Glaciers, ice shelves, ice caps and ice sheets store approximately 75 percent of the world's fresh water supply and cover over 15 million square kilometers. These frozen bodies of water have existed, as mentioned above, for thousands upon thousands of years. In Washington State alone, glaciers provide 470 billion of gallons of water each summer to consumers. Most of this water is used for drinking and the like. Furthermore, the Antarctic ice sheet has an age of over 40 million years.

There are several known techniques to determine the age of glaciers and ice sheets. Most of these methods employ drilling an ice core from the glacier or ice sheet then counting the layers inside of the ice core, much like counting rings in a tree to determine the age of a tree. A first method of dating ice cores consists of counting the annual layers. The basis of this method lies with looking for items that vary with the seasons in a consistent manner. Of these are items that depend on the temperature (colder in the winter and warmer in the summer) and solar irradiance (less irradiance in the winter and more in the summer). Once such markers of seasonal variations are found, they can be used to find the number of years that the ice core has accumulated over. Of the temperature dependent markers, the most important is the ratio of 180 to 160. The water molecules composed of H2 (180) evaporate less rapidly and condense more readily than water molecules composed of H2 (160). Thus, water evaporating from the ocean starts off as H2 (180) poor. As the water vapor travels towards the poles, it becomes increasingly poorer in H2 (180), since the heavier molecules tend to precipitate out first. This depletion is a temperature driven process, so the precipitation becomes more enriched with H2 (160), then is the case in the summer. Thus, each annual layer starts 180 rich, becomes 180 poor and ends up 180 rich.

A second method of dating ice cores is to use the age of previously determined markers to determine the age of various points in the ice core. This relies on accurately previously dated ice cores with accurately placed markers on them as a point of reference to determine the age of another ice core. Alternatively, this method can compare certain inclusions in an ice core with inclusions of another ice core that has been dated. Typically, inclusions are ash from volcanic eruptions and acidic layers from various weather anomalies. There exist many other known methods of dating ice cores taken from a glacier or ice sheet. Furthermore, gases collected that were trapped inside of a layer of a given ice core can be dated using standard carbon 14 and/or chlorine 36 dating. The point is that there exist many known methods to date an ice core and thus date various layers in a glacier.

SUMMARY

It is one aspect of the present invention to date such glaciers and identify the age of various layers within a glacier or ice sheet. After various layers of the glacier or ice sheet have been dated, the glacier can be mined/tapped according to known processes. The glacier ice can be recovered and segmented into various layers. Each layer corresponds to a different, now determined, age. For example, a first layer may be 100 years old whereas a second layer may be 2000 years old. Once the layers are separated according to date, each dated layer of ice can be processed for consumption as drinking water or for some other type of beverage (e.g., soda, juice, spirits, beer, wine, etc.) Consumers will readily appreciate the advantage of drinking water that existed during the time of Shakespeare, King Arthur, or Jesus, for example.

Another aspect of the present invention relates to the appreciation of how to obtain (without sophisticated chemical analysis and re-creation of waters having certain qualities and lack of pollutants, etc.), water of a very specific time period and/or geographic region. It is therefore part of the present invention that the inventor recognized the problem, which then lead to the solution. The ability to obtain water having particularly desirous aspects (whether that be an absence of present day pollutants, many of which are man made), or the presence of certain natural organic elements (i.e., perhaps pollen of plants that may now be extinct, etc.) by its nature constitutes a new process and product. Similar to the patentability derived from the "purity" of the final product, it is believed that the present inventor is the first to appreciate how to arrive at the substantially pure aspect of water derived from previously frozen ice that is over hundreds, if not thousands, if not millions of years old. Furthermore the ability to date these layers of frozen ice and generally correspond it to a given time era is also advantageous in that different properties of water corresponding to different layers may exist. While it is acknowledged that ice has been melted to derive water in the past, it has not been accomplished under conditions that preserve the pristine aspects of such water and categorize those aspects according to their date.

In accordance with embodiments of the present invention, the ice from a glacier and/or ice sheet can be cut, drilled, and/or divided into various segments. The cutting, drilling, and/or division of the segments can separate the ice into either vertically or horizontally separated segments. The segments can then be further divided by date into other segments. These dated segments are then processed under strict hygienic conditions such that the properties of the water are maintained and not polluted. In a preferred embodiment, the processing of the ice is performed under an increased atmospheric pressure and where staff must be present during the operations. The staff should wear special clothing adapted to the purpose of maintaining the hygienic properties of the water. Preferably the cutting, drilling, and/or tapping and subsequent packaging of the ice are performed in accordance with FDA current good manufacturing practice for processing and bottling of bottled drinking water, 21 CFR 129.

The ice can be drilled from the top or may be extracted from the terminus of the glacier such that the layers are taken out directly without an intermediate step as required by the vertical recovery of the ice. Furthermore, various layers of the ice can be tapped and pumped in an effort to recover the water contained therein. It is one aspect of the present invention to provide a method of processing ice from a glacier or ice sheet.

The ice is extracted from the reservoir, i.e., glacier or ice sheet. The ice is then segmented and categorized by date. Thereafter, each segmented section of ice is processed separately under hygienic conditions such that the pristine aspects of the water are maintained. The water is then packaged separately and labeled according to the date from which the ice existed. For example, renaissance water that came from the early 1400 AD era is bottled separate from water that existed at the time of Christ or around 0 BC. The water may be portioned into consumable units or into larger bulk quantities. Consumable units are generally portion sizes acquired by an individual consumer. Units ranging between 0.1 liters and 10 gallons can be partitioned. More preferably, 1.5 liter to 10 liters could be the partition size of the water. Generally, the water is partitioned into individual sellable units, preferably around one-half liter to one liter, due to the categorization of the ice and subsequent processing of the ice into water comprising different properties from one batch to the next. The inventive process merits a higher selling price of water than simply cutting up ice from a glacier and melting it. Consumers may be willing to pay a premium for water that traces its roots back to the same time that Leonardo da Vinci lived, for example. Therefore, reasonable sizing of the sellable units would be desired based on the attractiveness of the process provided by the present invention.

Alternatively, water from a particular era or containing certain properties could be sold in bulk quantities. Particularly, breweries or distilleries that have a long historic tradition could purchase large batches of dated water. They could then use water that dates back to their original product in order to recreate the original beverage that they used to produce. Many breweries and the like pride themselves on not changing certain recipes over the course of many years. Some breweries and distilleries have been creating the same product for over a hundred years. These companies would be able to purchase water that existed during the days of their founders and could create, market, and sell the "original" product to consumers with literally no changes from the true original. Consumers would be willing to pay a premium for a truly original pint of Guinness® or a bottle of Lagavulin scotch made from water dating back to 1816.

Another aspect of the present invention provides a system for categorizing, extracting, processing and packaging water into different historically categorized groups. In accordance with one embodiment, a recovery station is set on or near an ice source (e.g., glacier, ice sheet, ice cap, and the like). Also included is a recovery member that is operable to transmit ice from the ice source to the recovery station. In the recovery station, the ice can then be separated and categorized according to date and processed according to the methods described above.

A further aspect of the present invention provides a method for producing bottled water from glacial ice having a predetermined age. The method includes analyzing the age of a number of layers of glacial ice within an ice source. Then a first layer, whose age is known, is extracted in either a solid or liquid state. The first layer is extracted such that other layers remain substantially undisturbed. This allows the first layer to be substantially separated from the other layers of glacial ice, thereby isolating the characteristics of the water within the first layer. After the water has been extracted it is collected and directed into a container (e.g., a bottle, bag, or the like.) Once the water from the first layer has been effectively bottled or contained, an indication in the form of a tag or label is place on or around the bottle/container to reflect the characteristics of the water that is within the bottle/container.

Still a further aspect of the present invention provides for a way of recovering and preparing dated water in an economically viable fashion. In one embodiment, a number of containers are separated and filled with water (either from the ice source itself or from another source) in a frozen or liquid state. Water from various segments of the ice source are then extracted from the ice source and then placed into different containers. Essentially, a majority of the water in each container does not need to be extracted according to the costly process described herein. However, a non-trivial amount of categorized water is also in each container such that consumers can be assured that the water they are drinking is at least partially derived from a particular time period and thus has the unique characteristics of water from that time period. The primary water that is used (i.e., the non-categorized water) should be held to the highest purity standards so that when the categorized water is added, the unique characteristics of that water are not lost or disrupted.

It is an object of the present invention to provide an at least partially submersible, towed vessel capable of transporting volumes of fluent cargos, such as potable water, juice, wine, and/or various other fluids suitable for human use and consumption. The towable vessel may be a very large bag ("VLB"), preferably having one or more of the following characteristics: solar power and/or wind power capabilities integrally associated with the fluid containing vessel; a drone manipulated steering system; operatively associated fluid segregation systems; and buoyancy controls and/or air venting systems.

It is yet another object of the present invention to provide a device suitable for containing large volumes of fluent cargos that is further capable of being towed by various watercrafts.

It is yet another object of the present invention to provide a towed fluid containing vessel further comprising means to facilitate the rapid filling and emptying of fluids to be contained within. In one embodiment, the present invention comprises a plurality of ports through which a liquid and/or air/gas are conveyed to facilitate the rapid emptying and/or filling of such devices.

In one embodiment, after most of the water has been drained from the VLB, the VLB is towed back to its point of origin (or to another water source) with only a small amount of water remaining in the bag. Accordingly, the mostly-empty VLB is towed behind a vessel like a noodle because the mostly-empty VLB is slightly buoyant with only a small amount of water in the bag. In some embodiments, the VLB is not rolled up and put on a ship to ship it back to its point of origin because rolling up the VLB would damage the material of the bag. In additional embodiments, the substantially-empty bag may be attached to a buoyancy device for its return voyage.

It is yet another object of the present invention to provide a water-towed vessel further comprising means for signaling a physical position of the vessel. For example, means may be provided to signal to other vessels or individuals the presence and location of the vessel. In one embodiment, lighting means and beacons are disposed on a dorsal portion of a vessel to indicate the presence of the vessel to nearby persons and other vessels. Additional devices, such as nets, buoys, and gated systems, for example, may be deployed around a perimeter of the device to alert various individuals and vessels of the presence of the vessel and/or a vessel's sub-surface presence. U.S. Pat. No. 5,197,912 to Lengefeld discloses a buoy for attachment to the net line of a fishing net and is hereby incorporated by reference in its entirety. Devices disclosed in Lengefeld and those similar may be employed in various features and embodiments of the present invention. For example, a ring or net with marker buoys useful for keeping the ring/net afloat and simultaneously serving as a visual indicator may be employed.

Additionally, means may be provided in association with the vessel to convey information to users or devices at various locations throughout the world regarding the coordinates or relative position of the towed vessel, such as through global positioning systems ("GPS") and other similar devices. Thus, in one embodiment, the present invention comprises light-emitting devices for signaling a position of the device as well as at least one GPS transmitter for broadcasting/transmitting a location of the device.

In an alternative embodiment, devices of the present invention comprise at least one GPS transmission device, which is in communication with a network or database that is further accessible by various additional devices. Additional devices of the present invention may include, for example, computer terminals, handheld devices, and a variety of other devices capable of receiving GPS information. Thus, embodiments of the present invention may be tracked by any number of individuals or systems throughout the world.

It is yet another object of the present invention to provide means for ease of storage and/or transportation of the towed vessel when not in use for transporting fluent cargos. Such means may include, for example, the ability to fold, roll, or compress the present invention for ease of storage and/or transportation when towing is not desired or needed. In an alternative embodiment, the present invention comprises variable buoyancy control, which allows for the adjustment of buoyancy at one or more locations of the device. For example, when a device of the present invention is empty, one longitudinal end of the device may be deprived of buoyancy, while an opposing longitudinal end is allowed to remain buoyant, thus allowing the elongate shape to be positioned in a generally vertical position. In this manner, the device is capable of occupying less area at the surface of a body of water.

The VLB may include sensors to detect the integrity of the bag, stresses on the bag, the velocity of the bag, wave conditions, wave velocity, temperature, etc. These sensors may include strain gauges. For example, integrated sensors and a fiber-optic grid may monitor any deformations in the bag during the bag's voyage across the sea. All of this data may be input into the software to further calculate the most economical route presently or in the future. Further, these data points may affect whether the route of the bag is changed mid-course. Additionally, if the integrity of the bag is compromised, the VLB may have an emptying mechanism to quickly empty the bag in case of emergency. Sensors and software may also be used to calculate the current fuel consumption rate. Additionally, the sensors may calculate the yaw, roll, and pitch of the VLB. Ideally, the VLB will not yaw because this would increase drag and decrease efficiency.

The VLB may be towed at different speeds depending on whether it is being towed by a tug boat or an oil tanker. The software may take the towing boat type and characteristics into account when calculating efficiencies.

In one embodiment, the VLBs are towed by large ocean liners, oil tankers, or supertankers. These large ships may be 30-90 meters deep, and thus may be required to stay in deep waters. If this is the case, then small boats or tugs may travel from land to the VLB secured to the large ship to get water from the VLB. Then the small vessel may return to land with the water or other liquid from the VLB.

In some embodiments, the VLB may be shaped like the flexible containment vessels described in U.S. Pat. No. 7,775,171 to Tupil and U.S. Pat. No. 5,657,714 to Hsia et al., which are incorporated by reference herein in their entireties. In one embodiment, the VLB may have specifications similar to the flexible containment vessels described in Canadian Patent Application No. CA 2,744,617, which is incorporated by reference herein in its entirety. VLBs can be employed in a variety of water quality trading systems and methods such as those described in U.S. Pat. No. 7,062,406 to Patwarahan, which is incorporated herein by reference in its entirety.

One embodiment of the present invention is a method of preparing water from an ice source, the method comprising: (a) selecting a water source comprising water in the form of ice, wherein the water has at least one desirable characteristic; (b) conducting water from the ice source through a plurality of filtration stages, wherein at least one of the plurality of filtration stages comprises clay; (c) identifying at least three characteristics in the water.

In one embodiment, the ice comprises at least 1000 cubic meters (m3). In various embodiments, the ice is selected from the group consisting of an ice cap, a glacier, and an iceberg. In one embodiment, the desirable characteristic is that the ice is substantially free of at least one material selected from the group consisting of nitrate, nitrite, mercury, lead, arsenic, cadmium, benzene, chlorine, chromium, tetrachloroethylene, trichloroethylene, uranium, 2,4-Dichlorophenoxyacetic Acid (2,4-D), dichlorobenzene, polychlorinated biphenyls (PCBs), trihalomethanes (THMs), volatile organic compounds (VOCs), lanthanoids, actinides, and pesticides. In yet another embodiment, the ice is substantially free of at least three of such materials. In various embodiments of the present invention, the characteristics in the water are selected from the group consisting of: geographic location, geological period, quality, source, purity, geological formation, treatment regimen, latitudinal characteristics, mineral content, extraterritorial content, and extraterrestrial content. In a particular embodiment, the water from the ice source comprises a quantity of glycine.

In one embodiment, one or more filters are employed to filter the water; such filters comprise a permeability value between approximately 10-10 cm/s and approximately 10-3 cm/s. In one embodiment, the water has at least one characteristic similar to at least one characteristic of water derived from a sub-polar ice field located approximately between 15 and 60 degrees south latitude. In various embodiments, the characteristics include at least one of the characteristics selected from the group consisting of: purity, mineral content, pH, and acidity, e.g., as more specifically found in water obtained from World's Fresh Waters off of the coast of southern Chile. In one embodiment, the source is evaluated to: identify that the source has a total volume of at least 10,000 cubic meters. In a further embodiment, the source is evaluated to determine the presence of glycine in at least a portion of the source. In a particular embodiment, the water is directed through a filter comprising clay. Such a step is referred to as a filtration stage. In a further embodiment, the water is filtered using primarily gravitational energy. In one embodiment, the water is filtered using only gravitational energy. In yet another embodiment, the one or more filters consist essentially of clay and in others, a sand/clay combination. In a further embodiment, the water is packaged for distribution in large material bags, e.g., plastic or fabric bags of at least 8×8×20 ft. in dimension.

The various embodiments of the present invention also disclose methods of trading water having particular characteristics. Thus, in one embodiment, a method for trading water is provided, the method generally comprising: (a) connecting a first entity desiring to obtain water having at least one specific characteristic with a second entity having possession of a source of water comprising the at least one specific characteristic; (b) conveying from the first entity to the second entity information relating to the quantity and characteristic of the desired water; (c) based on the information conveyed, transferring at least one right to a quantity of water having the desired specific characteristic that the second entity is willing to transfer, from the second entity to the first entity, wherein the second entity receives compensation in an amount related to the quantity of water covered by the transferred at least one right.

Water of various embodiments of the present invention has at least one specific characteristic. In one embodiment, the specific characteristic is selected from the group consisting of pH, acidity, geographic location, geological period, quality, source, purity, geological formation, treatment regimen, latitudinal characteristics, mineral content, and extraterrestrial content. In one embodiment, the water is substantially free of contaminants. In various embodiments, such contaminants are selected from the group consisting of heavy metals, including transition metals, metalloids, lanthanoids, and actinides (e.g. Mercury, Lead, Chromium, etc.), uranium, arsenic, chlorine, cadmium, benzene, chlorine, tetrachloroethylene, trichloroethylene, 2,4-Dichlorophenoxyacetic Acid (2,4-D), dichlorobenzene trihalomethanes (THM's), uranium, PCBs (polychlorinated biphenyls), nitrate, nitrite, pesticides, herbicides, volatile organic compounds (VOCs), carbon emissions from coal and petroleum fired power plants, and harmful microorganisms such as coliform bacteria, giardia, and cryptosporidium.

In various embodiments, the entities can be individuals or groups of individuals such as corporations, partnerships, agencies, non-profit agencies, and the like, or combinations thereof.

Any means of connection that allows communication between the entities can be used to practice various embodiments of the present invention. In one embodiment, the connection is formed using at least one electronic device. In various embodiments, the at least one electronic devices includes, but is not limited to, a data transmission device, a telephone, a cellular phone, a facsimile machine, and a computer. In one embodiment, the connection is formed through an exchange. In a particular embodiment, the exchange is located within a single structure. In one embodiment, the exchange is connected to more than one individual structure.

According to embodiments of the present invention, various rights in water of the present disclosure can be transferred between entities. In one embodiment, the right is an option to obtain title to an amount of water. In one embodiment, the right is the right to use an amount of water as an asset. In yet another embodiment, the right is title to an amount of water. In a further embodiment, the method comprises transferring physical possession of the water to an entity other than the second entity.

One of skill in the art will recognize that storage, as well as transport, of commodities is an important and necessary feature of trading systems. Thus one embodiment of the present invention is a method of delivering non-saltwater to a destination using oil tankers. Such tankers can be oil tankers or liquid natural gas (LNG) tankers. Such embodiments are generally practiced by: a) providing a tanker with cargo at a first location and having a second location as a destination port for delivery of the cargo, wherein said cargo is delivered at said destination port such that the tanker is emptied, except for residual cargo residue left behind; b) substantially filling the tanker with non-salt water in both a ballast section of the tanker and in a second section of the tanker that previously held cargo for transport; c) at least partially treating said non-salt water contained in said tanker while en route to said second destination, said water treatment selected from the group consisting of at least two of the following: i) treating the water; and ii) segregating water treated in accordance with step i) from water that has not been treated in accordance with step i).

In one embodiment the tanker is an oil tanker. In another embodiment, the tanker is a LNG tanker. In one embodiment the cargo is oil. In another embodiment, the cargo is natural gas.

In various embodiments, the treatment step comprises at least one method selected from the group consisting of filtration through a natural clay filter, centrifugation, reverse osmosis, gravity separation, contact with a natural coagulant, adjusting pH to between about 6 to about 11, ultraviolet ("UV") irradiation, and ozonation. In one embodiment, the step of segregation is accomplished by at least one of: conveying said water treated in accordance with step i) to a substantially cargo-free storage section of the oil tanker; and conveyance of said water treated in accordance with step i) to a very large bag adapted for containing water. In a further embodiment, the water is further treated upon arrival at the second location.

One embodiment of the present invention comprises a method of delivering non-salt water to a destination, the method comprising: (a) selecting a water source comprising non-salt water, wherein the water has at least one desirable characteristic; (b) providing a rigid shipping container and a flexible liquid containment container, wherein the flexible liquid containment container is sized to fit in the rigid shipping container and the liquid containment container comprises one or more ports for the intake and exhaust of the water; (c) filling the liquid containment container at least half full with the water; (d) placing the liquid containment container in the shipping container; and (e) transporting the shipping container and liquid containment container from a first location to a second location. In some embodiments, the method further comprises storing the water in a non-rigid, water-impermeable device with an elongate shape having a first end, a second end, and a generally planar and streamlined shape in plain view, and a plurality of ports for the intake and exhaust of fluids.

One embodiment of the present invention is a method for trading water comprising: connecting a first entity desiring to obtain water having at least one specific characteristic with a second entity having possession of a source of water comprising the at least one specific characteristic; conveying from the first entity to the second entity information relating to the amount and characteristic of the desired water; based on the information conveyed, transferring a right to an amount of water having the desired specific characteristic that the second entity is willing to transfer from the second entity to the first entity, wherein the second entity receives compensation in an amount related to the amount of water covered by the transferred right; conveying the water from a first location to a second location in at least one flexible liquid containment container, wherein the at least one liquid containment container comprises one or more ports for the intake and exhaust of the water; conveying the least one flexible liquid containment container with the water in at least one shipping container, wherein the at least one flexible liquid containment container is sized to fit in the shipping container; and transferring physical possession of the water to the first entity; wherein the water possessed by the second entity had been within 24 months of conveying the water sequestered as ice.

In a further embodiment, the at least one shipping container with the flexible liquid containment container with the water comprises an associated signal transmitter having a unique, embedded identification code and is operative to periodically transmit a signal containing data corresponding to the unique identification code. Thus, every shipping container may have an ID tag showing the owner, category of the container, a serial number, and a check digit. Once all of the shipping containers are loaded onto the boat, a system may be used to locate each container by bay, row, and tier.

Another embodiment of the present invention is a method for trading water comprising: connecting a first entity desiring to obtain water having at least one specific characteristic with a second entity having possession of a source of water comprising the at least one specific characteristic; conveying from the first entity to the second entity information relating to the amount and characteristic of the desired water; based on the information conveyed, transferring a right to an amount of water having the desired specific characteristic that the second entity is willing to transfer from the second entity to the first entity, wherein the second entity receives compensation in an amount related to the amount of water covered by the transferred right; determining a cost competitive time to convey the water and a cost competitive quantity of the water to convey; conveying the cost competitive quantity of the water from a first location to a second location at the cost competitive time, wherein the water is conveyed in at least one shipping container, wherein the water is contained within at least one flexible liquid containment container sized to fit in the shipping container and substantially fill the at least one shipping container, and wherein the at least one liquid containment container comprises one or more ports for the intake and exhaust of the water; and transferring physical possession of the water to the first entity.

One embodiment of the present invention is a method of trading water comprising: (a) connecting a first entity desiring to obtain water having at least one specific characteristic with a second entity having possession of a source of water comprising the at least one specific characteristic; (b) providing a plurality of shipping containers, the shipping containers comprising one or more flexible liquid containment containers at least half full of the water, wherein the water has an average temperature of less than approximately 10 degrees Celsius, and wherein the flexible liquid containment containers fit in the shipping containers; (c) placing the plurality of shipping containers on a transport vessel; (d) creating a refrigeration environment comprising: (i) a refrigeration area; (ii) at least one cold water shipping container on a first long side of the refrigeration area; (iii) at least one cold water shipping container on a second long side of the refrigeration area; and (iv) at least one cold water shipping container on a short side of the refrigeration area; (e) conveying the water from a first location to a second location; and (f) transferring physical possession of the water to the first entity.

It is one aspect of embodiments of the present invention to provide a method and system of transporting water in bags on various modes of transportation (e.g., ships, trains, and tractor trailer trucks). In some embodiments, the bags of water are transported in shipping containers. In one embodiment the shipping container with the bag of water can be loaded onto a ship and transported, then unloaded from the ship and loaded onto a train to be transported by train, then unloaded from the train and loaded onto a tractor trailer truck (also known as a "semi" or an "18-wheeler") to be transported by truck to the water's final location. Shipping water in large bags allows for higher payloads per container than more traditional means of liquid transport, e.g., bottled, IBCs, and 44 gallon drums.

In another embodiment, the shipping containers may comprise a liner system, such as the system described in European Patent Application No. 0538563 to Stopper, or the liner described in U.S. Pat. No. 5,487,485, both of which are incorporated by reference herein in their entireties.

In various embodiments, the water is transported in a bag in the shipping container. The bag may be sized such that it fits within the specific shipping container used. For example, a 20-foot long bag may be used in a 20-foot long shipping container. In one embodiment the bag is similar in characteristics to the flexitanks made Full-Pak. In other embodiments, the bag may have similar qualities to the large bag of water towed by a ship and described herein. Thus the bag may be manufactured of a similar material to the towed bag. In some embodiments, the shipping container may also be lined with a liner to protect the bag of water. The installation of liners is fast and easy.

While tanks have been around since the 1980s, improvements to their construction and the plastic membranes used have reduced the risk of spoilage, according to the Waste and Resources Action Programme, a U.K. government-backed packaging body. That makes long-distance bulk shipments as viable as the short-range tanker exports common between European countries. High quality water bags offer an excellent alternative for transportation to remote areas with reduced shipping costs. Additionally, the bags allow for minimal oxygen contact to ensure the water oxidization is kept to an optimum amount.

In one embodiment, upon arriving at the water's final destination, the shipping container with the bag of water is unloaded. The bag and container may then be placed in a location where people can retrieve the water from the bag. In an alternate embodiment, only the water bag (not container) is unloaded and placed such that people may retrieve the water from the bag.

It is another aspect of embodiments of the present invention to provide a civil defense system and method of providing cities, schools, office buildings, homes and/or other building with a replenishable container of fresh water. Thus, each building or home may have its own shipping container-sized bag of water. This aspect of embodiments of the present invention would address the long felt but unsolved issues with respect to the control of fresh water sources in times of emergency or strife (e.g., terrorist poisoning of municipal water supplies). In other words, embodiments of the present invention provide a system where fresh water would be so distributed that it would be impossible for a terrorist or enemy to deprive an entire populace from its fresh water reserves. Thus, embodiments of the present invention may provide comfort and/or safety. Accordingly, the buildings and homes with water bags will have security in their water sources and may even be able to distribute water so that there is not a terrorist threat to a city or town's main water source. In some embodiments, the bag may be stored in the shipping container or may be stored without the shipping container. Further, the bag may be stored in the building's basement or somewhere where it can be tied into the building's plumbing system. The bag may have specific valves, plumbing, and other mechanical features to allow it to be tied directly into the building's existing plumbing system. Any valves or plumbing equipment now known or later developed may be used in various embodiments. In further embodiments, gravity may facilitate the water bag's tie in to the existing plumbing system, e.g., place the water bag in the building's basement such that gravitational forces create a suction force to pull the water out of the bag. In one embodiment, the bags have a valve for dispensing the water rather than being tied into the building's plumbing system. Therefore, if there is a terrorist attack, a war strike, a battle, or an act of god that pollutes a major fresh water source, the buildings and homes with the water bags could shut off the water coming in from the municipal or other large water source and the buildings and homes could turn on the water bag system. Thus the buildings and homes with the water bags would not be deprived of fresh water.

Because the water in some embodiments is put into the bags at very cold temperatures (typically below 10° C.) and the bags of water have large masses, the water in the bags remains cold (typically below 10° C.) throughout the lifecycle of the water (i.e., until the water is removed from the bag for human consumption). In additional embodiments, the cold bags of water in shipping containers are used as large refrigerators such that fruit or other items that should be refrigerated while shipped may be placed within the shipping container with the large bag of cold water.

Refrigerated containers are typically used to transport perishable products. Ideally, the refrigerated containers are intended to maintain a substantially uniform and constant temperature throughout the interior of the container in order to efficiently refrigerate all the products and prevent spoilage. Typically, such uniform constant temperatures are not achieved with the result that there is considerable spoilage of cargo. The industry uses a range of refrigerated containers, each designed for a specific type of transportation system. For example, containers can be designed for use with trucks and truck trailers (e.g., truck-trailer reefers), sea going ships (e.g., marine reefers), or trains (e.g., rail reefers). These refrigerated containers are typically uniformly shaped rectangular boxes that are sized to be efficiently used with the intended transportation system. In one embodiment of the invention, a side wall through which air can flow vertically may include in order: an outer wall, a corrugated intermediate wall, and a replaceable planar interior panel.

It is another aspect of embodiments of the present invention to provide a refrigeration cave comprised of containers and a system and method of shipping goods using the refrigeration cave (note that the term "refrigeration environment" may be used interchangeably herein with "refrigeration cave"). In one embodiment, the refrigeration cave is comprised of shipping containers filled with bags of very cold water (approximately 10° C. or colder) and a space between the containers (the cave or environment) in which perishable items or other items requiring refrigeration may be shipped. The physical characteristic of having a very large body of cold water (less 10° C. or so) is that the water contained in the shipping containers provides an inexpensive way to create the refrigeration caves on board container ships. Thus, the items requiring refrigeration may be shipped in shipping containers positioned proximate shipping containers containing bags of very cold water. Accordingly, within such refrigeration caves—surrounded by massive, very cold water containers—one could place large containers of perishable items that require refrigeration during transport. In one embodiment, a shipping container comprising items requiring refrigeration may be completely surrounded by shipping containers comprising bags of cold water. In another embodiment, the shipping container comprising refrigerated items may be surrounded by three or more cold water shipping containers. These embodiments have the ability to employ standard containers (rather than specially configured and very expensive refrigerated containers) to ship such perishable goods because the perishable goods are placed in standard containers inside the refrigerated cave constructed from very cold water-filled containers. Using standard containers would benefit: (1) the shipping company because it could dispense with the need for the expensive refrigerated containers and just employ standard containers; (2) the manufacturers of the refrigerated products because they could vastly reduce their costs of shipping such items, courtesy of the refrigerated cave comprised of ice-cold water-containing containers; and (3) the company shipping the cold water-containing containers because it should receive reduced shipping costs for its cold water as the ice-cold containers are now supplanting the previously required refrigerated containers that were traditionally needed to ship perishable goods.

One aspect of embodiments of the refrigerated cave is providing refrigerated shipping. Thus, one embodiment may include itemizing and scheduling the shipping of perishable products requiring refrigeration, planning for water cave space, and offering discounted refrigeration rates to both parties: the cold container owner and the refrigerated product owner. One embodiment of the present invention pertains to the particulars of the scheduling of containers and the careful placement and construction of such refrigerated caves onboard a ship. It should be noted that in addition to the presumed weight and perhaps contents of a particular container as being appropriate to place on a container ship (e.g., there may be some balancing of the load and the separation of toxic chemicals from refrigerated items), shipping ice-cold water may add another factor to the shipping equation: the temperature of the container and its ability to be used as a large refrigerated cube that is able to "share" its cold emanating characteristics if properly placed and positioned on a container ship. In one embodiment, the shipping containers with cold water surround multiple containers with perishable goods and because the containers with perishable goods may share a wall, the perishable goods containers may have similar contents. Thus, toxic items may not be shipped adjacent non-toxic items. Or, items with distinct smells (e.g., durian fruit) may not be shipped adjacent to more sensitive items (e.g., berries). Further, because of the weight of the water, it may wise to not place fragile and/or very light-weight items in shipping containers beneath the containers comprising water. But, this may not be an issue in other embodiments where the shipping containers are designed such they are strong enough to hold and stack heavy containers. In one embodiment, water-sensitive items (e.g., electronics, cars, etc.) may not be shipped in shipping containers below or adjacent to shipping containers with bags of water. This will ensure the safety of the water-sensitive items if one of the bags of water were to leak.

One embodiment of the present invention is a method of trading water comprising: (a) connecting a first entity desiring to obtain water having at least one specific characteristic with a second entity having possession of a source of water comprising the at least one specific characteristic; (b) providing a plurality of shipping containers, the shipping containers comprising one or more flexible liquid containment containers at least half full of the water, wherein the water has an average temperature of less than approximately 10 degrees Celsius, and wherein the one or more flexible liquid containment containers fit in the shipping containers; (c) placing the plurality of shipping containers on a transport vessel; (d) creating a refrigeration environment comprising: (i) a refrigeration area; (ii) at least one cold water shipping container on a first long side of the refrigeration area; and (iii) at least one cold water shipping container on a second long side of the refrigeration area; and (iv) at least one cold water shipping container on a short side of the refrigeration area; (e) conveying the water from a first location to a second location; and (f) transferring physical possession of the water to the first entity.

Various embodiments may also include preparing the shipping container to be filled with a bag or water, filling the bag of water in the shipping container, and adding a gas or ice to control the cleanliness of the container or the temperature of the container.

In additional embodiments, the cold shipping containers comprise one or more flexible liquid containment containers comprising water that is approximately 10 degrees Celsius or colder, wherein the flexible liquid containment containers fit in the rigid shipping containers.

In one embodiment, a system and process for improving container flow within a port facility is provided, including improved equipment and software for controlling operation and flow of the equipment in the part facility. The system may include a port facility geographically arranged to separate land operations and water operations. Systems and processes are described in U.S. Pat. No. 8,306,649 to Buzzoni et al., which is incorporated by reference herein in its entirety.

One embodiment of the present invention comprises a container to receive a parcel for shipment to an intended recipient comprises a pouch having a pouch interior and a mouth, a closure movable between open and closed positions, and a protective insert structure removably disposed in the pouch interior to substantially envelop the parcel and reduce risk of damage to it during shipment. In another embodiment, the container comprises a container body, a closure and an air bladder disposed in the container body for receiving and substantially enveloping the items to reduce damage thereto during shipment. Methodologies are also provided for shipping a parcel from a shipper located at an origin address location to an intended recipient located at a destination address location, such as those disclosed in PCT Patent Application No. WO 2003/104089 to Dickinson, which is incorporated by reference herein in its entirety.

In additional or alternative embodiments of loading and unloading ISO containers from container ships at seaports, the system or method comprises a vertical support which is propped up on the land side and on which a horizontal extension arm is braced. Similar methods are disclosed in U.S. Pat. No. 7,410,339 to Franzen et al., which is incorporated by reference herein in its entirety. Further, a terminal or system for the automatic computerized unloading of containerized cargo from container ships to trucks, railroad cars, other ships and storage is provided. The terminal system is equipped to store or transfer unloaded cargo automatically by using independent container transfer vehicles. The cargo ships are moored between quays of a terminal building constructed in or adjacent to a waterway as disclosed in U.S. Pat. No. 6,802,684 to Arntzen et al., which is incorporated by reference herein in its entirety. In one embodiment, the shipping containers are unloaded from and loaded onto a marine vessel and a land vessel, or vice versa, as disclosed in U.S. Pat. No. 6,902,368 to Hagenzieker et al., which is incorporated by reference herein in its entirety. In further embodiments, the shipping container may be transferred from a rail car to a ship or vice versa and an intermodal interface may be used, such as the one described in U.S. Pat. No. 5,505,585 to Hubbard, which is incorporated by reference herein in its entirety. Other modular intelligent assist systems may also be employed, such as the systems described in U.S. Pat. No. 6,928,336 to Peshkin et al., which is incorporated by reference herein in its entirety In some embodiments, software may be used to efficiently load shipping containers onto a boat and place various shipping containers about the boat. One such software tool is CargoWiz, which is incorporated by reference herein. Additionally, algorithms and computer systems may be used to help plan the most efficient and practical storage scheme so ships can get in and out of port quickly. In some embodiments, the type of shipping container affects its location on the ship. For example, refrigerated containers must be placed near a power source. In further embodiments, the cargo within a shipping container affects the container's location on the ship. Or, if containers comprising very cold water are onboard the ship, the container needing refrigeration (e.g., a container with perishable goods) may be surrounded by such containers comprising very cold water. In other embodiments, cargo needing to remain hot may be placed by other cargo that needs to remain hot. Thus, in various embodiments, the hot shipping containers are placed near other hot shipping containers and away from cold shipping containers. The desired temperature of the shipping container may determine where it will be placed on the ship, i.e., cold containers on one side, warm containers on another side, and neutral temperature containers in the middle. In some embodiments, for example, shipping containers comprising expensive cargo may be surrounded by containers comprising cheaper cargo to prevent against thieves. Different chemicals must also be kept apart. For example, acetylene must be separated by at least one container space or bulkhead from chlorine, and barium cyanide must be isolated from acids. Flammable cargo should be positioned away from the edge of the ship if the ship will be traveling through areas where pirates are known to use rocket-propelled grenades (e.g., the Indian Ocean) because the containers of combustible material could be ignited by these grenades. Additionally, heavy cargo should be placed lower/below lighter cargo. This prevents the stack from collapsing. Heavy versus light cargo should also be distributed as evenly as possible across the ship to keep the ship balanced.

In one embodiment of the present invention, a method loading a vessel is provided comprising: providing shipping containers with cargo to be shipped; measuring a temperature of the contents of each shipping container; entering the temperature into a computer data base; noting whether any particular shipping container is insulated—which may make the insulated shipping container unsuitable for a temperature controlling use in the stacking and placement of the shipping containers; labeling the shipping containers in a manner that permits ready identification as to a specific shipping container so the shipping container can be located and transported as desired, wherein the labeling may be a physical label on the shipping container or may be an electronic label that may be scanned, etc. and may use GPS or other identifying characteristics of the container, wherein the other identifying characteristics of the container include one or more of an owner, a color, a destination, and a size; arranging the shipping containers on the vessel in accordance with a desired refrigeration or heat objective such that shipping containers desiring refrigeration are placed proximate other shipping containers desiring refrigeration and shipping containers desiring heat are placed proximate other shipping containers desiring heat; determining the weight of the loaded shipping containers; placing heavier containers below lighters containers on the vessel; determining additional aspects of the contents of the containers, wherein the additional aspects include one or more of a toxic nature, a chemical substance, a reactivity with other adjacent containers, expense of the contents, dry or wet, and an aversion to water or other liquids; and load the shipping containers onto the vessel in a manner that maximizes the desired temperature characteristics sought to be achieved during transport.

Devices for transporting a single large volume of water or liquid in and through the Earth's waterways have been contemplated. For example, U.S. Pat. No. 6,550,410 to Reimers, which is hereby incorporated by reference in its entirety, discloses a system and method for conveying fluids, where the system is adapted for towing by marine crafts in offshore conditions. Reimers further discloses a collapsible fluid container with an elongated shape, towing, and mooring means, as well as container retrieval, storage and deployment means. Reimers, however, does not teach various novel features of many of the embodiments of the present invention, including, but not limited to, locating means, rapid filling and/or emptying means, renewable energy means, locating and tracking means, and means for preserving the purity and integrity of fluids to be housed within.

Similarly, U.S. Pat. No. 7,500,442 to Schanz, which is hereby incorporated by reference in its entirety, discloses a submerged transport and storage system for liquids and solids. Schanz discloses a towable vessel with optional air and liquid storage bladders useful for adjusting buoyancy and allowing simultaneous transport of different solids and liquids. Schanz further discloses a cord-like connecting spine passing through the hull towing attachment ends to provide longitudinal reinforcement and prevent undesired distortion of the vessel during towing. Schanz, however, fails to teach a device that may be readily transported and/or stored when not in use and a device using renewable energy resources to transport the water vessel. Furthermore, Schanz also fails to teach a device with means for locating the towed vessel.

Canadian Patent No. CA 2,744,617 to Audet discloses a flexible fluid containment vessel and is incorporated by reference herein in its entirety. U.S. Patent Pub. No. 2013/0213897 to Jauncey discloses a towable bladder and is incorporated by reference herein in its entirety.

U.S. Pat. Nos. 6,047,655 and 6,330,865 to Cran, which are hereby incorporated by reference in their entireties, disclose a flexible barge. These references disclose a system comprising a flexible barge structure with a system of straps to prevent propagation of rips and to distribute concentrated tow forces over the flexible barge. Cran fails to teach several novel aspects of the present invention.

U.S. Patent Publication No. 2012/0024215 to Flockenhagen discloses a floating hollow body and is incorporated by reference herein in its entirety. U.S. Pat. No. 6,860,218 to Eagles discloses a flexible fluid containment vessel and is incorporated by reference herein in its entirety. U.S. Pat. No. 3,955,524 to Renoux discloses a flexible marine trailer and is incorporated by reference herein in its entirety.

U.S. Pat. No. 2,391,926 to Scott, which is hereby incorporated by reference in its entirety, discloses a non-rigid barge for transporting fluids and other materials by water. Scott also discloses an upper surface or deck of the barge equipped with radio controlled lights or other means for navigational purposes. Scott, however, fails to teach a device comprising means for rapid filling and emptying of fluids and other substances, signaling or other locating means outside of those for purely navigational purposes, means for filtering and/or preserving the integrity of liquids housed within, and means for storing and transporting the towed vessel when not in use.

The VLB may include sensors to detect the integrity of the bag, stresses on the bag, the velocity of the bag, wave conditions, wave velocity, temperature, etc. These sensors may include strain gauges. For example, integrated sensors and a fiber-optic grid may monitor any deformations in the bag during the bag's voyage across the sea. All of this data may be input into the software to further calculate the most economical route presently or in the future. Further, these data points may affect whether the route of the bag is changed mid-course. Additionally, if the integrity of the bag is compromised, the VLB may have an emptying mechanism to quickly empty the bag in case of emergency. Sensors and software may also be used to calculate the current fuel consumption rate. Additionally, the sensors may calculate the yaw, roll, and pitch of the VLB. Ideally, the VLB will not yaw because this would increase drag and decrease efficiency.

The VLB may be towed at different speeds depending on whether it is being towed by a tug boat or an oil tanker. The software may take the towing boat type and characteristics into account when calculating efficiencies.

In one embodiment, the VLBs are towed by large ocean liners, oil tankers, or supertankers. These large ships may be 30-90 meters deep, and thus may be required to stay in deep waters. If this is the case, then small boats or tugs may travel from land to the VLB secured to the large ship to get water from the VLB. Then the small vessel may return to land with the water or other liquid from the VLB.

In some embodiments, the VLB may be shaped like the flexible containment vessels described in U.S. Pat. No. 7,775,171 to Tupil and U.S. Pat. No. 5,657,714 to Hsia et al., which are incorporated by reference herein in their entireties. In one embodiment, the VLB may have specifications similar to the flexible containment vessels described in Canadian Patent Application No. CA 2,744,617, which is incorporated by reference herein in its entirety. VLBs can be employed in a variety of water quality trading systems and methods such as those described in U.S. Pat. No. 7,062,406 to Patwarahan, which is incorporated herein by reference in its entirety.

In one embodiment of the present invention, water is transported in a large water bag. Such bags are made of a suitable material, such as plastic, rubber, nylon, combinations thereof, and the like, and can vary in size depending on the amount of water being transported. Such bags have the advantage of not altering the quantity or characteristic of the water contained therein. To transfer water using such devices, the bags are filled with the water to be transported, sealed and then transferred to the final destination. Any method of moving such bags can be employed. A particularly useful method is to tow such bags through the ocean using ships, barges, tankers, and the like. In one embodiment, unmanned, GPS-guided, boats tow the bags. Other space-based and terrestrial guidance systems may also be used to guide vessels towing such bags. In some embodiments, the vessels operate autonomously. In still other embodiments, the vessels operate autonomously but can receive updated commands and instructions from remotely located operators. Such transport mechanisms would reduce the cost associated with a crew.

It is known that when pliable vessels are used to tow or transport volumes of water, wave propagation through the body of water and/or stored volume of water can present undesirable complications. Accordingly, various embodiments of the present invention comprise wave damping features adapted to reduce such effects. For example, various devices and features described in U.S. Pat. No. 7,686,539 to Aristaghes, which is incorporated by reference herein, may be utilized with features of the present invention. For example, wave dampening structures may be disposed within water containing vessels and/or positioned around water containing vessels of the present invention.

In various embodiments, devices of the present invention comprise the ability to convert and/or utilize energy from naturally occurring resources such as solar, wind, wave, and thermal resources. In various embodiments, energy captured and/or converted from these sources may be used for various on-board functions, such as propulsion, heating, and various purification techniques. U.S. Patent Application Publication No. 2013/0217822 to Hopper discloses power generation by changing density of a fluid and is incorporated by reference herein in its entirety.

In one embodiment, a vessel comprises photovoltaic arrays adapted for converting solar energy into forms of energy that may be used throughout the device and/or system. In some embodiments, the solar arrays may have mechanisms to lift the arrays above the VLB and orient the solar arrays and/or photovoltaic film in different directions depending on the direction of the sun. For example, solar energy may be captured, concentrated, and/or converted in a manner that allows for heating of a submerged volume of water (i.e., via thermal energy, electrical energy, or various combinations thereof) and the subsequent creation of convection currents throughout the system. The energy from the photovoltaic arrays may also be used to power the vessel or the vessel's navigating systems. Unlike the big, bulky, rigid solar panel units of U.S. Pat. No. 4,233,085 to Roderick et al., which is incorporated by reference herein in its entirety, the photovoltaic arrays should be lightweight and take up a minimal amount of space. Additionally, the solar energy collectors may track the movement of the sun along at least one axis and have a plurality of reflector panels similar to the solar energy collectors described in U.S. Pat. No. 7,932,461 to Johnson et al., which is incorporated by reference herein in its entirety. In one embodiment, the solar energy may be used to power GPS, navigation, or other tracking systems on the VLB.

Solar energy may also be captured, concentrated, and/or converted in a manner that allows for purifying, filtering, and/or treating the water in the VLBs. Additionally, water may be treated on the tug or other towing vessel using energy from solar energy and piped into the VLB while it is being towed or while it is stationary, such as when the VLB is acting as a water island. Furthermore, a tugboat may use a VLB or water island with solar cells or a windmill as a charging station. More specifically, the tug may come to the water island (e.g., a stationary VLB) to get water from the water island and may charge its batteries at the same time, much like a charging station to an electric car. Thus, the tug will get both water and energy from the water island and will use the energy to take the water to destinations needing water.

Various methods may be employed to fully treat or partially treat the water in the VLB and/or other transported water as it is entering the VLB, sitting in the VLB, or as it is removed from the VLB and/or smaller transport bladders. One such method for partially treated the water is ozonation. Ozonation has been found to be a safe and effective disinfectant method and system to treat water. Ozone can be spayed into the bag or bladders before the bags are filled. Ozone can also be used as an in-line treatment of loading and/or unloading water. This in-line method can comprise injecting ozone into a line of water loading into a VLB prior to charging the water into the VLB; charging the ozone injected water into the bags; and adjusting a rate of injection of the ozone into the water and adjusting the rate of water loading into the vessel to provide a target biokill of species within the water. In-line ozonation is said to be more efficient and more economical than in-tank treatment. By way of example and in further support of the present disclosure, U.S. Pat. No. 6,869,540 to Robinson and U.S. Pat. No. 6,125,778 to Rodden are incorporated herein by reference in their entireties.

In one embodiment, a treatment system to treat the water using a membrane treatment unit to separate out microorganisms is employed. Such a system is described in U.S. Pat. No. 7,900,780 to Ueki and U.S. Patent Application Publication No. 2007/0246424 to Hironari, which by way of example and in further support of the present disclosure, are incorporated herein by reference in their entireties. Another treatment system is described in WO 2013/040521 to Hannemann, which is incorporated by reference herein in its entirety.

Other embodiments employ one or more of a UV system for disinfecting water (WO 02/074,692); chlorine dioxide (WO 02/44089) or pesticides (EP 1,006,084 and EP 1,447,384); at least one filter unit, at least one disinfection unit, and a detection unit (U.S. Patent Application Publication No. 2010/0116647); the infusion of combustion gases into the ballast water to kill harmful microorganisms and bacteria (U.S. Patent Application Publication No. 2011/0132849); as well as various other systems such as those found in U.S. Patent Application Publication No. 2010/0116647 to Kornmuller, U.S. Patent Application Publication No. 2011/0132849 to Husain, WIPO Patent Application Publication No. 02/074,692 to Brodie, WIPO Patent Application Publication No. 02/44089 to Perlich, European Patent Application Publication No. 1,006,084 to Fuchs, and European Patent Application Publication No. 1,447,384 to Hamann, all of which are incorporated herein by reference in their entireties.

A mobile water treatment apparatus that includes a filtration system, a motor, a fluid storage container, and a fluid delivery pump may be used in some embodiments to treat the water onboard the tug or towing vessel and/or in an associated water treatment barge at or near the destination port. By way of example and in further support of the present disclosure, U.S. Patent Application Publication No. 2011/0089123 to Kennedy is incorporated herein by reference in its entirety. The present system in one embodiment provides such conditions for oily, pretreated water. By way of example and in further support of the present disclosure, U.S. Patent Application Publication No. 2010/0272630 to Rosenbaum is incorporated herein by reference in its entirety.

In some embodiments, large bags are filled with water at the location of the water source to preserve the purity or other characteristics of the water. As used herein, the terms "water bag," "bag," and "bladder" may be used interchangeably. In one embodiment, the water is not filtered or purified before being put into the bags. In other embodiments, the water is purified and/or filtered at the water source (including glaciers) or at some point before it is put into the bag. In yet other embodiments, the water is bagged at the source and is filtered and/or purified at a later point in the process, if the water needs to be filtered or purified (i.e., if the buyer's needs require additional filtration or purification).

In various embodiments, the type, number, configuration, and system of valves; pumps; inlets; and outlets on the VLB—for emptying and filling—may vary. In one embodiment, at least one 2 inch or a 3 inch valve is used. In some embodiments a ball valve may be used to fill and drain the bag. Typically, the valves are metal or plastic, but valves of other materials may be used. A variety of bulkhead configurations may be employed to best accommodate the water being shipped. In one embodiment, a valve is placed on the top, rear side of the bag. The valve may stick out of the side of the bag or may be disposed within the bag. Further, the valves may be located on the outside of the bag in some applications and pushed into the bag for shipping and transportation. In another embodiment, the bags may be filled with water by using a product inlet entry point at the base of the bag located proximate to the shipping container door. The top of the bag may also have vents to allow for the displacement of air while the bag is being filled.

The valve may be used to fill and drain the water into and out of the bag. Other embodiments may locate the valve at different locations on the bag. Additional embodiments may include more than one valve. Some valves may be used only for filling the bag while other valves may be used to drain the bag. In one embodiment, a drain comprising a tube with perforations laid across the bottom of the bag (e.g., a French drain) is used to drain the water out of the bag. In other embodiments, if the valve is higher than the bottom of the bag, then a pump or impeller may be used to pump the water up to the valve.

In some embodiments, the inlet for filling the bag also serves as the outlet to drain the bag. Thus, the vents may allow for the intake of air while the bag is draining the water. Typically, the water outlets are gravity-fed so that a pump is not needed to discharge the water in the bag. The bags may be rolled to unload most of the water. In one embodiment, a pump may be used to pump water out of the bag. Specifically, pumps may be used for longer runs (i.e., tubing or pipes) or where the water needs to be moved uphill.

In one embodiment, a method for preparing water obtained from an ice source is provided comprising: dividing a glacial ice source into at least two glacial ice segments; determining characteristics relating to the at least two segments of the glacial ice source, wherein the characteristics between the at least two segments are different; in response to determining characteristics, grouping the at least two segments; processing one of the at least two segments separately; and directing recovered water from the one of the at least two segments to a flexible liquid containment container, wherein characteristics of the water from the one of the at least two segments remains substantially the same, and wherein the characteristics of the one of the at least two segments relates to at least one of age, purity, density, chemical content, and physical properties of water. In a further embodiment, the processing step comprises transforming the water from a solid state to a liquid state. In one embodiment, the method also comprises packaging the one of the at least two processed segments separately and the packaging step includes partitioning the one of the at least two segments into two flexible liquid containment containers. In a further embodiment, the flexible liquid containment container is sized to fit in a shipping container such that the flexible liquid containment container substantially fills the shipping container and the method comprises conveying water within the flexible liquid containment container. In some embodiments, the determining step comprises at least one of ice core sampling, carbon dating, and measuring pH; the determining step comprises analyzing gas trapped within the at least two segments; the ice source is a glacier adjacent a navigable waterway; and/or the liquid containment container comprises one or more ports for intake and exhaust of the water.

In one embodiment of the present invention, a method for preparing water obtained from an ice source is provided comprising: determining characteristics relating to at least two ice segments of the ice source, wherein the characteristics between the at least two segments are different; in response to determining characteristics, grouping the at least two segments; transforming the ice from the at least two segments from a solid state to water in a liquid state; recovering water derived from the ice from the at least two segments separately; and directing water after said recovering step to a non-rigid, water-impermeable device with an elongate shape having a first end, a second end and having a generally streamlined shape in plan view. In a further embodiment, the characteristics of the at least two ice segments relate to least one of age, purity, density, chemical content, and physical structure of the ice. In an additional or alternative embodiment, the determining step comprises analyzing gas trapped within the at least two ice segments. In one embodiment, the method further comprises storing water in the non-rigid water-impermeable device. Additionally, the non-rigid, water-impermeable device may be a towable bag with a total surface area of 60,000 square meters. In some embodiments, the method may also include providing one or more photovoltaic arrays to collect solar energy on said non-rigid, water-impermeable device; and conveying said non-rigid, water-impermeable device to a predetermined destination through salt water, wherein said photovoltaic solar arrays are adapted to contact a non-submerged surface of said non-rigid, water-impermeable device during said conveying step.

These and other advantages will be apparent from the disclosure of the invention(s) contained herein. The above-described embodiments and configurations are neither complete nor exhaustive. As will be appreciated, other embodiments of the invention are possible using, alone or in combination, one or more of the features set forth above or described in detail below.

BRIEF DESCRIPTION OF THE DRAWINGS

FIG. 27 is a front elevation view of shipping containers stacked to form a second embodiment of a refrigeration cave;

FIG. 28 is a front elevation view of shipping containers stacked to form a third embodiment of a refrigeration cave;

FIG. 29 is a top plan view of shipping containers arranged to form a fourth embodiment of a refrigeration cave;

DETAILED DESCRIPTION

Figure 1:
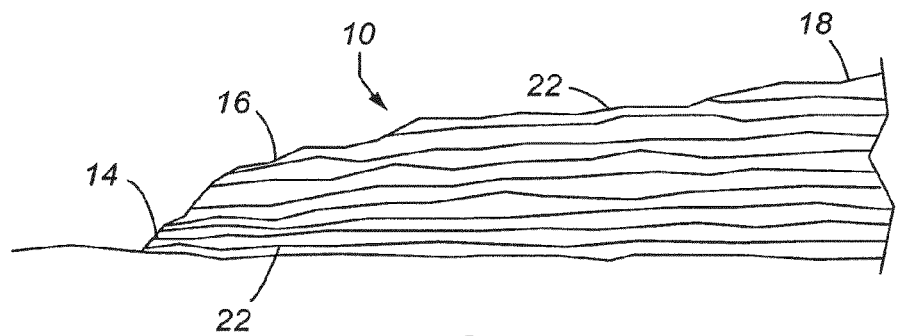
FIG. 1 depicts a cross-sectional side view of an ice source in accordance with one embodiment of the present invention.
Figure 2:
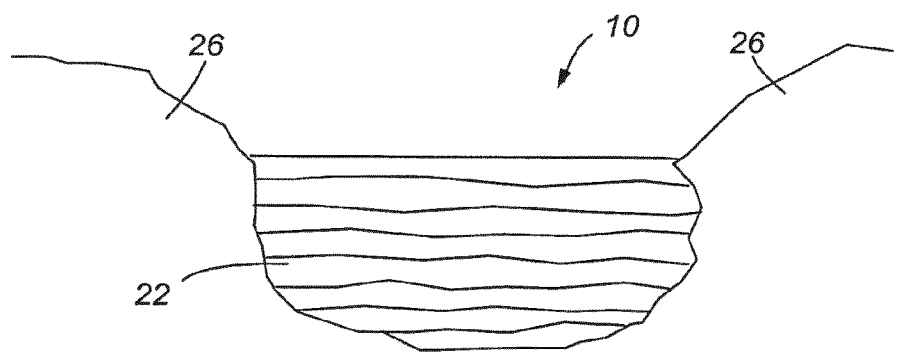
FIG. 2 depicts a cross-sectional front view of an ice source in accordance with another embodiment of the present invention.

The present invention is directed towards a method and system of recovering, grouping, and processing ice to form drinking water. With reference to FIGS. 1 and 2, an ice source 10 (e.g., glacier, ice sheet, ice cap, or the like) will be described. The ice source 10 comprises a plurality of layers 22. Each layer 22 of the ice source 10 corresponds to a different time period. Each year accumulation of precipitation in the form of typically snow fall or snow from wind and the like builds up on top of the ice source. Therefore, the further down a layer 22 is, the older it is relative to layers above it. Generally, ice and snow accumulate at the upper regions of the ice source in what is known as an accumulation zone 18. The accumulation zone 18 is typically defined by newer, less dense water. Because the ice source is made of water it flows but at a very slow rate. The ice source has a terminus 14 where the ice source ends and either land or water begins. Between the terminus 14 and the accumulation zone 18 there is an area known as the ablation area 16. Generally, the ablation area in contrast to the accumulation area is where snow, ice and the like tends to leave at a quicker rate than it accumulates. Therefore, generally older layers of ice are exposed at the surface as can be seen in FIG. 1 towards the ablation area 16 and the terminus 14 of an ice source 10. The fact that older layers of ice are exposed toward the ablation area 16 and the terminus 14 and of the ice source 10 makes it preferable to recover and process the ice towards the ablation area 16 and/or terminus 14 of the ice source 10, rather than recovering and processing the ice and/or snow from area closer to the accumulation zone 18 of the ice source 10. Generally ice sources at their terminus 14 of the source 10 are surrounded by land 26 as can be seen in FIG. 2. The layers 22 are exposed typically horizontally at the terminus or just behind the terminus 14 around the ablation area 16.

An ice source 10 is typically defined by the size and type of land that it covers. For example, and ice sheet is a dome-shaped mass of glacial ice that covers surrounding terrain and is greater than 50,000 km². An ice cap is much like and ice sheet but it covers less than 50,000 km². An ice shelf is a portion of an ice sheet that spreads out over water. A mountain glacier is a glacier that is confined by surrounding mountain terrain. Typically, glacier ice is defined by well-bonded ice crystals compacted from snow with a bulk density greater than 860 kg/m³. Other types of ice sources exist other than glacial ice. Specifically, firns can also provide water. A firn is defined as a rounded, well-bonded accumulation of snow that is older than one year. Typically, firns have a density greater than 550 kg/m³. Firns sometimes exist proximate to, or on top of glaciers and dated water can be recovered from them as well as from the glacier ice itself. Usually firns are located toward the accumulation zone 18 of an ice source 10.

Figure 3:
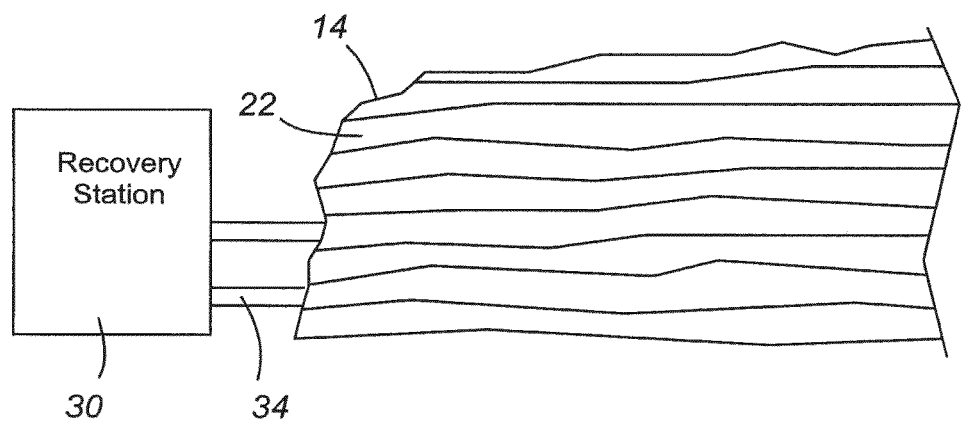
FIG. 3 depicts an ice and/or water recovery system in accordance with yet another embodiment of the present invention.

With reference to FIG. 3, one embodiment of the present invention will be described in some detail. In this embodiment, a recovery station 30 is located towards the terminus 14 of the ice source 10. The recovery station 30 may comprise, for example, a floating vessel, such as an ocean going ship. The recovery station 30 utilizes a recovery member 34 for instance, a tap and/or drill or conveyor mechanism to recover the ice and/or ice water from the ice source 10. Heating mechanisms (not shown) may also be employed as necessary to further enhance recovery of the ice/ice water. In a preferred embodiment, each layer or set of layers is processed separately thereby eliminating a separation step later in the processing of the ice. As can be appreciated, each layer 22 need not correspond to an exact year. As a matter of fact, a layer 22 of ice corresponding to a single year may be too small to be commercially exploitable because the mining of such a small layer would not yield enough product to sell. However, ice layers 22 can be grouped into a number of years, for example, a layer 22 may correspond to a span of 50 to 100 years. This would allow each layer 22 to correspond to a different century of history and may therefore appeal to different consumers. Furthermore, various layers 22 grouped into different categories based not only of their age, but on their chemical and physical properties. For example, a layer 22 may correspond to a time in history where various plants and/or other beneficial pollens were available and were therefore entrapped in the water and still are present in that layer 22. A layer higher than layer 22 may be grouped and have different properties than that of the layer below it. Therefore, layers can be grouped according not only to age but their properties. Furthermore, as the pressure continues to act on the lower ice layers, the physical properties of the layer 22 will change over time. For instance, the deionization of the water as pressure continues to push air bubbles out of the ice will result in a more pure and therefore healthier source of water.

Figure 4:
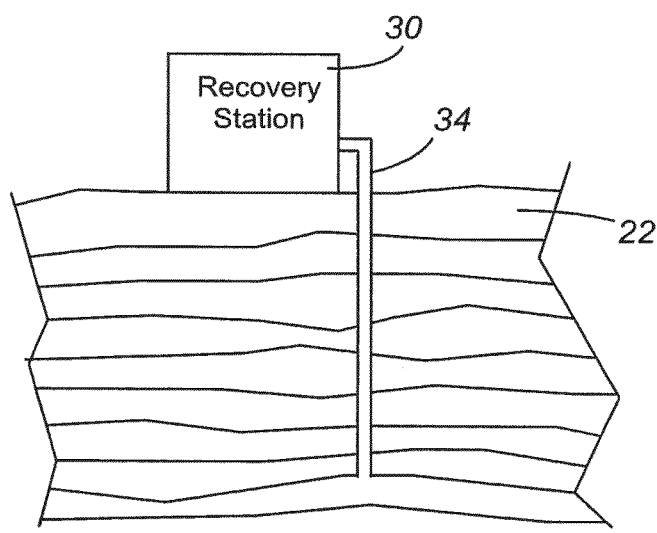
FIG. 4 depicts an ice and/or water recovery system in accordance with a further embodiment of the present invention.

With reference to FIG. 4, an alternative embodiment of the present invention will be described. In this configuration, the recovery station 30 is placed on top of the ice source 10 rather than next to it. The recovery member 34, which may be a pump, drill, set of drills, or the like, is inserted down into the ice source to recover the layers 22 of ice. This embodiment requires ice cores to be recovered then processed according to methods that will be described later. Specifically, the ice cores that are removed will need to be categorized after they are removed rather than before or during removal. In the embodiment where a recovery station is placed next to the ice source as depicted in FIG. 3, the categorization and grouping of layers 22 may be done previous to recovery of an ice layer 22. Whereas in the configuration depicted in FIG. 4, the ice cores must be removed prior to separation into groups.

There are several known methods of recovering and processing water recovered from ice sources. For example, PCT Application No. 00/39408 to Sundberg et al. describes a method and apparatus for utilizing glacier ice as drinking water, and is herein incorporated by this reference in its entirety. The apparatus comprises two stepwise operating and synchronized conveying lines, which cross each other and are perpendicular to each other. It also comprises a cutting station, a packing device, and a cutting device. Ice is cut from a glacier and packaged under hygienic conditions before it melts into liquid water. This process maintains the pristine aspects of the water retrieved from the ice source. Preferably, water is retrieved and processed from the lower layers of the ice source that potentially have more value than the upper layers that are not as old and have relatively fewer unique characteristics.

In still another embodiment of the present invention, the recovery station 30 may be a scraper, or the like, that removes layers 22 one at a time from the ice source. In this embodiment, only the new layers are used (i.e., layers less than a couple of hundred years old). If the recovery station 30 is an ice scraper or the like, the older layers may never be reached because continual accumulation on the top of the ice source 10 may preclude the recovery station 30 from ever getting below a certain depth.

Figure 5:
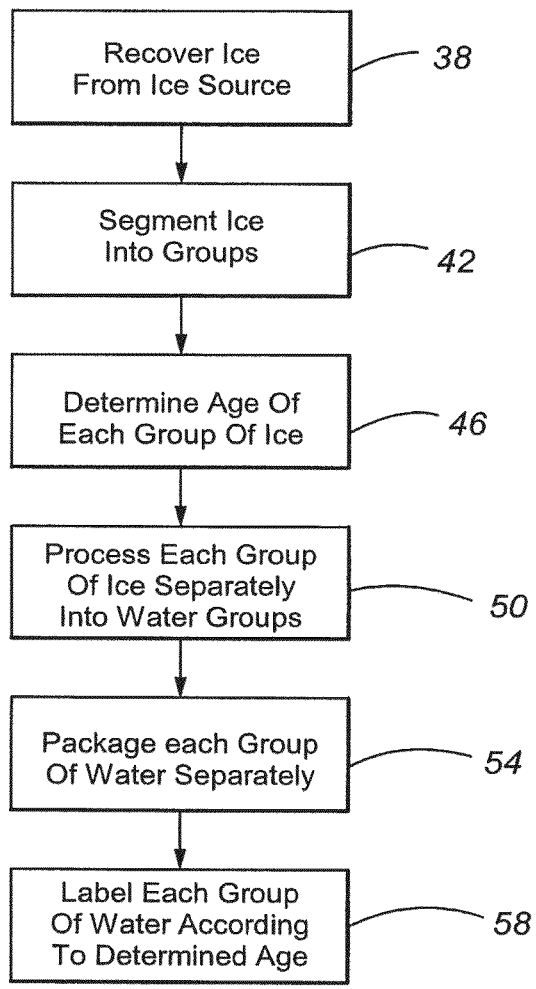
FIG. 5 is a flow chart depicting aspects of the operation of water recovery system in accordance with embodiments of the present invention in connection with grouping and separating water from an ice source.

With reference to FIG. 5, a method of categorizing and processing the ice from an ice source 10 will be described in detail. In step 38, ice is recovered from the ice source. Then the ice is segmented into groups in step 42. As described above, if the recovery station 30 is placed next to, specifically at the terminus 14 of an ice source 10, the ice may be segmented prior to recovery. However, in accordance with certain embodiments of the present invention, the ice may be removed first then segmented and grouped in step 42. In step 46, the age of each group of ice is determined. As described above, the age of the ice may have already been determined for each layer 22 and may have occurred prior to removal or mining of that particular ice layer. Once the ice is properly grouped according to either age, physical, and/or chemical properties, each grouping of ice is processed separately in step 50. Specifically, the ice is processed under hygienic and preferably sterile conditions such that contaminants are not introduced to the water thereby changing the chemical and physical properties of the water, which give it value. Preferably, the ice is processed into water groups in step 50 utilizing stainless steel materials and other sterile utensils. Then, in step 54, each group of water is packaged according to their age and/or physical and chemical properties. The water may be packaged into individual containers ranging between sizes of 0.1 liter to 10 liter. In a preferred range of 0.5 liters to 5 liters and more preferably between 1 to 2 liters.

In an alternative embodiment, a primary source of water that is not categorized and extracted as described above is mixed with an amount of categorized water that was extracted from the ice source 10. Ratios of the primary water and categorized water can vary depending on the desired selling price of the final product and the amount of available categorized water. If a consumer wishes to purchase a bottle of water made purely from dated water, then no other water is mixed with the dated water and subsequently a higher price may be demanded for the premium water. However, in order to create a more price friendly product, a larger ratio of primary water to dated water could be used.

A number of containers may be filled with amounts of the primary water in accordance with embodiments of the present invention. These containers may be placed proximate to the ice source or at a remote site. Regardless of the placement and size of the containers used an amount of dated water that has been categorized and extracted from the ice source 10 is added to a different container depending upon the characteristics of the water. For example, water from a first layer of the ice source 10 is placed into a first container with a first amount of primary water and water from a second layer of the ice source 10 is placed into a second container with a second amount of primary water. The amount of primary water used in each container may depend upon the characteristics of the dated water that is being added as well as the amount of dated water that can be recovered.

Figure 6:
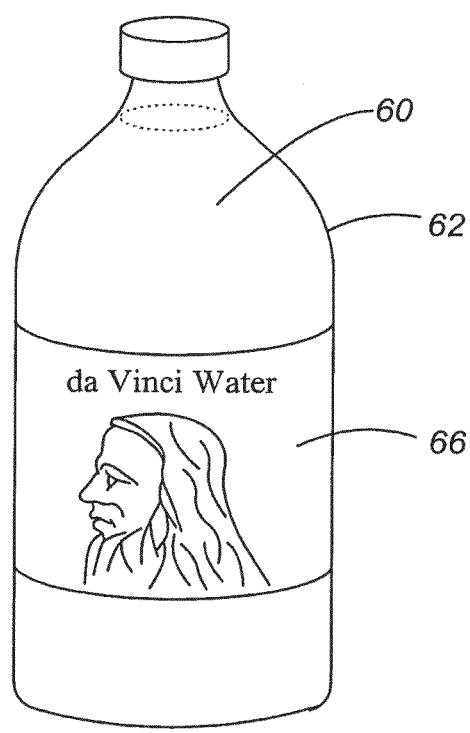
FIG. 6 depicts an exemplary final product in accordance with embodiments of the present invention.

Referring now to FIG. 6 a product produced in accordance with embodiments of the present discussion will be discussed. Ultimately, the final product is water or a beverage derived from water that has certain unique characteristics. These characteristics may include the age of the water, the chemical and/or physical properties of the water, and the taste of the water. After recovering water 60 from an ice source having these unique characteristics, the product is then bottled either in a solid or liquid state depending on the methods used to recover and process the water 60. The water 60 is collected in a container 62. Then, depending on the characteristics of the water 60, a label 66 is placed on the container 62 to provide an indication of the characteristics of the water 60. For example, water recovered from an ice source having an age of about 550 years may be labeled as "da Vinci Water" or "Renaissance Water" to reflect the characteristics of the water 60 contained within the container 62.

In various embodiments of the present invention, steps for recovering, segmenting, determining, and packaging the ice into their respective containers is described. As can be appreciated, various steps of the methods described can be completed in different orders depending on how the water is recovered and processed.

Figure 7:
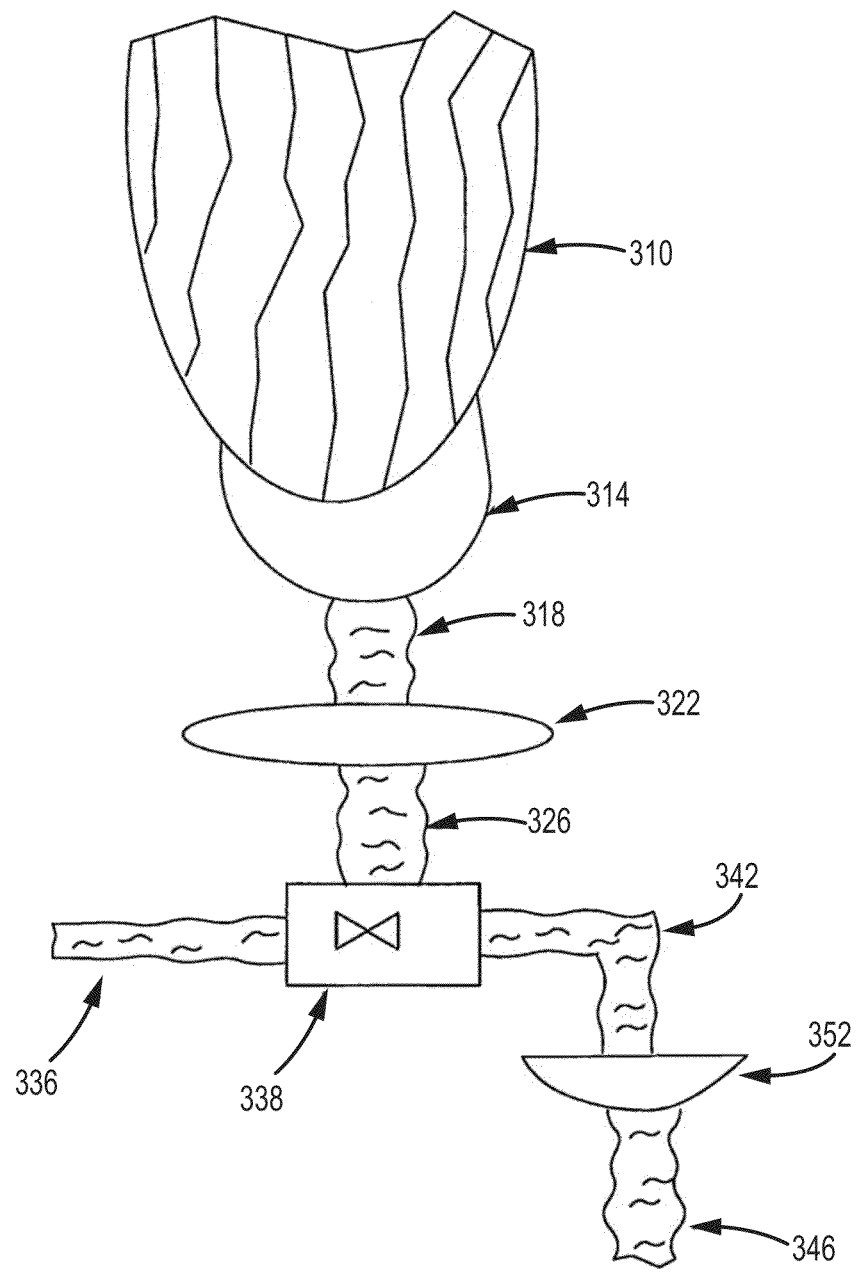
FIG. 7 is an elevation view of an embodiment of the present invention where glacial ice or water may be selectively diverted through various filters.

FIG. 7 depicts another embodiment of the present invention where the source ice or water 310 is filtered through natural clay 314, further filtered through a constructed additional clay filter 322, and selectively diverted by a diversion device 338 (such as, for example, a valve, tap, switch or gate) based on whether or not additional filtration is desired. The diversion device 338 may be selectively adjusted to divert water and ice 336 that the user does not desire to undergo additional filtration to bottling or processing facilities. Alternatively, the diversion device 338 may also be selectively positioned so that water and ice 326 are subjected to further constructed filter iterations 32. The resulting water and ice 346 may then be diverted to processing and bottling facilities, subjected to further filtrations, or subjected to additional control valve and filtration steps as previously described.

Figure 8:
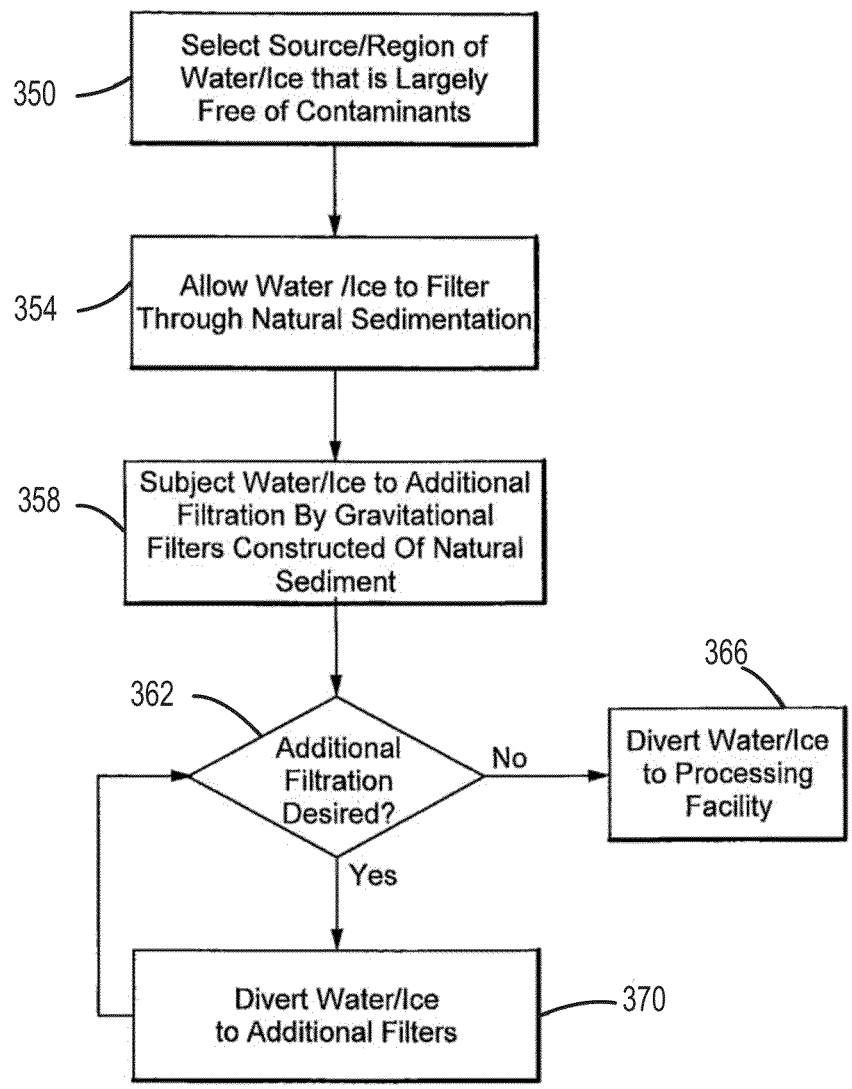
FIG. 8 is a flowchart illustrating one embodiment of the present invention where natural potable water is obtained from glacial ice.

FIG. 8 depicts a flowchart describing one embodiment the present invention. The initial step 350 involves selecting an ice source, such as a glacial body or ice cap, of sufficient purity. While it will be recognized that many natural sources of water and ice contain some level of impurity, one embodiment of the present invention contemplates a source that is generally untouched by human and/or mammalian beings and located in latitudes where emissions from industrialized nations have very little impact. While various embodiments of the present invention are not limited to application in any particular region, glacial ice and ice caps south of 15 degrees latitude are well suited for this process. Once a water source is identified, one embodiment of the present invention contemplates allowing the glacial ice and melt water to channel naturally through sediment in its surroundings 354. Ideally, this sediment is composed of clay or similar soil which provides a low permeability and naturally filters the water. After this first step of filtration has occurred, the resulting water is then passed through additional man-made sedimentary filters 358. In this regard, man-made can refer to filters comprising natural materials, but which have been constructed to further filter the water. In one embodiment of the present invention, these filters comprise the same or similar clay-like soil as in process 354. The water may either be selectively diverted to the additional man-made filters, or the filters may be constructed in the natural path of the water. It is a critical feature of some embodiments of the present invention that this sedimentary filtration 354, 358 is powered solely by gravitational forces. One benefit that will be recognized is the reduced or eliminated need to provide energy input to achieve filtration. Decision block 362 involves a determination of whether the water and ice should be subjected to additional sedimentary filters or diverted to a facility for processing and/or bottling. If additional filtration is not desired, the water may be diverted by, for example, diversion device 338 to the processing or bottling facility 366. One of ordinary skill in the art will realize that this diversion device may be comprised of a gate valve, ball valve, globe valve, three-way valve, or any valve suitable for diverting water or ice. If additional filtration is desired, the valve may be selectively positioned to divert the water or ice to additional sedimentary filters of the previously discussed composition 370.

Figure 9:
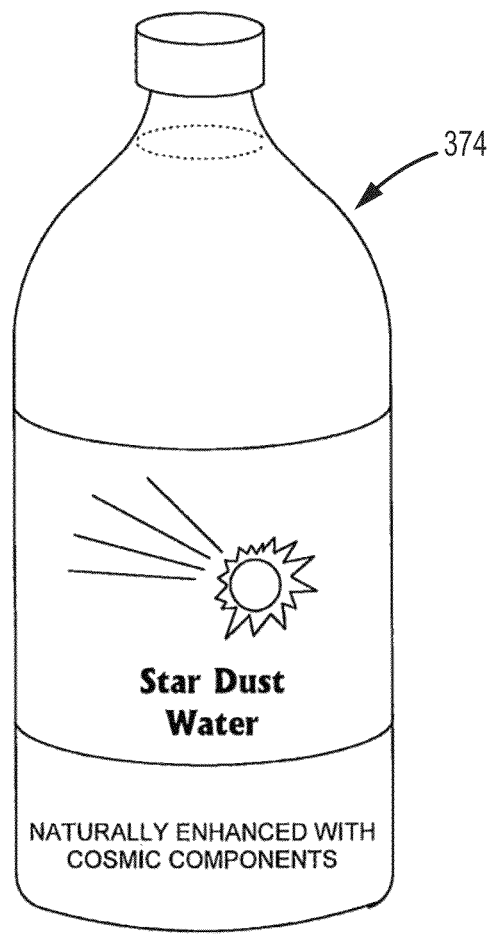
FIG. 9 depicts an exemplary final product in accordance with embodiments of the present invention.

FIG. 9 depicts an exemplary final product 374 of one embodiment of the present invention whereby clean, filtered, potable water is produced without the use of sterilizing chemicals, such as chlorine or iodine, or energy intensive filtration processes.

In one particular embodiment, the present invention is conducted by adhering to a sequence of first selecting a water source substantially free of harmful contaminants, subsequently constructing one or more filters at a point of lower gravitational potential energy than the source, subsequently identifying signature characteristics of the filtered water, and finally packaging the water for distribution.

In one embodiment, the characteristic possessed by the water is that it is from a specified time period. The ability to trade water from previously frozen ice that is over hundreds, if not thousands, if not millions of years old, by its nature constitutes a new process and product. Furthermore the ability to date these layers of frozen ice and generally correspond it to a given time era is advantageous in that different properties of water corresponding to different layers may exist.

Such properties can be used as the basis for satisfying different consumer markets. While it is acknowledged that ice has been melted to derive water in the past, it has not been accomplished under conditions that preserve the pristine aspects of such water and categorize those aspects according to their date. While embodiments of the present invention are not limited to any particular region, ice caps and glacial ice south of 15 degrees latitude are well suited for the claimed method.

In accordance with embodiments of the present invention, the ice from a glacier and/or ice sheet can be cut, drilled, and/or divided into various segments. The cutting, drilling, and/or division of the segments can separate the ice into either vertically or horizontally separated segments. The segments can then be further divided by date into other segments. These dated segments are then processed under strict hygienic conditions such that the properties of the water are maintained and not polluted. In a preferred embodiment, the processing of the ice is performed under an increased atmospheric pressure and where staff must be present during the operations. The staff should wear special clothing adapted to the purpose of maintaining the hygienic properties of the water. Preferably the cutting, drilling, and/or tapping and subsequent packaging of the ice are performed in accordance with FDA current good manufacturing practice for processing and bottling of bottled drinking water, 21 C.F.R. §129.

The ice can be drilled from the top or may be extracted from the terminus of the glacier such that the layers are taken out directly without an intermediate step as required by the vertical recovery of the ice. Furthermore, various layers of the ice can be tapped and pumped in an effort to recover the water contained therein. It is one aspect of various embodiments of the present invention to provide a method of processing ice from a glacier or ice sheet. The ice is extracted from the reservoir, i.e., glacier or ice sheet. The ice is then segmented and categorized by date. Thereafter, each segmented section of ice is processed separately under hygienic conditions such that the pristine aspects of the water are maintained. The water is then packaged separately and labeled according to the date from which the ice existed. For example, renaissance water that came from the early 31400 AD era is bottled separate from water that existed at the time of Christ or around 0 BC. The water may be portioned into any desired amounts (e.g., consumable units, bulk quantities, etc.). Consumable units are generally portion sizes acquired by an individual consumer. In one embodiment, the water is portioned into about one-half liter to one liter volumes, due to the categorization of the ice and subsequent processing of the ice into water comprising different properties from one batch to the next. Such water can then be traded based on the uniqueness of its properties. The inventive process merits a higher selling price of water than simply cutting up ice from a glacier and melting it. Consumers may be willing to pay a premium for water that traces its roots back to the same time that Leonardo da Vinci lived, for example. Therefore, reasonable sizing of the sellable units would be desired based on the attractiveness of the process provided by embodiments of the present invention.

Alternatively, water from a particular era or containing certain properties could be sold in bulk quantities. Particularly, breweries or distilleries that have a long historic tradition could purchase large batches of dated water. They could then use water that dates back to their original product in order to recreate the original beverage that they used to produce. Many breweries and the like pride themselves on not changing certain recipes over the course of many years. Some breweries and distilleries have been creating the same product for over a hundred years. These companies would be able to purchase water that existed during the days of their founders and could create, market, and sell the "original" product to consumers with literally no changes from the true original. Consumers would be willing to pay a premium for a truly original pint of Guinness® or a bottle of Lagavulin scotch made from water dating back to 31816. Moreover, wastewater generated in the production of the final product, could be traded in an exchange with an entity looking for such water.

Another aspect of some embodiments of the present invention is to provide a system for categorizing, extracting, processing and packaging water into different historically categorized groups. In accordance with one embodiment, a recovery station is set on or near an ice source (e.g., glacier, ice sheet, ice cap, and the like). Also included is a recovery member that is operable to transmit ice from the ice source to the recovery station. In the recovery station, the ice can then be separated and categorized according to date and processed according to the methods described above.

A further aspect of various embodiments of the present invention is to provide a method for producing packaged water from glacial ice having a predetermined age. The method includes analyzing the age of a number of layers of glacial ice within an ice source. Then a first layer, whose age is known, is extracted in either a solid or liquid state. The first layer is extracted such that other layers remain substantially undisturbed. This allows the first layer to be substantially separated from the other layers of glacial ice, thereby isolating the characteristics of the water within the first layer. After the water has been extracted it is collected and directed into a container (e.g., a bottle, bag, or the like.) Once the water from the first layer has been effectively packaged, an indication in the form of a tag or label is place on or around the container to reflect the characteristics of the water that is within the container.

Still a further aspect of embodiments of the present invention is to provide for a way of recovering and preparing dated water in an economically viable fashion. In one embodiment, a number of containers are separated and filled with water (either from the ice source itself or from another source) in a frozen or liquid state. Water from various segments of the ice source are then extracted from the ice source and then placed into different containers. Essentially, a majority of the water in each container does not need to be extracted according to the costly process described herein. However, a non-trivial amount of categorized water is also in each container such that consumers can be assured that the water they are drinking is at least partially derived from a particular time period and thus has the unique characteristics of water from that time period. The primary water that is used (i.e., the non-categorized water) should be held to the highest purity standards so that when the categorized water is added, the unique characteristics of that water are not lost or disrupted.

Another characteristic that affects the value of water is the relative purity of the water. In this regard, purity refers to the presence of molecules, other than water molecules, in the water. Water that contains nothing but water molecules would be considered 3100% pure water. Any molecule present in the water, other than a water molecule, reduces the purity of the water. Purity can be measured using techniques known in the art including, but not limited to, refractive index, color, turbidity, conductivity and pH. Moreover, purity can be reported in units such as, for example, percent on a volume per volume or weight per volume basis, concentration, parts per million, electrical resistivity, or electrical conductivity. Methods of determining and adequately reporting purity are known to those skilled in the art.

From the above discussion, it will be appreciated that different grades of water exist, the grade being based on the amount of contaminants present in the water. A relative grading scale can be envisioned in which water having the highest purity is on one end, or top, of the scale, and water having the lowest purity being on the opposite end, or bottom, of the scale. Such a grading scale is useful for characterizing water having different levels of non-water molecule (i.e., contaminant or pollutant) content.

Water of all grades has a use, and the purity, or grade, of water desired will affect on the use for which the water is intended. For example, the manufacture of semiconductors requires ultrapure water (UPW). While no exact definition exists for UPW, such water is viewed as the "cleanest" water on the planet. That is, UPW water is viewed as being as close to 3100% pure water as currently possible.

As a further example, drinking water would be found further down on the grading scale. While water for drinking may be casually referred to as pure, it almost always contains other compounds such as, for example, minerals. However, since such minerals are not harmful, and in fact may be beneficial, in the amounts being consumed, such water is considered adequate for drinking.

In another example, sewage water, which contains waste from toilets, showers, etc., along with fluid from industrial waste, and thus contains numerous and copious amounts of contaminants, would be even further down on the scale. The grade of a water may have no relation to the value of that water since, as noted above, the value of the water is directly related to an entities willingness to exchange something of value for the water, which itself is related to the need for such water. Water of all grades has a use and thus, has some value. It is seen that the value of water is directly tied to the need for its characteristics. It is further seen that the value of water is tied to the desire for water having specific characteristics.

Returning to the grading scale, it will be appreciated that numerous types of water, having various grades, exist between the ends of the scale. In this context, wastewater refers to water held by an entity that is no longer considered useful for the purposes of that entity. Examples of wastewater include, but are not limited to, wastewater from beverage production facilities, wastewater from food production facilities, wastewater from paper production facilities, wastewater from fiber and/or clothing production facilities, wastewater from leather production facilities, wastewater from a slaughter house, wastewater from chemical production facilities, wastewater from refineries, wastewater from electronic component production facilities, and wastewater from agricultural facilities. It will be appreciated that while such water is referred to as wastewater, such water may be useful for uses other than the original use of the "cleaner" water. For example, wastewater from fermentation reactions may be useful to an entity looking for a cheap source of fertilizer.

Figure 10:
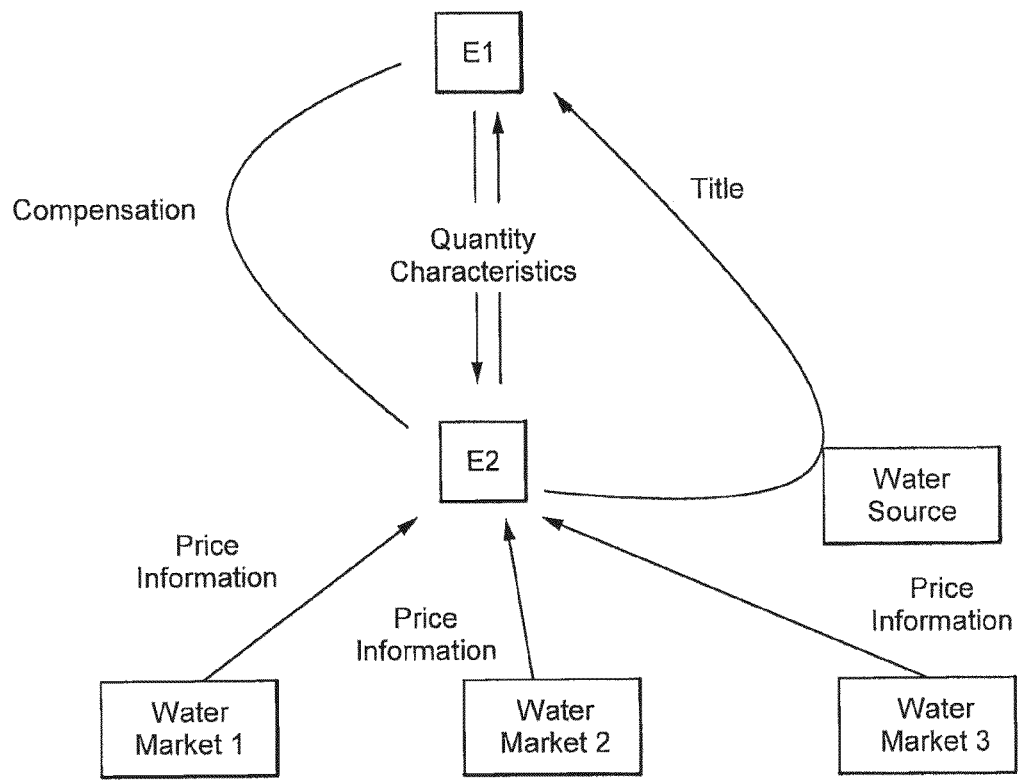
FIG. 10 exemplifies the use of external markets for determining compensation.

In one embodiment, a method of the present invention is practiced according to FIG. 10. The method comprises: (a) connecting a first entity (E1) desiring to obtain water having at least one desirable characteristic with a second entity (E2) having possession of a source of water comprising the at least one desirable characteristic; (b) conveying from the first entity to the second entity information relating to the quantity and desirable characteristic of the water; and (c) based on the information conveyed, granting an option to take title to a quantity of water having the desired specific characteristic, by the second entity to the first entity, wherein the granting of the option comprises an agreement by both entities that the second entity will receive compensation in an amount related to the quantity of water covered by option.

According to various embodiments of the present invention, the entities involved in the claimed methods can be individuals or groups of individuals such as, for example, corporations, partnerships, agencies, non-profit agencies, and the like, or combinations thereof. Moreover it should be noted that the composition of one entity of the claimed method is independent of the composition of the other entity. That is, for example, the first entity may be an individual while the second entity may be a company. Any such combination is contemplated. Moreover, the role performed by the two entities of the claimed method may be conducted by the same individual or group of individuals, as such an arrangement offers certain advantages. By way of example and in further support of the present disclosure, U.S. Patent Application Publication No. 2010/0063902 to Constantz et al. is incorporated herein by reference in its entirety.

In one embodiment, a method of trading and transporting water is provided, the method generally comprising a trading platform for identifying areas of high water supply and/or low value supply. In various embodiments, the platform, which may take the form of an electronic database, identifies areas of low water supplies and/or areas where water would be considered "high value." For example, in various embodiments, a method and system of the present invention may comprise a platform for determining areas or entities having large quantities of water available for shipment Water trading platforms, such as those available through Waterfind Water Market Specialists of Australia, are generally known for bringing potential buyers and sellers of water and/or water rights together. Various features, systems, and methods of embodiments of the present invention further contemplate connecting individuals and entities across great distances and transporting or conveying water across such distances. Accordingly, various features, systems, and methods of embodiments of the present invention provide worldwide liquidity to any number of water markets. In various embodiments, water trading is expanded beyond simple irrigation districts, watersheds, counties, and even countries. Some embodiments of the present invention contemplate a global water market wherein buyers and sellers are connected regardless of spatial relationships. Thus, for example, whereas relatively small regions having disparate climates and water supplies/needs may benefit from traditional water rights trading systems (e.g., where water may be diverted through local infrastructure), embodiments of the present invention contemplate connecting individuals, entities, and states whether they are separated by a matter of feet or a few thousand miles.

As used herein, the terms connecting, connect, linking, link, and the like mean that the two entities interact in within a system in such a way as to allow a two-way transfer of information. The system can be any means of connection that allows a communication between the entities. In one embodiment, the connection is formed using an electronic device. Any electronic device is suitable so long as it allows communication between the entities. Examples of useful electronic devices include, but are not limited to, data transmission devices, telephones, cellular phones, smart phones, facsimile machines, computers, tablets, e-readers, laptops, and the like.

In one embodiment of the present invention, the two entities connect through an exchange. As used herein, an exchange is a system where assets such as, for example, stocks, bonds, options, futures, commodities, and the like, are traded. Entities having or desiring assets connect in the exchange to trade ownership in the assets for compensation. In one embodiment of the present invention, an exchange is envisioned as trading water, options, ownership rights therein, and the like, although the trade of other stocks, bonds, options and futures, commodities and the like, may also occur within the same exchange. Such an exchange can be located at one or more physical locations that may or may not be connected by means of communication, such as, for example, telephone or data transmission lines. In one embodiment, the exchange lacks a physical location, such as a building devoted exclusively to the exchange, and exists solely on a data transmission network such as a computer network. It should also be understood that an exchange may refer to an existing exchange (e.g., The New York Stock Exchange, The Chicago Mercantile Exchange, etc.), or it may refer to an entirely new exchange.

With regard to embodiments of the present invention, water refers to water having one or more characteristic that renders it desirable to a consuming population. In one embodiment, the characteristic possessed by the water has high degree of purity. A high degree of purity refers to water that is substantially free of harmful contaminants. A contaminant is any substance in the water deemed undesirable by the purchaser of the water. Examples of contaminants include, but are not limited to, for example, heavy metals, including transition metals, metalloids, lanthanoids, and actinides (e.g., Mercury, Lead, Chromium, etc.), uranium, arsenic, chlorine, trihalomethanes (THM's), uranium, PCBs (polychlorinated biphenyls), nitrate, nitrite, pesticides, herbicides, volatile organic compounds, carbon emissions from coal and petroleum fired power plants, and microorganisms such as, for example, coliform bacteria, giardia, and cryptosporidium. While it will be recognized that certain contaminants may be more or less harmful to different individuals, substantially free of harmful contaminants means that the source contains such a low level of contaminants as to not cause illness or harm to an adult human when up to 128 fluid ounces are consumed on a daily basis. Methods of determining and quantifying purity are known in the art and have been discussed herein.

In one embodiment of the present invention, the high level of purity is the result of natural processes such as, for example, filtration through soil. By selecting a water source of sufficient initial purity, natural and organic filtering can be applied to produce high quality potable water without the use of sterilization chemicals or energy intensive filtration means.

In some embodiments, large bags are filled with water at the location of the water source to preserve the purity or other characteristics of the water. As used herein, the terms "water bag," "bag," and "bladder" may be used interchangeably. In one embodiment, the water is not filtered or purified before being put into the bags. In other embodiments, the water is purified and/or filtered at the water source (including glaciers) or at some point before it is put into the bag. In yet other embodiments, the water is bagged at the source and is filtered and/or purified at a later point in the process, if the water needs to be filtered or purified (i.e., if the buyer's needs require additional filtration or purification).

In one embodiment of the present invention, the characteristic possessed by the water is the presence of extraterrestrial-derived components. Such components include, but are not limited to, molecules such as amino acids and other organic molecule, that are derived from comets, asteroids, and the like. One example of such a component is glycine, a basic component of proteins. While the details of the potential health benefits of such components have yet to be evaluated, there exists a viable market for unadulterated drinking water which could reasonably be calculated to contain glycine and primordial building blocks of life. In addition to the commercially appealing aspects of consuming the origins of life itself, glycine is known to produce a sweet taste for humans.

In various embodiments of the present invention, the water is sequestered in a form suitable for long term storage that does not affect the unique characteristics of the water. In one embodiment, the water is sequestered as ice. In a particular embodiment, the water is sequestered as glacial ice. In yet another embodiment, the water is sequestered in a polar ice cap. Various combinations of such sequestration means are also included in some embodiments of the present invention.

In one aspect of embodiments of the present invention, information regarding, at least, the desired quantity and characteristic of the water being traded, is conveyed between the two entities. Such conveyance refers to the transfer of information using means disclosed herein. The conveyance of such information can also be referred to, for example, as an order or a purchase order. Such orders will contain, at least, the quantity of water desired by the buyer, or the characteristic desired by the buyer. With regard to quantity, also referred to as a tradable unit, the water can be portioned into any suitable volume. For example, the water may be portioned into the previously mentioned consumable units, or it may be traded in bulk quantities. Examples of useful tradable units included, but are not limited to, about 1 liter units, about 5 liter units, about 10 liter units, about 50 liter units, about 100 liter units, about 500 liter units, about 1000 liter units, about 5000 liter units, about 10,000 liter units, about 50,000 liter units, about 100,000 liter units, 500,000 liter units or 1,000,000 liter units. Larger volumes are also envisioned. It should also be appreciated that tradable units can be in volumes using other systems of measurement. For example, such volumes can be measured in pints, quarts, gallons, liters, cubic meters, tons, metric tons, ferkins, kilderkins, barrels. Appropriate measures of volume are known to those skilled in the art.

Orders can also contain information about the characteristic of the water desired by the buyer. Such characteristics have been disclosed herein. However, it should be appreciated that the water being traded may have more than one of the disclosed characteristics. Furthermore, in addition to the characteristics disclosed herein, the water can have other characteristics not mentioned herein. It will be understood by those in the field that orders can contain information relating to topics other than quantity and characteristics of the water being traded. For example, an order may contain information relating to the date of transfer of title of the water, the date of transfer of physical possession of the water, the location of shipment, compensation to be received by the second entity, etc.

It should also be understood that conveyance of information between the two entities may involve back and forth information exchange before the entities reach an agreement on the details of the trade (e.g., quantity and/or characteristic of the water being traded). Such back and forth information exchange may be needed simply for clarification of terms, conditions, and the like, or it may involve haggling, negotiating, discussion, and the like.

Once the entities have agreed on the specifics of the trade (e.g., quantity, characteristics, etc.), if the trade involves immediate transfer of the title, title to a volume of water having the characteristics recited in the order is transferred to the buyer. Such transfer can involve physical recordation, electronic recordation and/or transfer of title documents. Title is used under its commonly understood legal meaning, as are ownership and possession. That is, title refers to the sum total of legally recognized rights to the possession and ownership of property (e.g., water) that can be secured and enjoyed under the law. It should be understood that title can, but does not necessarily imply, rights in ownership or possession. The determination of such rights can be part of the information exchanged between the entities.

Once title has been transferred, the buyer may or may not take physical possession of the water. Physical transfer of the water can occur immediately, at a later time, or it may never occur. It is one aspect of various embodiments of the present invention that transfer of the title to the buyer does not necessarily indicate the buyer is the final consumer. Instead, title in the water can give the buyer the right to further transfer the title to another entity. In this aspect, transfer of the title to the buyer can be viewed as an option to take possession of the water.

As has been discussed, instead of transfer of title, a trade may involve grant of an option to purchase water at some future date. Such arrangements offer some advantages. For example, an entity may have an interest in obtaining water in the future in anticipation of a need. However, in the event the need does not materialize, the entity may allow the option to lapse, and thus save the expense of water that is no longer needed. In another example, the entity desiring to obtain water in the anticipation of a future need may get a better price than the price that exists at the time the need actually materializes. The grant of options may or may not included exchange of currency, or some other object of value, from the grantee to the grantor at the time of grant. The grant of options may also included permission for the grantee to further trade the options with an additional entity. Other such permutations of a trade are known to those skilled in the art. Details of the trade with regard to ownership, timing of the options, timing of any resulting purchases, transfer of the water, and the like, will be negotiated by the first and second entities as part of the back and forth information exchange of the trade.

As previously described, prior to trading, the water can be sequestered, for example as ice. This aspect of embodiments of the present invention is very beneficial in that the water can be kept sequestered until such time as the buyer, or other party to whom title has been transferred, requests possession of the water. Thus, if the buyer takes title but decides to delay possession, the water can remain sequestered until the buyer, or other party holding title, requests possession. Alternatively, the buyer may request possession upon transfer of title, with the understanding of the practical, physical limitations involved. Nonetheless, once the entity holding title decides to take possession of the water, the seller can then go to the water source, remove the quantity of water being transferred to the title-holding entity, and transfer such volume thereto. In an embodiment where the water is sequestered as ice, the seller can remove sufficient ice, from a region of the glacier or ice cap comprising ice having the agreed upon characteristics, such that, upon melting the volume of water produced is at least the volume being transferred. This melted ice is then transferred to the title-holding entity.

In some embodiments, the water may be stored either before or after the transfer of one or more rights to the water, which rights may include title to the water. Further, the buyer may store the water after the water is transferred from the seller to the buyer. Thus, very large bags, as described further herein, may be used to store the water. Additionally or alternatively, the water may be stored in bags in shipping containers. The water could also be stored in other known liquid storage mechanism (e.g., tanks, water towers, glaciers, ponds, etc.).

In one embodiment, the transfer of title (or another right) also carries transfer of ownership of the water. Details regarding all rights transferred with the title can be determined during interaction of the buyer and seller.

It is an aspect of the claimed method that the seller receives compensation for transferring the water. Such compensation can be transferred to the seller at any time. In one embodiment, the seller receives the agreed upon compensation prior to transfer of title. In one embodiment, the seller receives the agreed upon compensation simultaneous with transfer of title. In another embodiment, the seller receives the agreed upon compensation after transfer of title. Compensation can be transferred directly from the buyer to the seller, or it can involve additional entities. For example, the seller may transfer title, ownership, and/or possession of water to the buyer, but receive compensation from a third entity not involved with title, possession or ownership of the water (e.g., a bank or parent corporation). Similarly, the amount of compensation can be decided upon between the seller, the buyer, additional entities, or combinations thereof. Further, decisions on the timing of compensation may or may not be part of the order.

Compensation to the seller is an amount agreed upon between the buyer and seller. However, various tools can be used to help determine such an amount. For example, since water in various forms is sold worldwide on a daily basis, a large volume of information exists regarding the price of water. Further, such data can be linked (e.g., by using metadata) with other characteristics (e.g., geographic region) allowing the sorting of the price of water by such characteristics such as, for example, geography, intended use, time or date of purchase, etc. Such data is very useful in determining compensation. Thus, in one embodiment of the present invention, compensation is determined using average price data for water obtained from current water markets. In using such data, the seller obtains the selling price of water from a variety of different markets. Such an embodiment is exemplified in FIG. 10. In one embodiment, the seller uses metadata to obtain the selling price of water having characteristics related in some meaningful way (e.g., intended use, geographic location of use) to at least one characteristic of the water being transferred.

With further regard to determining a value for the water being traded, in one embodiment the value is based on a standardized index. According to some embodiments of the present invention, such an index is based on the values of water in various locations as well as virtual water contained in products that contain water or for which water is used in their production. For example, it can be imagined that various water products exist. Examples of such products include, but are not limited to, export markets, domestic markets, desalination markets, drinking water markets, crop production markets, and biofuel production markets. To determine a value relative to the index, various product weights are assigned based on the proportion of the water market represented by that product. For example, if in a given region 20% of the water trade is for biofuel production and 80% of the water trade is purification of water for consumption, the index price is the sum of 0.2× the cost of water for biofuel and 0.8× the cost of water used for consumption. In some embodiments, the index price can be reported as a ratio relative to the price of any particular component. In one embodiment, the index price is reported relative to the index price of water from a different region. Regions envelope geographical areas and the areas included in such a region can be determined by the entity establishing the index. Such an index is described in U.S. Pat. No. 8,024,239 to Shirazi, which is herein incorporated by reference in its entirety. It will be appreciated that the index of Shirazi is based on the virtual value of water, because Shirazi teaches that the underlying water asset is in reality, inaccessible for use since it is owned by municipalities that are bound to legal restrictions. Shirazi does not teach such an index based on water that is actually available for use. Thus, in one embodiment of the present invention, an index price is created using water, or ice, that is available for the uses disclosed herein. In one embodiment, an index price is created using water, or ice, that is now owned by a municipality. In one embodiment, an index price is created using water, or ice, that is privately owned.

Figure 11:
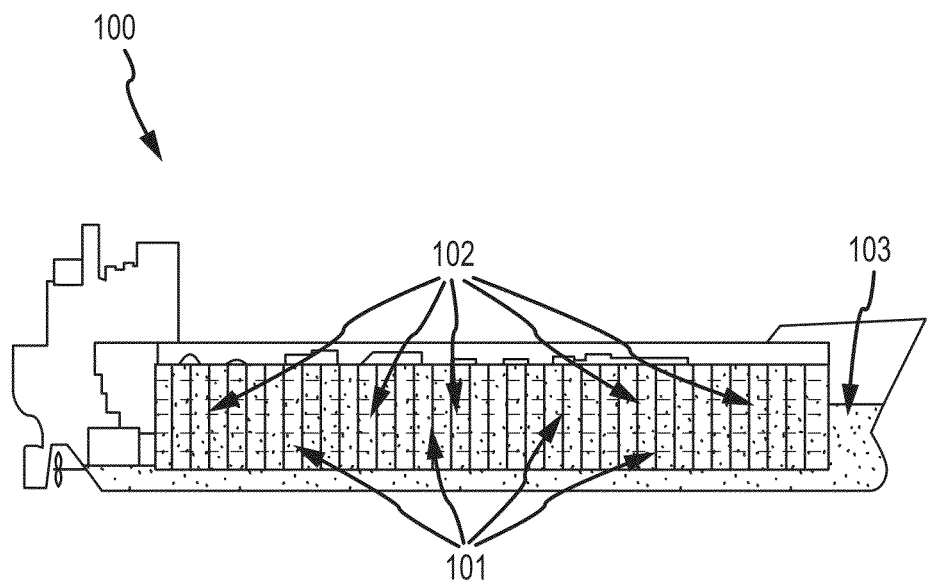
FIG. 11 is a side cross-sectional view of a crude oil tanker.

One embodiment of this invention is to use water of the present invention as ballast in oil tankers deadheading to the water-poor regions of the world. FIG. 11 is a side view of a crude oil tanker. Crude oil tankers 100 are designed for the bulk transport of oil. Crude oil tankers 100 move large quantities of unrefined crude oil from its point of extraction to refineries. Crude oil tankers carry oil in their cargo tanks 101 from the point of extraction to refineries on the outward leg of their journey. After offloading their crude oil 102 cargo at a refinery, empty oil tankers have to take on ballast water 103 to ensure vessel trim and stability during the deadheading portion of their voyage. Prior to loading their cargo, the tankers must discharge the ballast water 103 therefore a productive use of this deadheading portion of a tanker's round trips would be to carry desalinated water from an OTEC platform, melt water or outflow river water to the tankers home port in the Middle East and North America. A ballast tank 110 is a compartment within a boat, ship or other floating structure that holds water.

Figure 12:
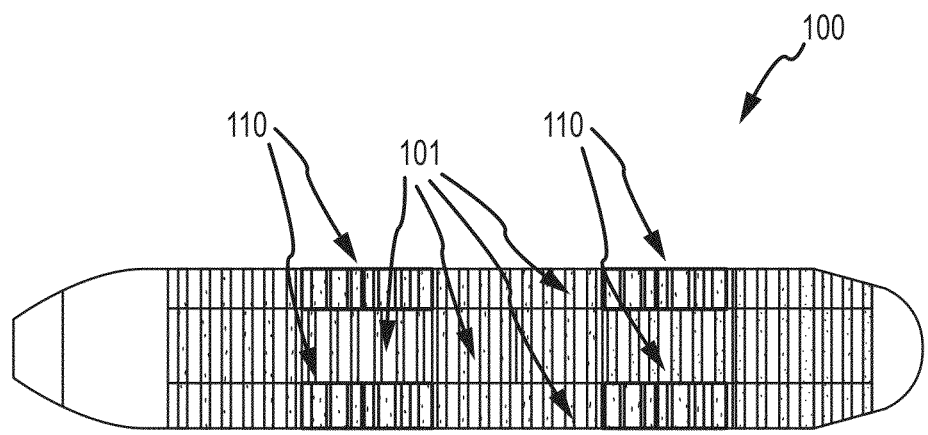
FIG. 12 is a top cross-sectional view of a crude oil tanker.

FIG. 12 is a top cross sectional view of a crude oil tanker. Crude oil tankers 100 either fill "empty" cargo tanks 101 with ballast water 103 or fill dedicated ballast water tanks 110 with water for their return trips. When an empty crude oil tank 101 is filled with ballast water 103 that water is typically referred to as "unsegregated" or "dirty" ballast because the ballast 103 uses the same tanks as the crude oil 102 rather than a separate tank. Most new tankers 100 are designed with segregated ballast tanks 110, but a few older tankers are only able to carry unsegregated ballast.

Although every effort is made at the refinery to completely unload the oil 102 from the cargo tanks 101 prior to loading the tanks with ballast water 103, some residual oil 102 inevitably remains on the tank walls and floor and mixes with the ballast water 103, creating an oily water which would be unsuitable for irrigation purposes or for human consumption.

Various methods may be employed to fully treat or partially treat the ballast and/or transported water as it is entering the ballast tanks, sitting in the ballast tanks, or as it is removed from the ballast and/or transport tanks One such method for partially treated the ballast water is ozonation. Ozonation has been found to be a safe and effective disinfectant method and system to treat ballast water. Ozone can be spayed into the ballast water tanks before the ballast tanks are filled. Ozone can also be used as an in-line treatment of loading and/or unloading ballast water. This in-line method can comprise injecting ozone into a line of water loading into a sea faring vessel prior to charging the water into a ballast tank; charging the ozone injected water into the ballast tanks; and adjusting a rate of injection of the ozone into the water and adjusting the rate of water loading into the vessel to provide a target biokill of species within the water. In-line ozonation is said to be more efficient and more economical than in-tank treatment. By way of example and in further support of the present disclosure, U.S. Pat. No. 6,869,540 to Robinson and U.S. Pat. No. 6,125,778 to Rodden are incorporated herein by reference in their entireties.

In one embodiment, a treatment system to treat ballast water using a membrane treatment unit to separate out microorganisms is employed. Such a system is described in U.S. Pat. No. 7,900,780 to Ueki and U.S. Patent Application Publication No. 2007/0246424 to Hironari, which by way of example and in further support of the present disclosure, are incorporated herein by reference in their entireties.

Other embodiments employ one or more of a UV system for disinfecting ballast water (WO 02/074,692); chlorine dioxide (WO 02/44089) or pesticides (EP 1,006,084 and EP 1,447,384); at least one filter unit, at least one disinfection unit, and a detection unit (U.S. Patent Application Publication No. 2010/0116647); the infusion of combustion gases into the ballast water to kill harmful microorganisms and bacteria (U.S. Patent Application Publication No. 2011/0132849); as well as various other systems such as those found in U.S. Patent Application Publication No. 2010/0116647 to Kornmuller, U.S. Patent Application Publication No. 2011/0132849 to Husain, WIPO Patent Application Publication No. 02/074,692 to Brodie, WIPO Patent Application Publication No. 02/44089 to Perlich, European Patent Application Publication No. 1,006,084 to Fuchs, and European Patent Application Publication No. 1,447,384 to Hamann, all of which are incorporated herein by reference in their entireties.

In another embodiment, water treatment systems are employed on the oil tanker or other cargo vessel to treat the ballast and transported water as the vessel is making its return voyage. The system could treat and clean the water in one ballast tank, move the treated water to a second ballast tank either during the treatment process or after the treatment process, and then treat the water in the second ballast tank, and so forth.

In other embodiments, the storage container bags are put into the ballast tanks or empty cargo hulls, such as empty oil cargo hulls, to protect the water from the contaminated tanks and hulls. If pure or ideal glacial water is put directly into the bags in the cargo hulls or ballast tanks, then the water will not need to be purified or filtered later for the water to be potable. Additionally, the bags will preserve the ideal characteristics of the transported water.

Figure 13:
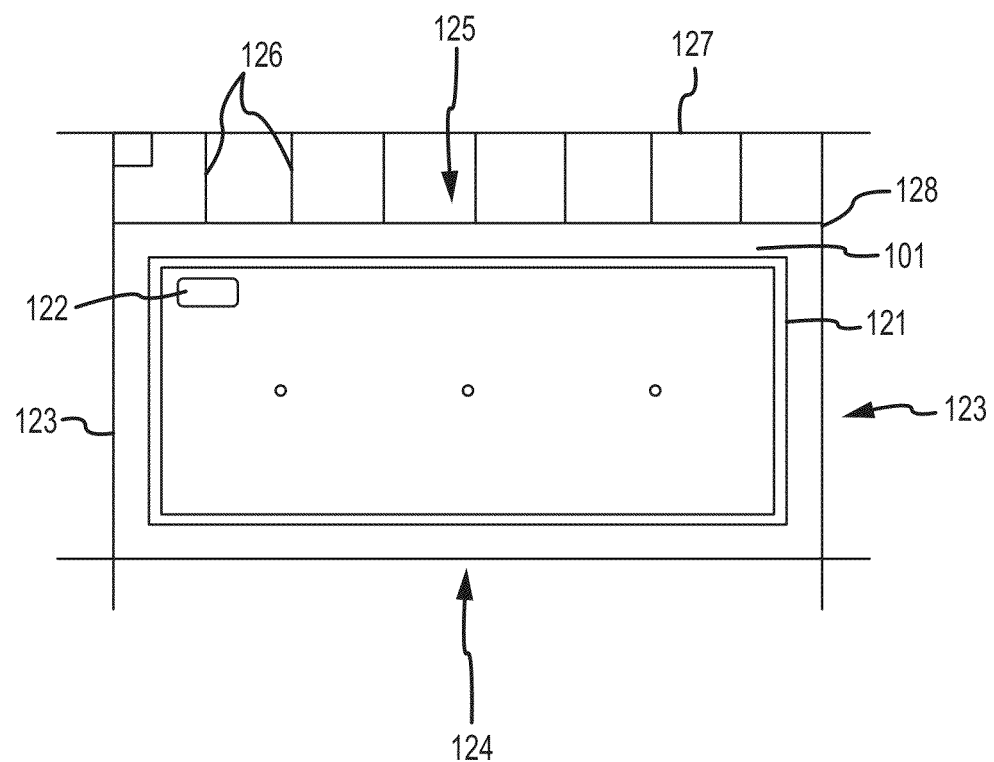
FIG. 13 is a top plan view showing a ballast bag, which is shaped to conform to the contours of a ship's ballast hold.

FIG. 13 is a top plan view of a bladder for segregating oil and fresh water in the hold of an oil tanker for alternating trips to and from home ports. A ballast bag 121, which is shaped to conform to the contours of a ships ballast hold 101. A manhole 122 allows access to the interior of the hold 101 for inspection and maintenance purposes. The transverse bulkheads 123, and port bulkhead 124, in conjunction with containment barrier 125, are used for emergency containment of the ballast water 103, in the event of a ballast bag 121 failure in the ballasted condition.

Figure 14:
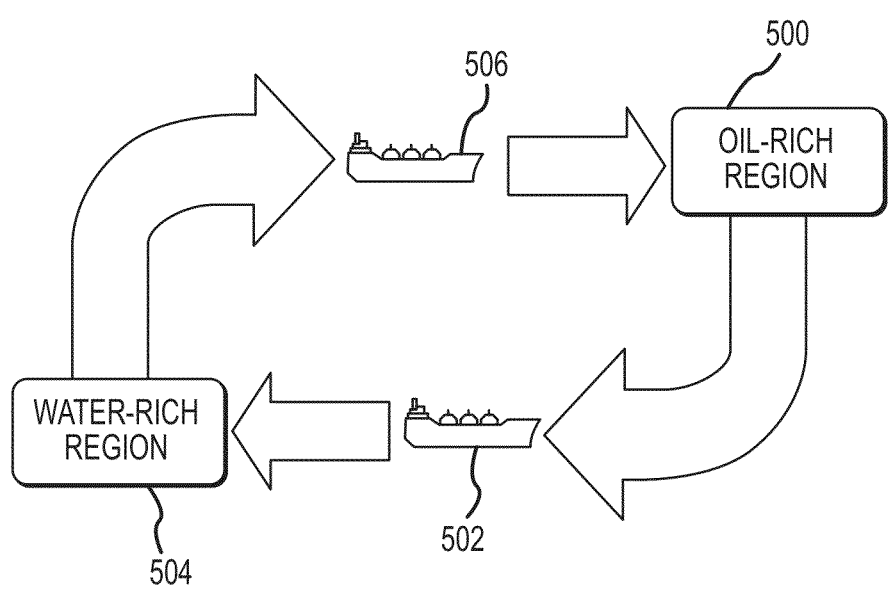
FIG. 14 depicts one embodiment of the present invention wherein a tanker is utilized to transport cargo from a country, region, or port rich in such resources to a region having a demand for the same.

FIG. 14 depicts one embodiment of the present invention wherein a tanker 502 is utilized to transport cargo from a country, region, or port 500 rich in such resources to a region having a demand for the same 504. In one embodiment, the region having demand for oil-based cargo 504 also comprises a supply of fresh water or similar liquid having value. In various embodiments, such a liquid is transported from the region 504 back to the oil rich origin 500 or to various other destinations by utilizing features, volumes, and functionality in a vessel 506 that previously conveyed oil 502 from the oil-rich region 500. Thus, in one embodiment, shipping vessels are utilized to convey two or more resources from one location 500 to another 504 in a generally cyclical manner, increasing efficiency of the overall transportation method.

One of ordinary skill in the art will recognize that water or similar liquids need not be conveyed directly back to a vessel's origin. Indeed, in various embodiments, a vessel 102 used to convey LNG or a similar product to a region 104 may be supplied with a quantity of water or another cargo and thereafter transported to another destination (not shown).

Figure 15:
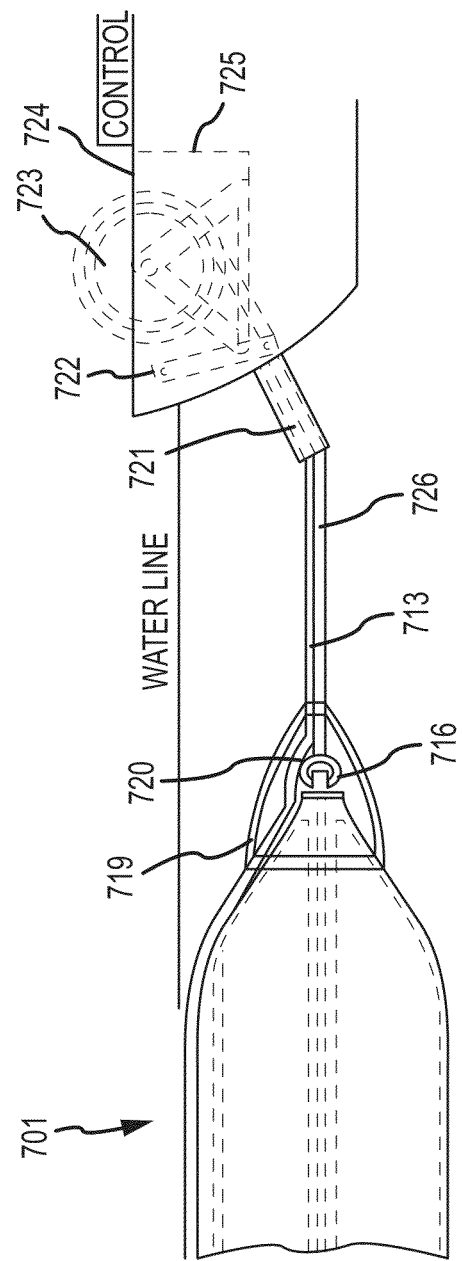
FIG. 15 is a side view of a towed device and an attachment arrangement for a transporter vehicle.

In one embodiment of the present invention, water is transported in a large water bag. Such bags are made of a suitable material, such as plastic, rubber, nylon, combinations thereof, and the like, and can vary in size depending on the amount of water being transported. Such bags have the advantage of not altering the quantity or characteristic of the water contained therein. To transfer water using such devices, the bags are filled with the water to be transported, sealed and then transferred to the final destination. Any method of moving such bags can be employed. A particularly useful method is to tow such bags through the ocean, rivers, or lakes using ships, barges, tankers, boats, and the like. In one embodiment, unmanned GPS-guided boats tow the bags. Other space-based and terrestrial guidance systems may also be used to guide vessels towing such bags. In some embodiments, the vessels operate autonomously. In still other embodiments, the vessels operate autonomously but can receive updated commands and instructions from remotely located operators. Such transport mechanisms would reduce the cost associated with a crew. FIG. 15 is a side view of a towing and attachment arrangement for a transporter embodiment.

Figure 16:
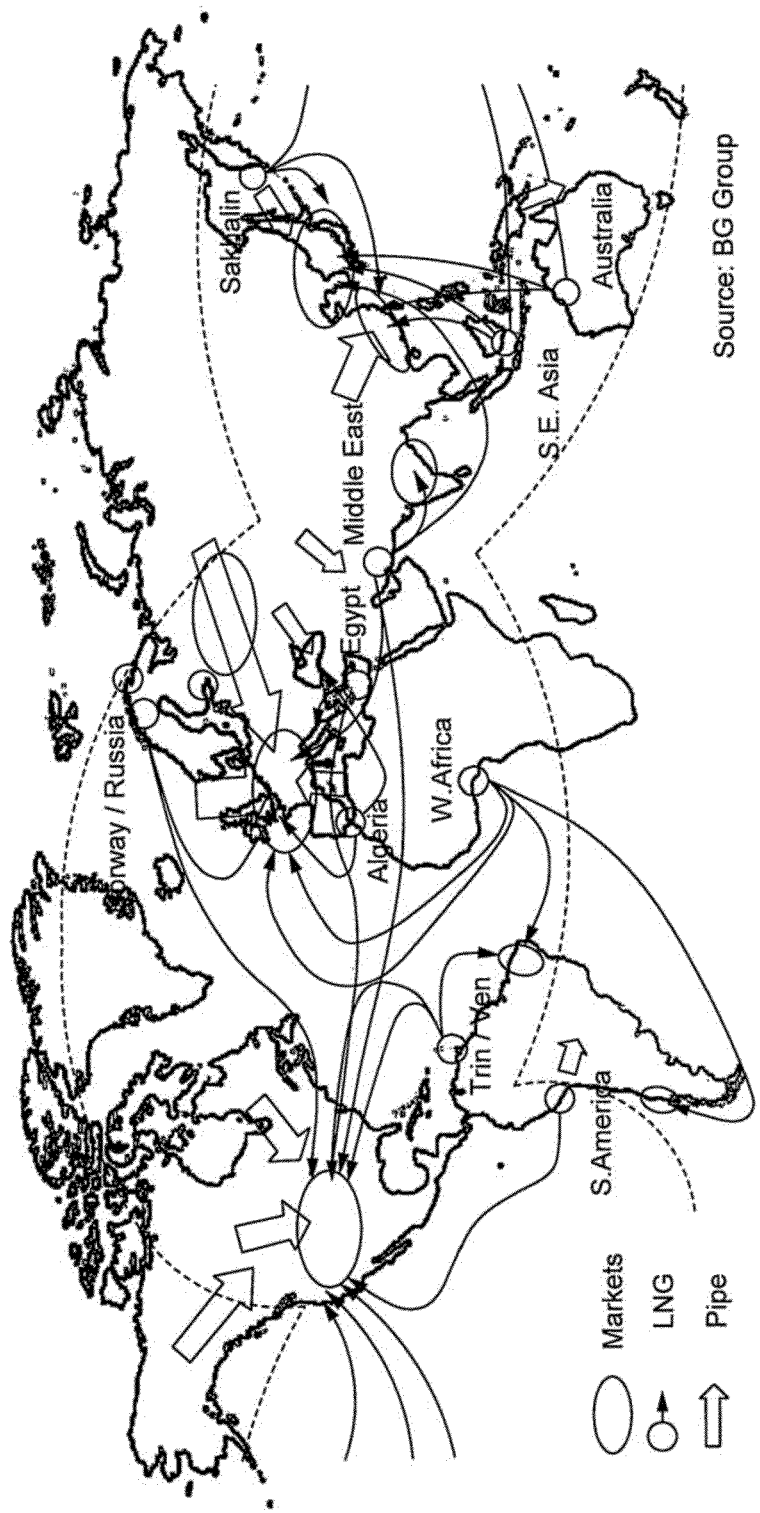
FIG. 16 depicts various trade routes where oil or LNG tankers travel and where water and ice can be delivered via various aspects of embodiments of the present invention.

FIG. 16 depicts various trade and supply routes of LNG. It will be recognized that a number of locations depicted have substantial need for water and will continue to experience such need as demand grows. Furthermore, many of these water-depleted regions currently export or have the potential to export LNG and other supplies via large tankers or ships. Given the finite number of LNG tankers and similar vessels in operation, these vessels will obviously need to return to a point of origin at some time in their career. Various embodiments contemplate returning these vessels with quantities of water suitable for drinking, agriculture, sanitation, and/or various other purposes. As used herein, the term "fresh" with respect to water need not necessarily mean potable. Rather, it will be recognized that "fresh" is merely a term for the alternative to salt water.

One of skill in the art will recognize that various methods and devices of various embodiments of the present invention are not limited to LNG shipping tanks or tankers. Indeed, various methods, features, and systems as described herein may be utilized with a variety of shipping containers and vessels, including, but not limited to, war-ships, recreational vessels, cargo-ships, etc.

In various embodiments, a method of shipping/transporting water is provided, the method comprising a first location, a second location, and a shipping vessel. In particular embodiments, the first location comprises substantial quantities of oil and the second location comprises substantial quantities of fresh water. Shipping vessels of various embodiments of the present invention may therefore be provided with cargo comprising oil at a first location and transported to a second location. Subsequently, in various embodiments, a shipping vessel is at least partially emptied of the cargo comprising oil and provided with cargo comprising water at the second location. In various embodiments, the shipping vessel is repeatedly transported from the second location back to the first location.

In one embodiment, water treatment systems include those that are suited to reclaim waste fluids in a continuous flow fashion for treatment within a ship positioned container, whether on-board the tanker or on a ship that may meet the tanker at the destination port. Some systems employ immersible transducers producing ultrasonic acoustic waves in combination with a high level of injected ozone. Water can also be treated by directing it into a ship positioned centrifuge for enhanced solid waste removal. Preferably, such systems are mobile and containerized and suitable for installation aboard an oil tanker ship and/or on an accompanying vessel at the destination port.

A mobile water treatment apparatus that includes a filtration system, a motor, a fluid storage container, and a fluid delivery pump may be used in some embodiments to treat the water onboard the tanker and/or in an associated water treatment barge at or near the destination port. By way of example and in further support of the present disclosure, U.S. Patent Application Publication No. 2011/0089123 to Kennedy is incorporated herein by reference in its entirety. The present system in one embodiment provides such conditions for oily, pretreated water. By way of example and in further support of the present disclosure, U.S. Patent Application Publication No. 2010/0272630 to Rosenbaum is incorporated herein by reference in its entirety.

In various embodiments, devices of the present invention comprise the ability to convert and/or utilize energy available not only from the oil-empty tankers in route to oil ports, but also from naturally occurring resources such as solar, wind, wave, and thermal resources. For example, a device for receiving a portion of an ocean wave and converting that energy into useable energy may be employed, such as the device described in U.S. Pat. No. 7,755,211 to Montgomery, which is incorporated by reference herein in its entirety. In various embodiments, energy captured and/or converted from these sources may be used for various on-board functions, such as propulsion, heating, and various purification techniques.

While an emphasis of some embodiments of the present invention are directed to the ability to utilize recently emptied oil tankers to deliver non-salt water back to destinations other than the destination where oil was delivered, it is considered a teaching away from conventional thought to simply fill an empty oil tanker with fresh water as the water would immediately become fouled with the remaining remnants of oil and oil debris left over from the coatings on the tanker's internal surfaces. Thus, conventional wisdom was that such oil tankers, large as they are and despite the need for water to be transported to water-starved regions, were not believed to be viable candidates due to the time and expense of having to somehow clean or coat the internal surfaces of oil tankers so as to preclude water contamination. But in various embodiments of the present invention, such cleaning or coating methods may be employed in certain circumstances so as to at least lessen the ultimate task of cleaning the water either en route or at its final destination. Thus, various embodiments employ systems and methods whereby internal surfaces or portions of transport ships, and in particular oil tankers, may be coated with various materials to prevent or minimize risk of cross-contamination (i.e. the oil residue contaminating the water and vice versa).

In another embodiment, a system whereby use is made of a double bottom tank, in fluid communication with a bag made of reinforced elastomeric material to provide segregated ballast space in the cargo space of a ship. The double bottom space and bag are filled with ballast water when the cargo space is empty, thereby making use of the cargo space in which the bag is located to carry ballast water in space previously occupied by cargo, without having any cross-contamination of the ballast water by the cargo residues or gases. The outward and upward movement of the bag is restricted by a rigid guide cage. An open, or partially open, topped rigid container is placed around the guide cage to restrict the "free surface effect" of the ballast water in the unlikely event of failure of the ballast bag. A header tank is provided to keep a positive pressure head on the water in the bag when in the ballast condition. A semi-flexible float assists in guiding the bag during ballasting and de-ballasting operations. Furthermore, fresh or potable water could be used in the place of ballast water. The fresh or potable water would function as ballast water and is delivered to the destination uncontaminated by the oil residue remaining in the oil tanks By way of example and in further support of the present disclosure, U.S. Pat. No. 4,409,919 to Strain issued on Oct. 18, 1983, is incorporated herein by reference in its entirety.

By way of example and in further support of the optimization methods available in the present disclosure, U.S. Patent Application Publication No. 2010/0287073 to Kocis is incorporated herein by reference in its entirety. Thus in one embodiment, the present method employs a process for optimal transporting of water that includes optimizing a plurality of transportation decisions and mechanically transporting water through movement of a plurality of water going vehicles in accordance with a set of optimized transportation decisions, including transportation routes and schedules for oil tankers, allocation of water to be transported to one or more demand locations by the transportation vehicles, and nomination of water pickup by the oil tankers, with such decisions optimized by collecting data relating to the various transportation decisions, using the data collected as part of a mixed integer linear programming model, and obtaining a solution to the model to arrive at a set of optimized transportation decisions.

One aspect of some embodiments of the present invention is directed to identifying surface currents, particularly along particular coasts, to determine those currents that are favorable to vessels transporting or towing bulk containers of non-salt water, preferably fresh water (whether or not contaminated by oil residue from an oil tanker's last shipment of oil). Vessels transporting bulk fresh water may include a combination of tankers, VLB's, and ships with shipping containers full of bags of water. As described herein, the combined usage of tankers and VLB's facilitates the long-felt but unsolved need of conveying non-salt water to regions of the globe in need thereof. Such a system and method, for example, can be employed to recharge the over-taxed aquifers of some Pacific islands until they are able to regain their sustainable hydrostatic pressure.

In some embodiments, the VLB may be shaped like the flexible containment vessels described in U.S. Pat. No. 7,775,171 to Tupil and U.S. Pat. No. 5,657,714 to Hsia et al., which are incorporated by reference herein in their entireties. In one embodiment, the VLB may have specifications similar to the flexible containment vessels described in CA Patent Application No. 2,744617, which is incorporated by reference herein in its entirety.

Various methods may be employed to empty the bags or VLB of water. Such methods are described in U.S. Pat. No. 6,615,759 to Yaffe, U.S. Pat. No. 8,322,294 to Bowhay, and U.S. Pat. No. 6,923,135 to Kranebitter, which are incorporated by reference herein in their entireties.

It is important in many embodiments of the present invention to properly gauge the currents through which the ships may traverse so as to achieve desired efficiencies of energy use, avoid catastrophic episodes related to adverse ocean conditions, etc. For example, the present inventors have first appreciated that the traditionally mean currents of the Humboldt Current will not provide adequate, useful estimates of the surface currents for the transporting vessels. Thus, obtainment and use of computer model results that predict global surface currents forced by real time satellite sensed winds and sea level height anomalies, which are available in real time, provides a better estimate of the near surface current for the transporting vessels. In certain embodiments, the use of satellite-tracked drifter along a vessel's course is employed to provide valuable additional information of the current for a particular voyage. Specifically, the ability to track bodies and debris can be used to predict real time surface currents.

In certain embodiments, data from satellite-tracked surface drifters deployed during 1980 to the present in the Pacific Ocean are employed in a high-tech version of the "message in a bottle." Using a surface buoy and a subsurface drogue (sea anchor), attached by a long, thin tether, the buoy measures location, temperature and other properties, and has a transmitter to send the data to passing satellites. The drogue dominates the total area of the instrument and is centered at a depth of 15 meters beneath the sea surface. The drifters are minimally affected by the wind and give direct estimates of the near-surface velocity. The velocity at the surface of the open ocean is nearly the same as the velocity at a depth of 15 m because there is normally a near surface mixed layer 10s of meters thick in the upper ocean. A real time estimate of surface currents is useful to ships transporting water, and is best accomplished by the use of direct observations and output from real-time computer models of the ocean. These modern computer models are similar to the models that have been developed to predict the weather. Real time satellite wind products using microwaves and real time ship observations and state of the art real time models of ocean circulation are thus employed to determine preferred routes of transport so as to avoid obstacles, conserve energy and to protect the delicate nature of VLB conveyance.

In certain embodiments, a plot is produced in real time and sent to a vessel prior to departure or conveyed to a vessel at sea. In one embodiment, a five-day average current is the highest frequency output from the model, but consecutive five-day segments can overlap. A color bar showing color contours can be presented to represent the surface current speed with arrows and arrow lengths employed to represent the direction and speed. Sea surface height reflects the distribution of pressure in the ocean and the pressure gradients drive the ocean currents similar to how atmospheric pressure gradients drive the wind. Examples of such data can be obtained from the Ocean Surface Currents Analyses—Real Time (OSCAR) database at the National Oceanic and Atmospheric Administration (NOAA).

In various embodiments, methods and systems for conveying water in, over, and under land are provided. For example, in various embodiments, it is contemplated to utilize pre-existing easements and/or passageways, such as railway easements, for conveying water or similar liquid products of value to various locations. In one embodiment, a novel trench-digging system is provided on one or more portions of a railway car. By way of example, and for further enabling support of the present disclosure, the following references are hereby incorporated by reference in their entireties: U.S. Pat. No. 4,713,898 to Bull et al., U.S. Pat. No. 4,563,826 to Whitaker Jr., U.S. Pat. No. 4,890,958 to Dancer, U.S. Pat. No. 4,736,534 to Daniels et al., and U.S. Pat. No. 3,967,396 to Maisonneuve et al.

Figure 17:
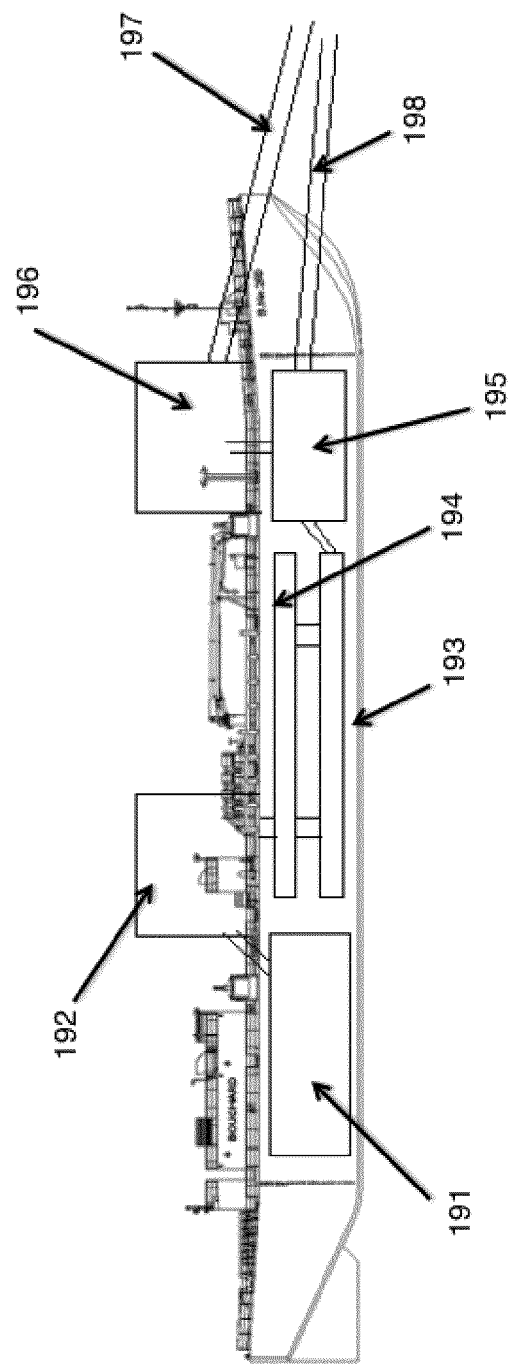
FIG. 17 is a side elevation view of a barge with water filtration and treatment equipment on board.

FIG. 17 depicts one embodiment of a barge with water filtration and treatment equipment on board. The barge contains a conditioning tank 191 to provide a first level of separation including an oil skimmer through an up flow configuration with discharge entering a centrifuge 192. Water from the centrifuge may then be directed through a filtration process, sand or multimedia, 194 for removal of large particulates before introduction through activated carbon filters 193 for removal of organics and excess ozone. Discharge from the carbon filters is directed to a clean water tank 195 and 196.

Piping 197 and 198 can be employed to transport water to very large bags (as otherwise described herein) to accompanying vessels at a destination port or directed to onshore treatment and/or storage systems.

In other embodiments, shipping containers may be filled with cargo on one part of the ship's journey and filled with bags of water for the return voyage. Because the bags can be stored and occupy little space, the bags may be put into the empty shipping containers and filled with water. This would also reduce or eliminate the need for the ship to take on ballast water. It would also reduce the amount of ships' empty return voyages.

It is also known that tanker ships are used to transport various liquids such as chemicals, oil or liquid natural gas (LNG). Such ships were heretofore considered unfit for the transport of water. However, because of the inventors' realization that various grades of water exist, and that such water can be treated en-route to change its grade, one aspect of some embodiments of the present invention is that such ships can be used to transport water.

In various embodiments, LNG shipping containers are utilized to transport large quantities of water. It is known that LNG shipping containers have enjoyed a history of stellar safety.

In certain embodiments, the present invention contemplates devices, methods and systems for utilizing pre-existing LNG tankers in a manner that allows the ships to be returned to a point of origin or another location with fresh water after some or all of a payload of LNG has been delivered. Thus, in various embodiments, a novel gas-water exchange system is provided. Accordingly, in various embodiments, re-filling even a portion of a LNG container with potable water can result in provision of a significant amount of highly demanded water to a point of origin or alternative location. As many LNG tankers currently deliver a payload and return empty, re-supplying such vessels with water not only provides economic viability for an otherwise empty return voyage, but also increases the ship's ballast and fuel efficiency.

In one embodiment, one or more bladders are provided wherein the one or more bladders are adapted to be placed within an emptied volume of a standard shipping container or an oil/LNG shipping container (i.e., tank, hull, etc.) and further filled with water to provide ballast and/or valuable shipping contents for a return or additional voyage. In one embodiment, at least portions of the oil or LNG contained within an oil tanker or a LNG tanker are emptied or extracted at the appropriate location (e.g., a regasification plant or refinery). Thereafter, emptied portions of an oil or a LNG shipping vessel or container are provided with a liner or bag suitable for preventing or minimizing contamination from previously and/or contemporaneously stored gas. For example, various liners available from Fab-Seal Industrial Liners, Inc. may be provided to accommodate water to be stored within a LNG tank and isolate the water from various materials, gases, debris, etc. Liners suitable for use in some embodiments of the present invention include, but are not limited to, P.V.C. flexible membrane liner materials. In various embodiments, liners or bags may also be made of similar materials to the shipping container bags or very large bags towed by a ship.

In various embodiments, bags or liners for isolating water or liquids may be fabricated in any desired manner, including in a completely flattened conformation. For example, two sheets of fabric may be cut to the desired plan shape and joined at their adjacent edges by suitable means consistent with the material of construction. For example, heat welding or solvent welding may be used if certain polymeric materials have been employed as the substance coating the fabric. Sewing may be necessary in addition. It is possible that the overall cost of a bag may be reduced if the center section and the edges are fabricated separately, i.e., not the flattened conformation.

In one embodiment, internal surfaces or portions may be coated with various materials to prevent or minimize risk of cross-contamination. For example, various spray-coatings may be applied once a quantity of oil or LNG is emptied from a portion of the vessel to create a virgin surface for the holding and contacting with water or similar fluid cargoes. By way of example, industrial water-proof coatings provided by the Procachem Corporation may be provided to coat, cover, or seal a surface that was exposed to or in contact with oil or LNG so as to render the surface capable of accommodating water without significant risk of cross-contamination. In various embodiments, internal volumes of storage tanks or similar structures are coated with a layer of material, the layer of material comprising an appropriate thickness to substantially eliminate the risk of cross-contamination between a liquid or material to be stored and a liquid or material previously stored in the same tank. In various embodiments, the layer of material applied is not so thick as to substantially impact the overall internal volume of the container, tank, vessel, etc.

In one embodiment, one or more tank cleaning apparatus are employed to cleanse the inside of a container or tank. For example, various features as shown and described in U.S. Patent Application Publication No. 2009/0308412 to Dixon, which is incorporated by reference herein, may be employed to prepare various oil and/or LNG shipping tankers and similar containers for the transport of cargo other than oil and/or LNG.

Figure 18:
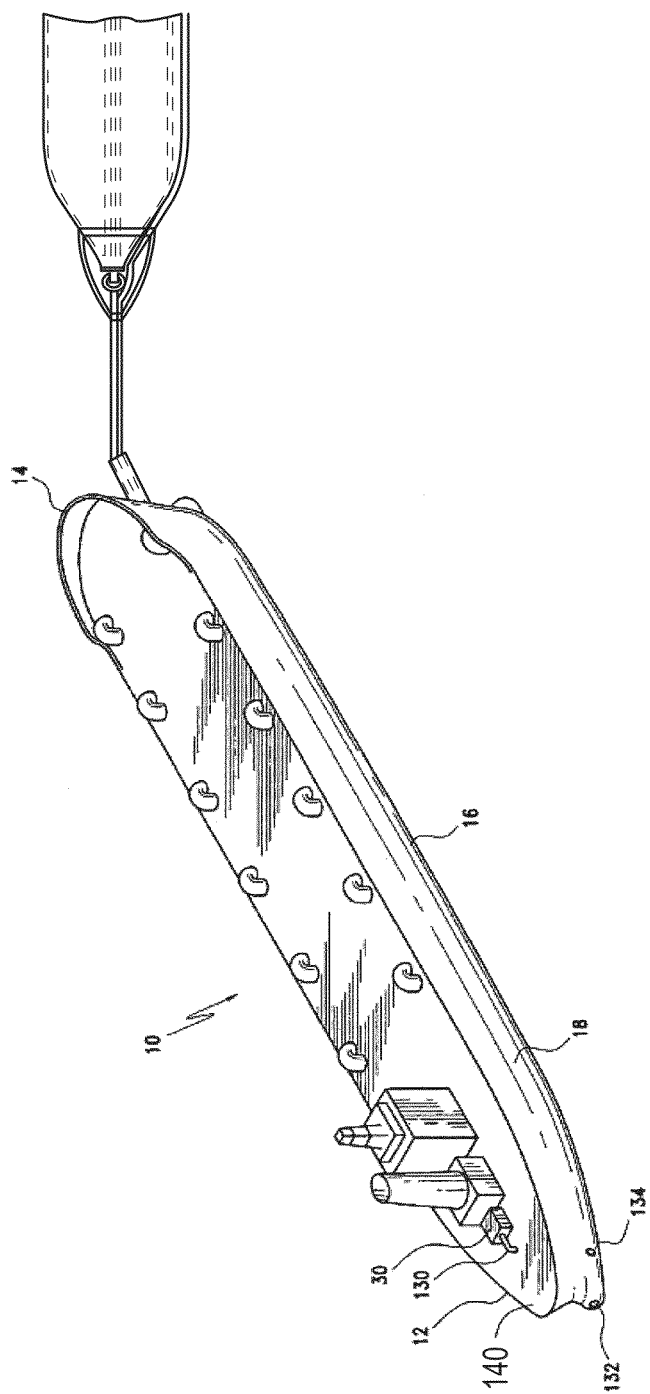
FIG. 18 is a perspective view of an oil tanker connected to a very large bag to facilitate transfer of water and ice therebetween in certain embodiments of the invention.

FIG. 18 is a perspective view of a ship connected to a very large bag to facilitate transfer of water there-between in certain embodiments of the invention. In one embodiment, the oil tanker will tow a very large bag full of fresh water. The fresh water may or may not be potable and ready for consumption upon arrival.

It is known that when pliable vessels are used to tow or transport volumes of water, wave propagation through the body of water and/or stored volume of water can present undesirable complications. Accordingly, various embodiments of the present invention comprise wave damping features adapted to reduce such effects. For example, wave dampening structures may be disposed within water containing vessels and/or positioned around water containing vessels of the present disclosure. Various devices and features described in U.S. Pat. No. 7,686,539 to Aristaghes, which is incorporated by reference herein, may be utilized with features of some embodiments of the present invention. Aristaghes discloses a water movement device comprising a flexible wall placed in water close to the surface, substantially vertically in a static rest state, made up of optionally perforated massive unit blocks assembled to one another in strings by cables on which said blocks are threaded or on which said blocks are crimped, said cables comprising: a series of cables disposed vertically side by side, parallel to one another, and a second series of cables disposed horizontally one above another and in parallel, and said vertical cables being suspended or tensioned at their top ends and/or respectively tensioned or moored at their bottom ends, and said blocks including empty orifices passing through them between the front and rear faces of said wall, and/or empty spaces between said blocks, such that said orifices and/or empty spaces between said blocks, if any, confer overall porosity on said wall lying in the range 5% to 75%, preferably 20% to 45%, of the area of the vertical section of said wall.

In some embodiments, bags of water similar to the towed bags are used in shipping crates and shipped. For example, both bags may be made of various materials. In some embodiments, the bags may need to be composed of a material that is UV, rot, microbial, and mold resistant.

In various embodiments, the bag is not a body of revolution or, in particular, tubular. In various embodiments, the top and bottom surfaces are indistinguishable and the bag or liner may be periodically turned over to equalize damage due to sun, weather, mold, aging, etc.

In various embodiments, liners of the present invention comprise a water-resistant, elastomer-coated mesh material, such mesh material being constructed of polymeric material having some inherent elasticity, such as polyester or nylon. A warp knit mesh construction is preferred in certain embodiments. The mesh material also may be steel mesh, preferably hexagonal netting of drawn steel wire or similar high modulus material, such as extended-chain crystallized polymer. In one embodiment, the bag is manufactured of a fabric structure (a plurality of separately formed layers bound together) for a flexible fluid containment vessel similar to the fabric structure described in U.S. Pat. No. 6,718,896 to Davenport, which is incorporated by reference herein in its entirety. In other embodiments, the bag is fabricated out of spirally wound strips of fabric having beam stabilizers, beam separators, and reinforcing similar to the fabric structure described in U.S. Pat. No. 6,675,734 to Eagles et al. and U.S. Pat. No. 6,860,218 to Eagles et al., which are incorporated by reference herein in their entireties. In alternate embodiments, the bag is fabricated out of fabrics and materials similar to those described in U.S. Pat. No. 6,739,274 to Eagles et al., U.S. Pat. No. 6,832,571 to Eagles, U.S. Pat. No. 7,024,748 to Eagles, U.S. Pat. No. 7,107,921 to Davis et al., U.S. Pat. No. 7,308,862 to Romanski et al., and U.S. Pat. No. 7,775,171 to Tupil, which are all incorporated by reference herein in their entireties.

In various embodiments, the base fabric is provided with an elastomeric coating for the purposes of providing waterproofing as well as protecting the material of construction from ultraviolet degradation and marine growth.

In some embodiments, the bags may include particular surface textures (either internally or externally or both) that may prevent undesired bacterial contamination of such surfaces. One particular aspect of various embodiments will, therefore, include a surface generally known as Sharklet™. Sharklet™ is the world's first technology to inhibit bacterial survival, growth, transfer and migration through pattern alone. The Sharklet surface is comprised of millions of tiny diamonds arranged in a distinct pattern that mimics the microbe-resistant properties of sharkskin. Sharklet is a simple, cost-effective solution for bacterial control. Sharklet is described in U.S. Pat. No. 7,347,970 to Kim et al., U.S. Pat. No. 7,143,709 to Brennan et al., U.S. Pat. No. 7,650,848 to Brennan et al., and U.S. Pat. No. 7,117,807 to Bohn, Jr. et al., the entire disclosures of which are incorporated by reference herein in their entireties. Sharklet is also described in U.S. Patent Publication Nos. 2010/0226943 to Brennan et al., 2010/0126404 to Brennan et al., 2010/0119755 to Chung et al., and 2011/0311769 to Chen et al. and International Patent Publication No. WO 2011/071892 to Magin, et al., the entire disclosures of which are incorporated by reference herein in their entireties.

In some embodiments, the bag may be composed of a self-healing material. One of the defining characteristics of living organisms is their inherent ability to repair physical damage. A growing trend in biomimicry is the creation of non-living structural materials that also have the capacity to heal themselves when cut, torn or cracked. Self-healing materials that can repair damage without external human intervention may give manufactured goods longer lifetimes and reduce the demand for raw materials, as well as improving the inherent safety of materials. Thus, a bag composed of a self-healing material can reduce leakage, water loss, and contamination.

In various embodiments, devices of the present invention comprise the ability to convert and/or utilize energy from naturally occurring resources such as solar, wind, wave, and thermal resources. In various embodiments, energy captured and/or converted from these sources may be used for various on-board functions, such as propulsion, heating, and various purification techniques.

In one embodiment, a vessel comprises photovoltaic arrays adapted for converting solar energy into forms of energy which may be used throughout the device and/or system. For example, solar energy may be captured, concentrated, and/or converted in a manner that allows for heating of a submerged volume of water (i.e. via thermal energy, electrical energy, or various combinations thereof) and the subsequent creation of convection currents throughout the system. The energy from the photovoltaic arrays may also be used to power the vessel or the vessel's navigating systems. Unlike the big, bulky, rigid solar panel units of U.S. Pat. No. 4,233,085 to Roderick et al., which is incorporated by reference herein in its entirety, the photovoltaic arrays should be lightweight and take up a minimal amount of space. Additionally, the solar energy collectors may track the movement of the sun along at least one axis and have a plurality of reflector panels similar to the solar energy collectors described in U.S. Pat. No. 7,932,461 to Johnson et al., which is incorporated by reference herein in its entirety.

In various embodiments, devices for towing water of the present invention comprise energy conversion means such as solar arrays for powering various devices. Devices of various embodiments of the present invention comprise towable bags or bladders with a surface of up to 60,000 square meters. As it is known that the power density of the sun's radiation on the surface of the earth is approximately 1.4 kW/m2, devices of some embodiments of the present invention are impacted by incredibly large amounts of energy. As such, it is contemplated that devices of various embodiments of the present invention comprise features for harnessing this energy, as well as additional sources of energy such as wind and wave action, to power various on-board features.

In various embodiments, organic thin-film solar cells for converting solar energy into forms of energy that may be used throughout the transport vehicle, bags of water, and/or system are provided in combination with a bag for holding and/or towing water. "Transport vehicle" as used herein refers to any vehicle for transporting items, e.g., ships, boats, trains, cars, trucks, semis/tractor trailers, planes, etc. Examples of thin-film solar cells are provided in U.S. Patent Application Publication No. 2012/0248878 to Iwanaga, the entire disclosure of which is hereby incorporated by reference. Thin-film solar cells are very light-weight and can be integrated into various materials. In some embodiments, light, flexible, thin-film organic solar cells are applied to one or more surfaces of the bags holding water. U.S. Patent Application Publication No. 2012/0312364 to Uhrich et al. describes an organic solar cell and is hereby incorporated by reference. Organic solar cells may be very thin and thus require little material and energy to produce, thereby reducing their environmental impact. However, any type of solar energy conversion means currently known or later invented may be used. Furthermore, known methods and systems for mounting the photovoltaic material on the shipping containers or bags of water may be employed, such as those described in U.S. Pat. No. 7,365,266 to Heckeroth, which is incorporated by reference herein in its entirety.

Organic solar cells may also be used to coat a wide range of surfaces, including the bags themselves and the shipping containers that hold the bags of water. Thus, the shipping container and/or the bag may be electricity-generating cargo. In some embodiments, the bag may be shipped in a shipping container without a lid. Thus, the top surface of the bag (the surface exposed to the sun light) may be coated with solar cells or photovoltaic films to generate electricity. In alternate embodiments, the lid of the shipping container may be clear or transparent so that the top surface of the bag (the surface exposed to the sun light) may be coated with solar cells or photovoltaic films to generate electricity. The terms "clear," "transparent" may be used interchangeably herein. Furthermore, in additional or alternative embodiments, one or more sides of the shipping container holding the bag may be transparent. A shipping container having one or more clear sides allows additional surfaces of the bag within that container to be covered with solar cells because the light can pass through the clear side to the solar cells. Thus, the sides of the bag proximate the transparent side of the container may be coated with solar cells to generate electricity from solar energy. Additionally, the shipping container may have clear sides and no lid so that solar cells or films may be placed on any side of the bag capable of receiving sunlight (i.e., the sides and top of the bag).

In some embodiments, the water bag may be transported in a transparent shipping container (i.e., four or more sides of the shipping container are transparent). In one embodiment, the container may not have a lid. In another embodiment, the container may have a lid. The lid may also be transparent or it may be opaque. One or more sides of the bag holding water may be covered with solar cells or solar film to generate electricity or useable energy from solar energy. Accordingly, if the bag is subjected to sunlight, then the bag may be UV resistant such that the bag does not degrade due to excessive exposure to sunlight. A UV-resistant material may not be necessary in embodiments where the bag is in an opaque shipping container.

One skilled in the art will recognize many benefits of using organic solar cells in embodiments of the current invention. For example, the ship or transport vehicles would be more efficient by reducing the dead-weight of stored fuel because the solar cells on the bags or shipping containers may generate some of the shipping vehicle's electricity. Other energy production requirements (e.g., electricity for the crew, such as lighting, power, air conditioning, heating, water heaters, etc., electricity for the communication systems, GPS, radar, sonar, etc.) are also reduced by use of electricity generating films applied to the bags' surfaces and structural surfaces of the containers. Electricity produced from solar energy may be used for any purpose on the transport vehicle, for example to run lighting, air conditioners, heaters, etc., to purify water for sailors' use, to power the ship's engines, to power GPS or sonar equipment, etc. In some embodiments, the shipping containers may be smart containers configured to transport the water bags, provide solar power, and have detectors to detect deviations in the cargo (e.g., temperature, leaks, etc.) or surrounding conditions (e.g., weather, GPS location, sun direction and intensity, etc.) similar to the smart containers described in U.S. Pat. No. 7,002,472 to Stratmoen et al., which is incorporated by reference herein in its entirety.

Organic electronics—a type of printed electronics—may be used in some embodiments to coat a wide range of surfaces. Organic electronics is the use of organic materials such as polymers to create electronic circuits and devices. In contrast to traditional (silicon-based) semiconductors that are fabricated with expensive photolithographic techniques, organic electronics can be printed using low-cost, scalable processes such as ink jet printing, making them extremely cheap compared with traditional electronics devices, both in terms of the cost per device and the capital equipment required to produce them. While organic electronics are currently unlikely to compete with silicon in terms of speed and density, they have the potential to provide a significant edge in cost and versatility. The cost implications of printed mass-produced solar photovoltaic collectors, for example, could accelerate the transition to renewable energy.

Using thin film solar cells on the bags and/or on the shipping containers reduces the need for large, bulky, heavy solar panels and solar panel support structures. Thus, the film solar cells save space and weight on board the transport vehicle.

Additionally, barrier films are contemplated for coating and protecting portions of bags in accordance with the present disclosure. Examples of such barrier films include, but are not limited to backing films with inorganic barriers, such as those disclosed in U.S. Patent Application 2011/0303277 to Neumann, the entire disclosure of which is hereby incorporated by reference in its entirety. For example, it is contemplated that a bag or water container of the present disclosure further comprises a barrier foil, comprising: a weathering-resistant protective layer and a backing layer comprising a barrier layer, wherein the protective layer is weathering-resistant, and wherein the barrier layer, comprising at least one inorganic oxide, improves a barrier effect with respect to water vapor and oxygen.

Long-promised technologies for the capture and underground sequestration of carbon dioxide have yet to be proven commercially viable, even at the scale of a single large power station. New technologies that convert the unwanted carbon dioxide ($CO_2$) into saleable goods can potentially address both the economic and energetic shortcomings of conventional CCS strategies. One of the most promising approaches uses biologically engineered photosynthetic bacteria to turn waste $CO_2$ into liquid fuels or chemicals, in low-cost, modular solar converter systems. In some embodiments, these systems could be employed on a transport vehicle such that the bags contain photosynthetic bacterial to turn waste $CO_2$ from the vehicle's engine to supply lower carbon fuels to the vehicle's engines. Thus, the $CO_2$ sequestration system may be a closed loop system on the vehicle to reduce the amount of fuel needed for the journey and to reduce the environmentally harmful impact of traveling long distances.

In one embodiment, natural sources of energy are harnessed to power various functions such as moving and/or circulating water through a water bag, forming an electric barrier around the bag to deter various creatures, powering lighting elements, GPS units, and rudders, and even providing propulsion for the towed bag device itself. It is further contemplated that power systems aboard a towing device (e.g., tug boat) may be synced with powered devices of a bag unit so as to supplement one or the other. In further embodiments, wind energy may be harnessed to move the bag or vessel through the use of towers, sails, windmills, etc.

In various embodiments, bags of the present invention are provided with dispersion means for repelling various creatures such as birds, seals, sea lions, whales, mussels, mollusks, octopi, and various other marine and avian creatures. Various creatures and sea life can produce serious detriment to bags and/or to ecosystems to which they may be transported in the event that they use the bag as a "host." Accordingly, in order to solve the long-felt need of repelling such life forms from towed bags, the present disclosure provides electrically powered means for dispersing such creatures. Such electrically powered means may be powered by various on-board energy devices as discussed herein or may derive power from elsewhere, such as an attached vessel. In one embodiment, features are provided along a surface of the bag to repel various creatures. For example, in one embodiment, a plurality of sprinklers is provided to prevent fowl from congregating on a bag and compromising the hygiene of the same. In another embodiment, flashing or strobe lights are provided to prevent unwanted creatures from inhabiting devices of embodiments of the present invention.

Another aspect of the present embodiment also includes loading tankers with water through very large bags of water. These bags of water may be brought to where the tanker has unloaded its cargo. Alternatively, these "water islands" can be positioned at various predetermined locations and after a tanker has delivered its cargo, it can then travel to one or more water islands to then take water on-board and then continue to a destination where such water is desired. The water may also be loaded through buoys or filled by lighters, which are smaller tankers. These loading techniques significantly reduce the cost of loading the water because it minimizes the large tankers' travel. For example, U.S. Pat. Nos. 7,841,289 and 7,500,442 to Schanz, which are hereby incorporated by reference in its entirety, discloses water transporter and storage systems for liquids, such as water, by means of a very large bag-like structure. In various aspects of embodiments of the present invention, methods and systems employ a lightweight towed submerged water transporter and storage system for liquids, which employs a streamlined towable hull with optional air and liquid storage bladders used not only to adjust buoyancy, but to allow the simultaneous transport and storage of different solids and liquids.

In one embodiment of the present invention, the ice itself may be transported to an agreed upon location. In such embodiment, ice in the required volume and having the desired characteristics, would be removed from the glacier or ice cap, and transported directly to the agreed upon location. Transport of such ice could be achieved in several ways. For example, the ice could be allowed to melt during transport such that upon arrival, it is in a liquid form and ready for consumption. Alternatively, the ice could be kept frozen such that it arrives at its final destination in its original form. Such transportation can be achieved using technology known to those in the refrigeration arts.

In one embodiment of the present invention, the water is transported to a different geographical location than where it is sequestered, without affecting the characteristics of the water. In one embodiment, the water is transported at least 10 miles, at least 250 miles, at least 500 miles, at least 1000 miles, or at least 10,000 miles, from the location where it is sequestered. Such distances can also be measured using kilometers, nautical miles, and the like.

According to various embodiments of the present invention, tankers can also be used to transport water of the present invention. Ballast space, cargo space, or combinations thereof can be utilized. When a vessel's cargo hold is empty or partially empty, the vessels use ballast water weight to maintain stability to compensate for a lack of cargo weight. The vessel is equipped with ballast tanks that can be filled with water (typically sea water for ocean going ships and tankers) to maintain stability when the vessel travels empty. The ballast tank water is then typically discharged when the cargo, such as oil, is loaded. By way of example and in further support of the present disclosure, U.S. Pat. No. 7,381,339 to van Leeuwen, which is a CIP of issued U.S. Pat. No. 7,273,562 to Robinson, which is a CIP of issued U.S. Pat. No. 6,869,540 to Robinson, are all incorporated herein by this reference in their entireties.

By way of example and in further support of the present disclosure, U.S. Patent Application Publication No. 2011/0036919 to Baird is incorporated herein by reference in its entirety. In one embodiment, water is used as ballast water weight in a large sea vessel, such as an oil tanker. After the oil tanker unloads its oil cargo at its destination, water is injected into the vessel's ballast tanks, the water is fully or partially treated, and the water is unloaded at the vessel's oil-loading port for human use, irrigation purposes, or other use requiring such water. In the present embodiment, the water is not released into the port, but rather the water is unloaded for use on land or onboard other ships, thus solving the problem of discharging non-native microorganisms and bacteria into the port's water. Furthermore, the water loaded into the ballast tanks can be either drinkable or undrinkable water. Either way, one skilled in the art can imagine different embodiments for treating the ballast water: the water can be treated while the tanker is in route, upon the tanker's arrival but before the water is unloaded, or the water can be treated once on land.

Figure 19:
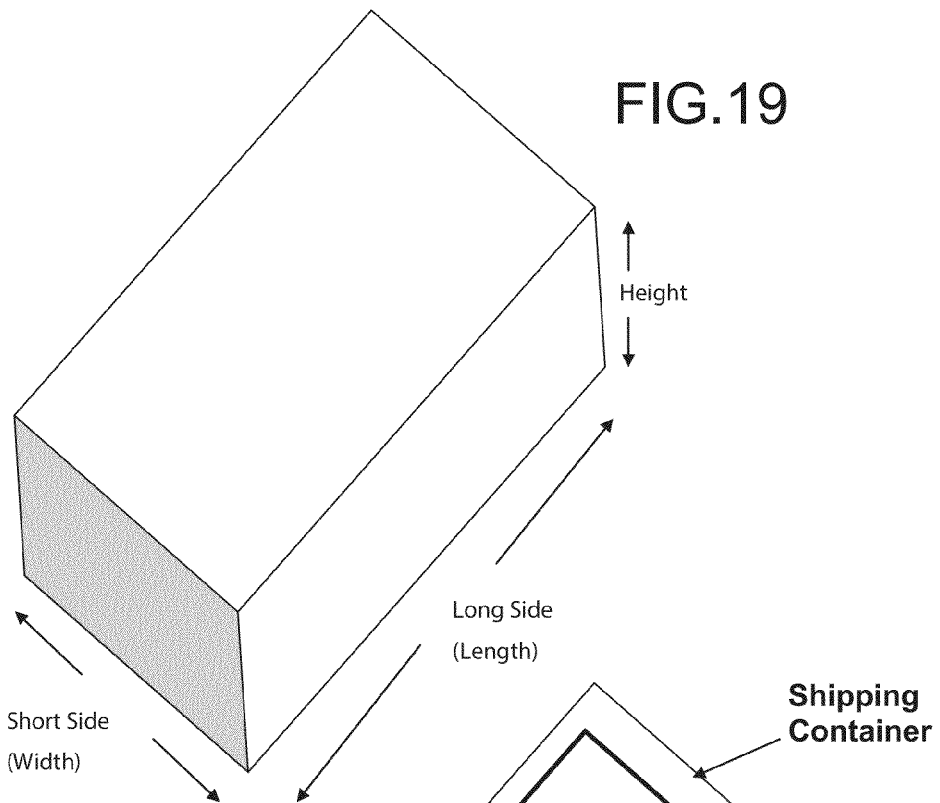
FIG. 19 is a perspective view of a shipping container.

There are over 17 million shipping containers in the world and shipping containers are known to travel via ship, train, and truck. The shipping containers (also called "intermodal containers," "containers," "freight containers," "ISO containers," "hi-cube containers," "boxes," "corner boxes," and "sea cans") may be traditional 10-foot, 20-foot, or 40-foot long shipping containers, such as those made by Aztec Container or BSL Containers Manufacturer, or any other sized shipping container. FIG. 19 shows that shipping containers generally have a long side (the length), a short side (the width) and a height. Shipping containers are traditionally of the dimensions 20 ft×8.5 ft×8 ft or 40 ft×8.5 ft×8 ft, but any size shipping container may be employed by embodiments of the present invention without diverging from the present disclosure. Shipping containers are often made from 6' to 8' gauge steel, but any gauge steel may be used. These mega-sized storage units are built to endure the perils of shipping, which makes them the reliable and secure for shipping water. Shipping containers are also strong; therefore, they are capable of holding heavy water, which weighs approximately 8.3 pounds per gallon and 62.4 lbs per cubic foot.

It is another aspect of embodiments of the present invention to stack shipping containers holding the bags of water on a ship in a similar manner to how shipping containers are traditionally stacked and loaded onto ships or other transport vehicles. Thus, on each of its eight corners the shipping container may comprise a corner casting and/or a simple twistlock fitting for stacking. If the container has both the corner casting and the twistlock, then the twistlock may be done through a larger oval hole on the bottom. Additionally, the shipping containers may be loaded onto a transport vehicle using a crane, reach stacker, or other known loading device (e.g., a fork lift).

An intermodal container is a standardized reusable steel box used for the safe, efficient and secure storage and movement of materials and products within a global containerized intermodal freight transport system. "Intermodal" indicates that the container can be moved from one mode of transport to another (from ship, to rail, to truck) without unloading and reloading the contents of the container. Lengths of containers, which each have a unique ISO 6346 reporting mark, vary from 8 feet (2.438 m) to 56 feet (17.07 m) and heights from 8 feet (2.438 m) to 9 feet 6 inches (2.9 m). There are approximately seventeen million intermodal containers in the world of varying types to suit different cargoes. Aggregate container capacity is often expressed in twenty-foot equivalent units (TEU) which is a unit of capacity equal to one standard 20 ft×8 ft (6.10 m×2.44 m) (length×width) container. For air freight the alternative and lighter IATA-defined unit load device is used. Traditionally, non-container methods of transport include bulk cargo, break bulk cargo and tank cars, tank trucks or oil tankers used for liquids or gases. This traditional idea thus teaches away from some embodiments of the present invention.

Figure 20:
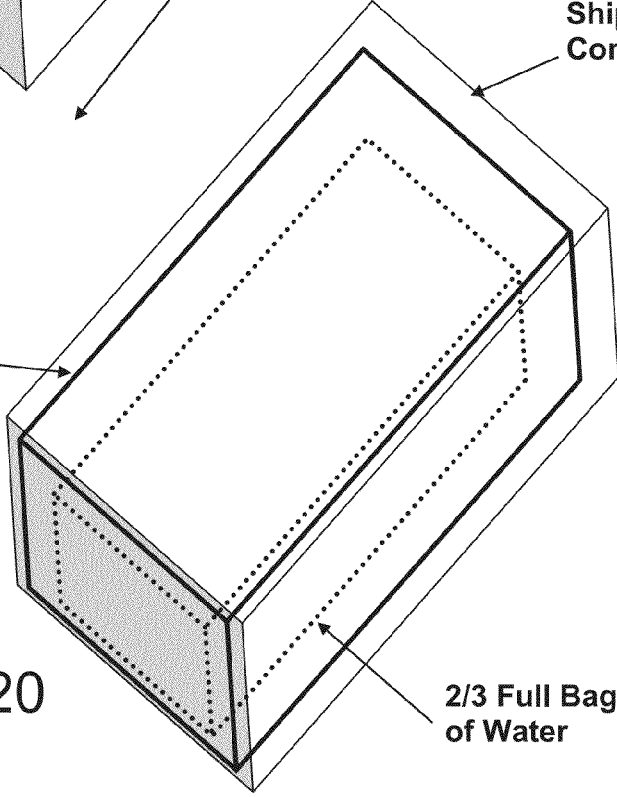
FIG. 20 illustrates a shipping container with a bag of water and/or ice.

It is one aspect of embodiments of the present invention to provide a method and system of transporting water in bags on various modes of transportation (e.g., ships, trains, planes, trucks, and tractor trailer trucks, etc.). In some embodiments, the bags of water are transported in shipping containers. See FIGS. 19 and 23-25 for various embodiments of shipping containers. FIG. 20 shows a shipping container (thin line outline) with different sized or filled bags of water in the shipping container. One bag shown in FIG. 20 (thick line) is substantially full and comprises much of the space in the shipping container. The other bag in FIG. 20 (dotted line) shows a bag that is only ⅔ of the way full with water. Thus, the volume of the water is equal to approximately ⅔ of the volume of the shipping container. In one embodiment, if the shipping container is only ⅔ full of water, then the remaining ⅓ of the shipping container may be filled with a layer of air or other gas to either add some pressure above the water without adding much weight or to impart a sterilizing influence over the water to preclude bacterial or mold growth.

Figure 21:
FIG. 21 shows a ship with shipping containers.
Figure 22:
FIG. 22 shows a ship with shipping containers.
Figure 23:
FIG. 23 shows one embodiment of a shipping container.
Figure 24:
FIG. 24 is a second embodiment of a shipping container.
Figure 25:
FIG. 25 is a third embodiment of a shipping container.

It is a natural extension of trading water that the water will need to be stored and transported to the place where it is needed. Details of such transport may or may not be part of the exchange between the entities. Alternatively, the details of transport may be decided entirely by the entity holding title to the water. Transport of the water can be made using any means suitable for transporting the water without affecting the quantity and/or characteristics thereof. Examples of water transport devices include, but are not limited to, trucks, planes, trains, ships, pipes, aqueducts, and bags (e.g., see FIGS. 21-22).

In various embodiments, non-rigid structures are utilized to store, transport, and/or convey volumes of water. In furtherance of the present disclosure, the following references are incorporated by reference herein in their entireties: U.S. Pat. No. 7,500,442 to Schanz, U.S. Pat. No. 6,047,655 to Cran, U.S. Pat. No. 6,330,865 to Cran, U.S. Pat. No. 6,550,410 to Reimers, U.S. Pat. No. 5,488,921 to Spragg, U.S. Pat. No. 6,293,217 to Savage et al., and U.S. Pat. No. 5,197,912 to Lengefeld. In various embodiments, non-rigid structures adapted to contain water are utilized to store, transport, and otherwise accommodate water.

It is a further aspect of various embodiments of the present invention to ship water in bags in shipping containers with various door configurations. Thus, in one embodiment, the shipping container may have one or more doors on the top of the shipping container. In another embodiment, the shipping container may have one or more doors on one or more sides of the shipping container (e.g., see FIGS. 23-25). The shipping container may have one or more doors on the short side that opens to the left or right or the shipping container may have one or more doors on the short side that opens upward or downward. In one embodiment, the shipping container may comprise a folding reinforcement panel to assist in filling the flexible container with water such as is described in PCT Patent Publication No. WO 2010/063135, which is incorporated by reference herein in its entirety. In further embodiments, the container may not have a door at all and may instead have an open top that is covered with a canvas or tarp. Thus the canvas or tarp is removable.

Shipping water in bags in shipping containers rather than wine or other liquid has its advantages. First, the water has fewer issues with spoilage than wine or other liquids. Plus, if a bag of water ruptures and/or leaks, there are fewer cleanup issues that there would be if a bag of wine ruptured or leaked.

In one embodiment, the bag has compartments, similar to the tank on a truck transporting gasoline, so that when the bag is in a shipping container on a truck or train and the truck or train goes around a curve, all of the water does not slosh to one side and tip the truck or train over.

In various embodiments, the bags of water in the shipping containers are only filled approximately two-thirds of the way. Thus, if the bags are sized to fill a shipping container, then other items may be shipped in the containers with the ⅔ full water bags because the bag will only take up about ⅔ of the space in the shipping container. Alternatively the bag may be sized larger than the shipping container such that when the bag is filled ⅔ of the way full, the water bag encompasses most of the space in the shipping container.

In some embodiments, the bag is put into the shipping container and then is filled with water once it is in the shipping container. In one embodiment, the bag is filled at the primary source of water. For example, the bag may be filled at a glacier. Thus, the water will be sourced directly from the catchment points of streams and rivers fed from glacier water melt, but the water may not be exclusively from the catchment points. In another embodiment the bag is filled with reserved water from the source at an intermediate port. In this embodiment, the bag in the shipping container may be filled after the bag and shipping container are on the boat if the boat is in a remote location and the port does not have mechanisms available to load a fully loaded container onto the boat. When mechanisms are available to load full containers onto the boat, then the bag may be filled before it is on the boat and be stock-piled for shipping. Other embodiments may partially fill the bag with water before the bag is placed into the shipping container.

In some embodiments, the water is put into the bags at very cold temperatures (typically below 10° C.) and because the bags of water have large masses, the water in the bags remains cold (typically below 10° C.) throughout the lifecycle of the water (i.e., until the water is removed from the bag for human consumption). In one embodiment, the bag is filled with glacial water, which is very cold (between 0° C. and 8° C.). In another embodiment, the bag is filled with glacial ice, which may melt during the bag's transport to its final location. In a preferred embodiment, the bags are filled with 4° C. water and the water is removed from the bags at a temperature of 8° C. or less. In additional embodiments, the cold bags of water in shipping containers are used as large refrigerators such that fruit and other items that should be refrigerated while shipped may be placed within the shipping container with the large bag of cold water. However, if the bag of water is filled to the shipping container's maximum permitted weight, then additional items like fruit, cheese, etc. may not be permitted to be added into the shipping container.

In one embodiment, a 20 ft or 40 ft portable refrigerated container may be used for cold storage. These refrigerated storage containers may be used as a freezer or refrigerator to keep the water and possibly other items cold. Additional insulation may be added to the shipping container to keep the water cold. In some embodiments, to allow airflow under and around the stored water and for added strength, aluminum t-bar floors may be used in the storage containers. EP Patent No. 0832826 to Clarke & Fisher, which is incorporated by reference herein in its entirety, discloses a refrigerated container with controlled air distribution. Other known refrigeration systems may be used, such as those described in European Patent No. EP 0203477 to Nagata et al., which is incorporated by reference herein in its entirety. Systems such as those described in European Patent Application Nos. EP 1637819 to Asteberg and EP 2499212 to Shiflett, et al. and PCT Patent Application No. WO 2011/124222, which are incorporated by reference herein in their entireties, may also be employed.

The idea of insulating the shipping containers comprising cold items (such as the large bags of water), however, teaches away from the idea of the refrigeration cave comprised of standard shipping containers with large bags of very cold water. In some embodiments, the water may also include ice or dry ice may be added to the container outside of the bag of water to keep the water cold. Additionally, in one embodiment, shipping containers are comprised of a material that dissipates heat or cold (e.g., the cold temperatures of the water) rather than insulating and keeping the cool temperatures in the shipping container like typical refrigeration shipping containers do. In this embodiment, the shipping container may be comprised of a material that conducts more heat than the standard shipping container. In some embodiments, the shipping containers may contain vents, channels, or holes to allow the cold air proximate the bags of cold water to flow out toward the refrigeration cave or toward other shipping containers requiring refrigeration. One embodiment may require loading and arranging the shipping containers in such a way that a substantial number of the vents, channels, or holes are in fluid communication with vents, channels, or holes of adjoining shipping containers, so that gases flowing within the enclosed space of the cold water container can pass freely to the shipping containers requiring refrigeration, such as is described in European Patent No. EP 0855012 to Van, which is incorporated by reference herein in its entirety. In one embodiment, the shipping container may comprise one or more fans to use convection to distribute the cold air away from the bags of water to the refrigerated items quickly and evenly. In another embodiment, at least one shipping container forming the refrigeration environment (e.g., one shipping container in adjacent to the shipping container requiring refrigeration) may be insulated to maintain cold temperatures in the refrigeration environment.

Figure 26:
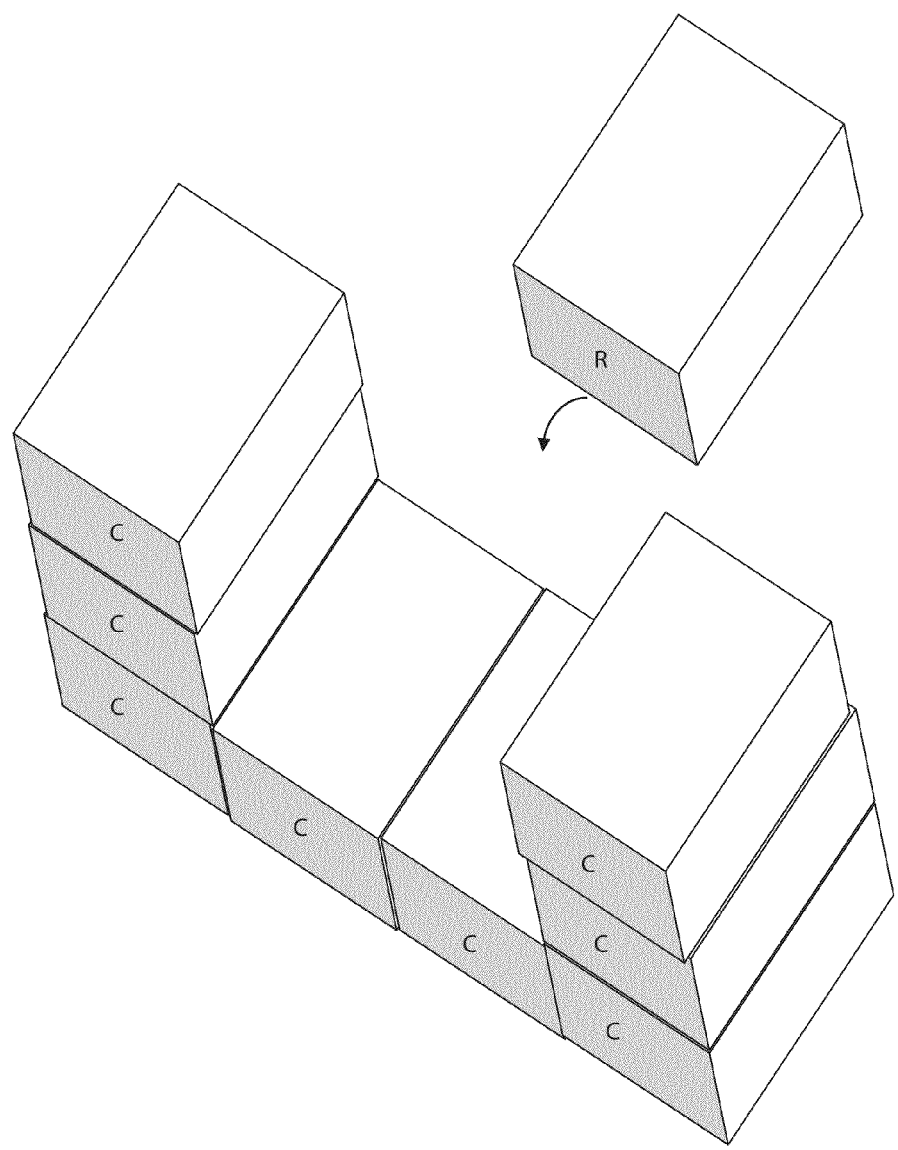
FIG. 26 is one embodiment of a refrigeration cave.

One commercially beneficial aspect of the large bags of very cold (less than 10° C.) water is that they remain cold after traveling large distances without insulation or other refrigeration techniques. Refrigerators are typically kept at 4° C., which is also the temperature of the bags of very cold water in one embodiment. Thus, the large mass of very cold water can be harnessed to create a refrigeration cave: a cave or space surrounded by shipping containers with bags of very cold water. Accordingly, a ship can charge reduced refrigeration prices to merchants wanting to transport their perishable goods in a refrigerated environment. Surrounding a shipping container requiring refrigeration with shipping containers full of very cold water would create a buffered environment with more gradual and reduced temperature oscillations. This buffer could reduce energy costs associated with keeping a refrigerated container cold. Additionally, the merchant shipping the very cold water may be charged reduced shipping costs because his very cold water is providing others with refrigerated environments. Referring to FIG. 26, the shipping containers containing a cold mass (e.g., very cold water) are labeled C. In the embodiment shown in FIG. 26, the refrigeration cave comprises multiple shipping containers with cold cargo C across the bottom layer of the cave and multiple shipping containers with cold cargo C along the sides of the cave. The shipping container requiring refrigeration is labeled R.

Figures 27, 28:
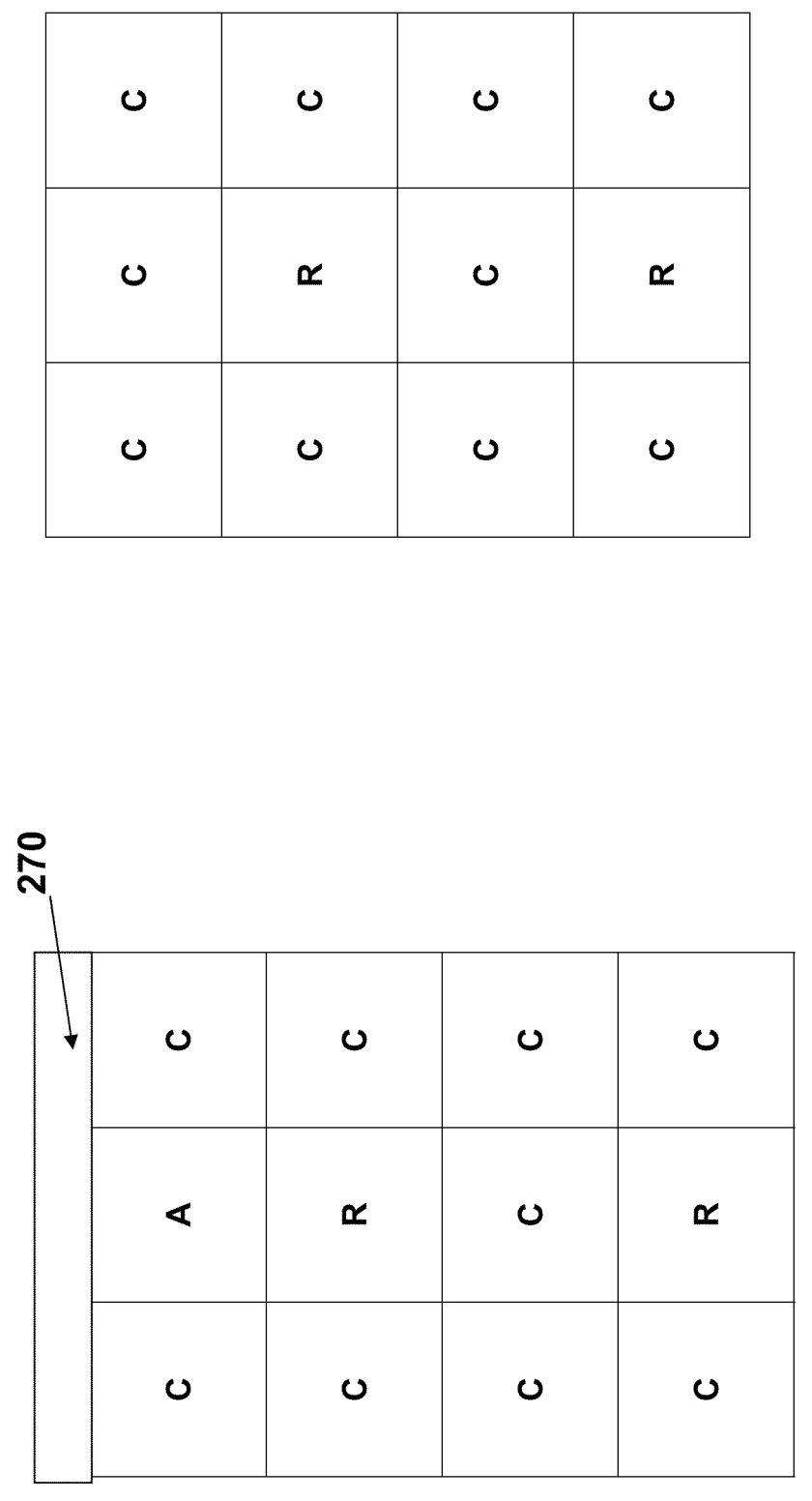

FIG. 27 shows a front elevation view of one embodiment of the refrigeration cave. The cave may comprise shipping containers containing a cold mass C (e.g., very cold water) around a perimeter of the cave. The cave may have one or more shipping containers requiring refrigeration R surrounded by shipping containers containing a cold mass C. In additional embodiments, the shipping container requiring refrigeration R may have an empty area A (e.g., just air) above the container acting as an insulator. Further, the shipping container comprising refrigerated items R may have a space blanket or other material 270 over the top of it or over the top of the air insulator A to reflect sunlight and keep in the cold temperatures.

FIG. 28 shows a front elevation view of another embodiment of the refrigeration cave. The cave may comprise shipping containers containing a cold mass C (e.g., very cold water) around a perimeter of the cave. The cave may have one or more shipping containers requiring refrigeration R surrounded by shipping containers containing a cold mass C. Specifically, the cold mass shipping containers may be placed above the shipping containers requiring refrigeration because cold air typically sinks, thus the cold air from the cold shipping containers will sink down to the shipping containers requiring refrigeration.

Figure 29:
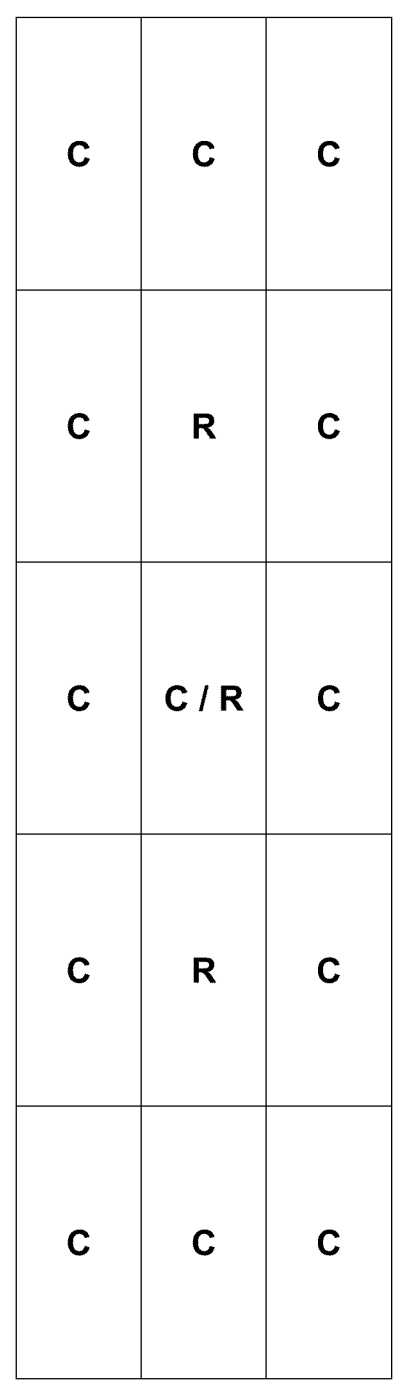

FIG. 29 is a top plan view of one embodiment of the refrigeration cave. Shipping containers comprising cold masses C (which may be very cold water in one embodiment) may make up the perimeter of the cave. Shipping containers requiring refrigeration R may be completely surrounded by shipping containers comprising cold masses C. Alternatively, all of the interior shipping containers may comprise items requiring refrigeration R.

U.S. Patent Publication No. 2008/0203093 to Skulnick, which is incorporated by reference herein in its entirety, discloses a shipping container with at least one sacrificial plug in a side of the container. At least one vent may be located in a second side of the container. The at least one sacrificial plug and/or the at least one vent is/are suitable for allowing water to enter into and/or air to exit out of the sea container. The at least one sacrificial plug and/or vent may be a pressure-sensitive sacrificial plug. Alternatively or in addition, the at least one sacrificial plug and/or vent may be dissolvable (e.g., dissolvable in water). Thus, when such sea containers fall off of a ship, they may provide a suitable window for recovery but also reduce the likelihood that damage will be done to other ships.

In various embodiments, the water is transported in a bag in the shipping container. The bag may be sized such that it fits within the specific shipping container used. For example, a 20-foot long bag may be used in a 20-foot long shipping container. In one embodiment, the bag is similar in characteristics to the disposable and reusable bladders made by Flexitank (Australia) Pty Ltd (sold under the name ContainerPac™ flexitank)—which are designed for bulk liquid transport. ContainerPac™ flexitanks can be installed by two people into a 20 ft dry sea container (which must be rated to 30 tonne, be less than three years old and lined with corrugated cardboard). ContainerPac™ flexitanks enable the container to transport bulk liquids up to and including 24 tonne. In other embodiments, the bag may have similar qualities to the large bag of water towed by a ship and described herein.

Thus, in one embodiment, the bag may be manufactured of a similar material to the towed bag. In another embodiment the bag may be manufactured of a similar plastic material to the ContainerPac™ flexitanks. In yet further embodiments, the bag may be manufactured of a similar plastic material to the Full-Pak flexitanks.

In some embodiments, different sized bags are used. Multiple smaller bags may be placed in a shipping container, for example if different types of water or water with different characteristics need to be shipped in one shipment but the purchaser does not want 24,000 liters of one specific type of water. Additionally the multiple bags may be held in crates or cardboard or metal or other material within the shipping container for ease of manipulation.

In various embodiments, the type, number, configuration, and system of valves; pumps; inlets; and outlets may vary. In one embodiment, a 2 inch or a 3 inch valve is used. In some embodiments a ball valve may be used to fill and drain the bag. Typically, the valves are metal or plastic, but valves of other materials may be used. A variety of bulkhead configurations may be employed to best accommodate the water being shipped. In one embodiment, a valve is placed on the side of the bag. The valve may stick out of the side of the bag or may be disposed within the bag. Further, the valves may be located on the outside of the bag in some applications and pushed into the bag for shipping and transportation. In another embodiment, the bags may be filled with water by using a product inlet entry point at the base of the bag located proximate to the shipping container door. The top of the bag may also have vents to allow for the displacement of air while the bag is being filled.

The valve may be used to fill and drain the water into and out of the bag. Other embodiments may locate the valve at different locations on the bag. Additional embodiments may include more than one valve. Some valves may be used only for filling the bag while other valves may be used to drain the bag. In one embodiment, a drain comprising a tube with perforations laid across the bottom of the bag (e.g., a French drain) is used to drain the water out of the bag. In other embodiments, if the valve is higher than the bottom of the bag, then a pump may be used to pump the water up to the valve.

In some embodiments, the inlet for filling the bag also serves as the outlet to drain the bag. Thus, the vents may allow for the intake of air while the bag is draining the water. Typically, the water outlets are gravity-fed so that a pump is not needed to discharge the water in the bag. The bags may be rolled to unload most of the water. In one embodiment, a pump may be used to pump water out of the bag. Specifically, pumps may be used for longer runs (i.e., tubing or pipes) or where the water needs to be moved uphill.

In various embodiments, the water bag may have one or more of the standard fitting options: a 2 inch (50 mm) male camlock with ball valve and dust cap (one piece construction); 3 inch (75 mm) male camlock with ball valve and dust cap (two piece construction); top fill and decant; top fill and bottom decant; and bottom fill and bottom decant.

The water bags may be supplied with a centrally located pressure relief valve to meet any OH&S standard around the world regarding the issue of having personnel in a confined space, especially once the water bag is full and ready for shipment.

In one embodiment, a channel welding system may be employed that allows the quality of each weld to be inspected before the next is started, ensuring the highest standards of quality are met with each bladder.

In some embodiments, the bags are reusable and thus in some distribution schemes the bags can be used for more than one filling cycle. The bags may also be recycled after they can no longer be filled and transported. Thus, in one embodiment, once a bag is no longer useable to transport water, the bag may be recycled and used to make water bottles. Specifically, portions of the bags that are HDPE or other recyclable plastic can be used in plastic bottles for water.

The bags may be foldable such that they can be folded and shipped back to the water source for refilling. Alternatively, the bags may be broken down into component materials for recycling depending upon the distribution scheme and distance from the water filling source.

It is another aspect of one embodiment of the present invention to provide a method of scheduling the shipping, storing, and delivery of the bags in the shipping containers. In one embodiment, the water bags are shipped in shipping containers when ships are not completely full, and, thus, the shipping price is reduced (i.e., the Expedia model of shipping water: ship when there is room and a discount). The water can be stored before and after it is shipped such that the time of the shipment either does not depend on the purchase date or only slightly depends on the water purchase date. Additionally, models could be used predict when and where will need water and water bags can be shipped to these locations before these locations actually purchase the water (i.e., war zones, the Middle East in the summer, hurricane season in the Caribbean and southeastern United States, the deserts of Chile in the summer, etc.). In one embodiment, the water is shipped in the shipping containers to certain locations when the currents favor shipping to that location, i.e., travel with the current to reduce fuel costs and thus shipping costs. In other embodiments, the timing of the shipping is dependent upon the urgency of the water delivery. If the buyer needs the water quickly, then the water will be shipped right away and the cost of shipping may be increased.

Yet another aspect of embodiments of the present invention is to provide a method of scheduling the shipping, storing, and delivery of the water on boats of different types. Thus, shipping routes traditionally used by container ships may transport the water in a bag in a shipping container. Alternatively, shipping routes traditionally used by bulk carriers or oil tankers may transport the water in the cargo holds of the bulk carrier or oil tanker. The water source location and the water destination location will likely affect the type of boat/ship used to transport the water. A comprehensive map of global shipping routes may be used to determine the best route and type of boat. For example, the map developed by Pablo Kaluza, Andrea Koelzsch, Michael T. Gastner, and Bernard Blasius and printed in the Journal of Royal Society may be used, and is incorporated by reference herein in its entirety.

In some embodiments, known systems and methods to secure the bags and/or shipping containers onto their mode of transportation (e.g., ship, train, truck, etc.) may be used. U.S. Pat. No. 7,690,319 to Wingate, which is incorporated by reference herein in its entirety, discloses an anchoring system and method for docking and/or mooring vehicles, particularly watercraft and for restraining loads in truck beds or trailers. The apparatus utilizes ropes or cables in housing unit that provides for the extension and retraction of the rope or cables preferably without the need of electrical or manual cranks A method of providing restraining means to a container liner similar to the one described in PCT Patent Application No. WO 2012/020259 to Massie, which is incorporated by reference herein in its entirety, may also be used.

In some embodiments, the water bags reduce costs by eliminating and/or reducing return expenses. Plus, the water bags alleviate the need to clean the container. Accordingly, in one embodiment each bag may installed new to eliminate cross contamination problems and to ensuring the integrity of the water. In an alternate embodiment, the bags may be reused to transport the same type of water. Additionally, the water bags may be cleaned after each use to transport water of a different type or of the same type and to ensure that the water quality is not reduced due to contaminates such as bacteria, algae, mold, dirt, etc.

In some embodiments, the present invention utilizes existing systems and devices of water, liquid, and/or gas transport to convey or store water. For example, in various embodiments, devices and systems may be retro-fitted or reconstructed in such a way to safely and efficiently transport large volumes of water. U.S. Pat. No. 5,727,492 to Cuneo et al, U.S. Pat. No. 5,099,779 to Kawaichi et al., U.S. Pat. No. 7,451,604 to Yoshida et al., U.S. Pat. No. 4,224,802 to Ooka, U.S. Pat. No. 4,331,129 to Hong et al., and U.S. Pat. No. 6,997,643 to Wille et al., U.S. Patent Application Nos. 2008/0110091 to Perkins et al, 2005/0095068 to Wille et al., 2009/0126400 to Pozivil, 2005/0276666 to Wille et al., and 2008/0127654 to Darling et al. are incorporated by reference herein in their entireties.

One of skill in the art will recognize that where quantities of water are to be stored, degradation of water quality may become a concern. Accordingly, various embodiments of the present invention contemplate a device, which is adapted for preventing growth and propagation of mold, mildew, algae and other deleterious effects caused over time to a quantity of water.

In various embodiments, methods for maintaining purity and sterility of the water are provided. By way of example and to further provide support and disclosure, the following references are incorporated by reference herein in their entireties:

U.S. Pat. No. 7,731,847 to Huy discloses a submersible reverse osmosis desalination apparatus and method with a submersible desalination unit composed of a structure containing a water intake system for acquiring sea water, a sea water pre-filtration system for removing lager contaminants and debris, a reverse osmosis system for the purification of the water, a permeate transfer system to carry the water to where it will be used, a power source for powering the equipment used in the process and a control system that operates and monitors the equipment and process of removing salt from the water and transferring the desalinated water to other use and returning the brine solution to the sea.

U.S. Pat. No. 5,229,005 to Fok et al. ("Fok") discloses an ocean depth reverse osmosis fresh water factory. Further, Fok discloses a process for the desalination of sea water by lowering from a floating platform sets of vessels, which are constructed or laminated in part with reverse osmosis elements, into the ocean depth to extract fresh water. Thereafter, the fresh water filled vessel is to be lifted individually from the ocean depth by means of a mechanical lifting system to a predetermined elevation above the sea surface to facilitate the delivery of the extracted fresh water to a coastal water transportation system via a valve at the bottom of the vessel which is also connected to a water delivery pipeline.

U.S. Pat. No. 4,512,886 to Hicks et al. discloses wave-powered desalination of water using a device for the reverse osmotic desalination of water wherein the required energy is derived from waves.

For example, in one embodiment, ultra-violet light is periodically applied to stored quantities of water so as to neutralize or destroy various bacteria, viruses and protozoan cysts such as giardia and cryptosporidia.

These methods for maintaining purity and sterility of the water may be used with any embodiments described herein. For example, water may be purified or sterilized while being stored or transported in a large bag towed behind a ship, in a large bag in a shipping container, in a container on a train, in the cargo compartments on a ship, in the ballast compartments on a ship, in empty oil tanks on a train or truck, in empty oil tankers, etc.

In one embodiment wherein the water is shipped or stored in a large bag, such as a bag that fits in a shipping container, upon arriving at the water's final destination, the shipping container with the bag of water is unloaded. The bag and container may then be placed in a location where people can retrieve the water from the bag. Thus, in some embodiments, the bag just sits at its final destination and people walk up to the bag to get water from the valve in the bag. The container may provide extra support for the bag and may also protect the bag from the elements. In alternate embodiments, the bag may be unloaded from the container at its final destination. The bag may sit or be stored on its own (i.e., not in the shipping container). The bag may be placed in another container, on a shelf or support, in a cage, or in any other structure capable of holding a large, heavy bag of water. Additionally, the bag may have a support system built into the bag such that the bag can sit on its own and maintain a structured shape.

Thus, the water can be stored in the bags upon arrival at its destination. Typically, if the water bag is not stored in a shipping container, then the water should only be stored for 6 months in the large bag without any need to disinfect, clean, or purify the water. Some bags, however, when stored within a shipping container may allow the use of standard 20 ft containers with bladders to become medium to long term storage tanks at a quarter of the cost of more traditional bulk storage options. Some bladders, especially when stored in a container, can be stored above ground or below ground up to 5 years.

Ultraviolet technology and other purification methods known or described herein may be used with the water bags if the water is stored in the bag for long periods of time. UV purification can kill germs, mold, bacteria, etc. that may grow in the bags after long storage durations. Additionally, the water may be stored for longer periods of time if such purifications methods are employed. The UV purification methods may be employed on the water while the water is in the bag or the purification methods may be employed as the water is removed from the bags. Furthermore, if the water is stored for long durations and such purification methods are not available, then the water may be used for irrigation or construction purposes (i.e., purposes not requiring potable water) or the water may be put into the municipality's water treatment facility.

Emerging technologies offer the potential for significantly higher energy efficiency in desalination or purification of wastewater, potentially reducing energy consumption by 50% or more. Techniques such as forward-osmosis can additionally improve efficiency by utilizing low-grade heat from thermal power production or renewable heat produced by solar-thermal geothermal installations.

In some embodiments, a water purification system may be on board the ship such that the water in the bags—which may be in shipping containers in some embodiments—is purified while in route to its destination. In one embodiment, electricity produced from solar cells, solar films, and/or photovoltaic arrays on the bags or shipping containers is used to run the purification systems. Additionally, some bags may be empty while others are initially full of dirty or non-potable water. The dirty or non-potable water may be filtered and purified while on the ship and the clean/purified water may then be put into clean bags. Because the bags may be compacted and compressed, bringing additional bags on-board would not require a significant amount of space. Thus, some bags could be used for clean water and other bags could be used for dirty water and the bags could be reused as such.

In one embodiment of the present disclosure, the bags are filled with water after the bags are in the shipping container. In another embodiment, the bag is filled with water before the bag is placed in the shipping container. In various embodiments, the water is filtered and/or purified as the water is put into the bag. In other embodiments, the water does not need to be filtered or purified, so it can be put into the bag without any processing. In some embodiments, the water is filtered and/or purified as it is taken out of the bag.

In some embodiments, if a high grade of purity is required, the water may be filtered, ozonated, and/or UV treated prior to being placed in the bag. In one embodiment, the water is also filtered, ozonated, and/or UV treated after the water is removed from the bag for use. Ozone disinfection may continue to purify the water while the water is in the bag. In embodiments where a lower grade of water is desired, the water may be filtered for particulates above a certain size (e.g., 2 microns) and disinfected before being placed into the bag.

In one embodiment, a water storage device of the present invention is adapted for storage in a vertical manner (i.e. wherein a longitudinal axis of a bag is disposed substantially vertically and extending into a depth of a body of water). In this embodiment, the bag or vessel comprises various features for circulating or distributing water throughout. For example, features as described in U.S. Pat. No. 6,580,025 to Guy ("Guy") may be incorporated into storage and transportation devices of various embodiments of the present invention. Guy discloses an apparatus and method for thermoelectric heating and cooling a fluid and is incorporated by reference herein in its entirety. The device includes at least one thermoelectric module and at least one rotating heat sink that transfer heat between the thermoelectric module and the fluid. One of ordinary skill in the art will recognize that when a device is positioned generally longitudinally in a body of water, the lower regions of the device will be cooled due to the water at greater depths being of generally lower temperatures. Accordingly, a device stored longitudinally will generally adopt a thermocline similar to the body of water in which it is disposed, unless acted upon by additional forces/features. Therefore, in one embodiment, convection currents are induced within a water storage device by supplying, for example, thermal energy to a lower portion of the storage unit, thereby causing water in the lower portions of the device to heat, expand, and rise to the top, creating convection currents and reducing deleterious effects caused by allowing a volume of water to remain stagnant.

Figure 30:
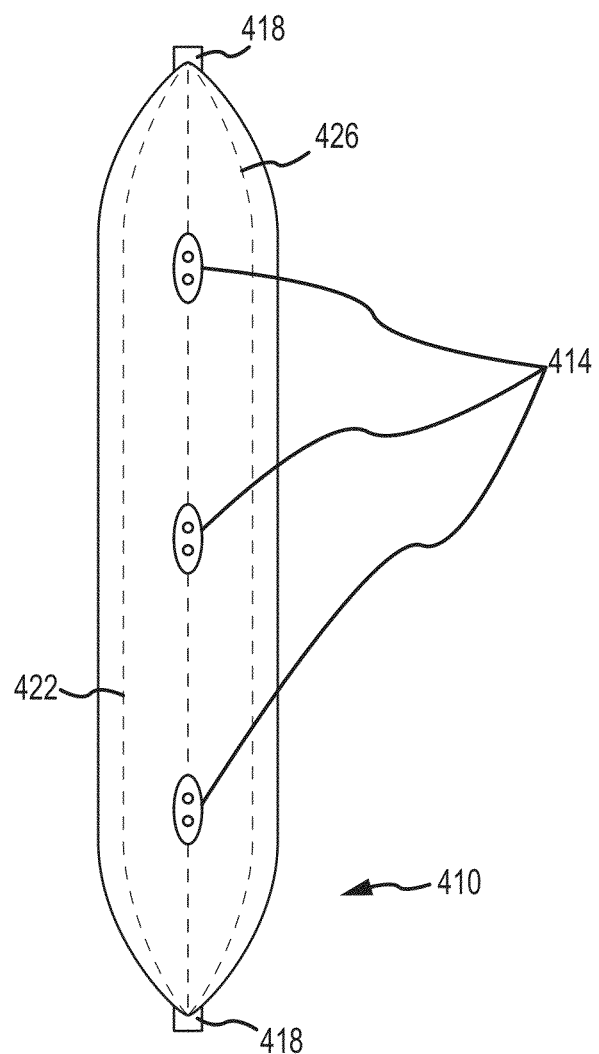
FIG. 30 is a top plan view of a towed vessel suitable for transporting liquids or ice according to one embodiment.

FIG. 30 depicts a towable vessel 410 for transporting fluent cargoes. Note that the towable vessel may also be called a bag, bladder, very large bag, or VLB herein. In one embodiment of the present invention, a towable vessel 410 may comprise a plurality of ports 414 suitable for the inlet and removal of fluids to be transported. One of skill in the art will recognize that a plurality of such ports may be useful in fluid removal operations, both as a means to increase the flow rate of fluid into a vessel 410 and/or to allow for air intake into one port 414 while fluid is extracted from another port 414. In some operations, it may be desirable to transport extremely large volumes of fluid. For example, it may be desirable to transport in excess of 35,000 tons of water in a single vessel 410. Accordingly, increased flow rates to and from a vessel may be desirable and stand to increase the overall efficiency of the system and fluid transport operations.

Vessels 410 of the present invention may be comprised of a variety of non-rigid, flexible materials including, but not limited to, urethane, polyurethane, urethane-coated polyesters, thermoplastic urethane coated nylon, vinyl, and other similar materials or various combinations of the same. Those of skill in the art will recognize the various advantages of constructing a vessel 410 of the present invention out of a flexible material, including, but not limited to, the ability to easily store and transport the towable vessel 410 when it is not in use for transporting liquids.

In one embodiment, a towable vessel 410 further comprises a reinforcing member 418 on at least one node or end of the vessel 410 for attachment to towing members and towing vessels. Reinforcing members 418 may be comprised of rigid structures fastened to or otherwise connected to a pliable or flexible container 422 and capable of withstanding various tension forces imparted to the vessel 410 during towing. Reinforcing members 418 may further be connected to reinforcing seams 426 which travel through a longitudinal length of a towable vessel 410. Reinforcing seams 426 may be comprised of a variety of known materials, including, but not limited to metal cables, nylon cords, plastics, and various other materials suitable for withstanding tensile loading. The reinforcing seams 426 may be positioned is specific areas and at specific angles relative to a horizontal plane and/or other reinforcing seams 426. In some embodiments, the reinforcing seams 426 are woven, similar to a seatbelt for an automobile or airplane. The reinforcing seams 426 may be woven such that there is no end of a reinforcing seam 426 to reduce fraying and weak points. Reinforcing seams 426 may transmit and resist forces applied to a towed portion of the vessel 410, thereby reducing unwanted deflection of the vessel 410 and associated drag on the vessel 410.

In an alternative embodiment, a towed vessel 410 comprises an ellipsoid shaped hull (when in a filled state) to reduce drag, at least one air chamber to maintain the vessel in an upright position, one or more ports 414 for filling and/or emptying the vessel, one or more removable bladders capable of containing and segregating different liquids or materials, and one or more devices capable of selectively controlling the amount of air within a portion of the towable vessel 410 and corresponding buoyancy.

It will be recognized that the shape of the vessel 410 may take various different forms, depending upon the desired quantity of fluid to be transported, characteristics of the vessel (s) towing the vessel 410, and other factors. However, it will further be recognized that it is desirable to reduce drag in water towing applications. Accordingly, it is known that drag on the vessel 410 will decrease as the wetted surface area and width of the vessel 410 decrease, and while length increases. Therefore, in order to improve towing efficiency, an optimal geometric design may be constructed.

Figure 31:
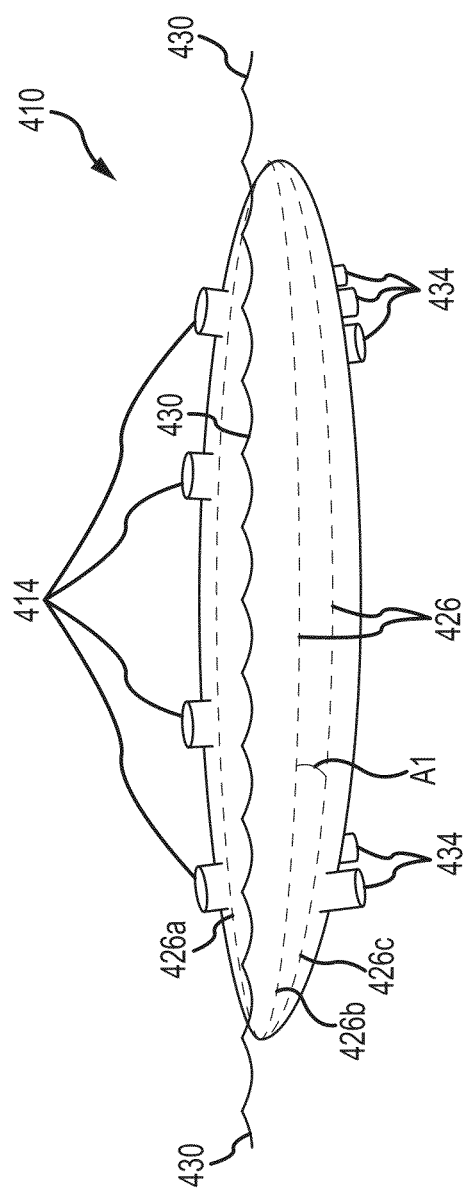
FIG. 31 is a side elevation view of a towed vessel suitable for transporting liquids or ice.

FIG. 31 depicts a side elevation view of one embodiment of the present invention with respect to a water line 430. In water towed operations, it may be desirable to adjust the buoyancy of the towable vessel 410, either due to various environmental conditions or based on the amount and density of the liquid contained within the vessel 410. Accordingly, the present invention contemplates operating a vessel 410 at various depths within a body of water. Variable buoyancy may be obtained, for example, through the use of a dorsal bladder (not shown) which contains air or a gas of lower density than a material to be towed, which both maintains the vessel 410 in an upright position and provides a certain amount of buoyancy relative to the vessel's surroundings. Alternatively, air or gas may be housed within a main portion of the device 410 to provide similar functionality.

In one embodiment, ports 414 include the ability to exhaust and intake air based on a desired level of buoyancy. For example, one or more ports 414 are equipped with means, such as reversible impellers to draw air in or exhaust air from a previously disclosed bladder or from one or more fluid containing compartments of the vessel 410.

Buoyancy may be adjusted, for example, when various environmental conditions change. In long-distance open-sea transit, it is known that temperature changes may occur in the surrounding waters. Accordingly, a fluid containing vessel 410 that has been towed in relatively cold waters for a length of time may obtain an increased density due to cooling effects from the surrounding water. When such a cooled vessel 410 reaches warmer waters, and particularly when there is an abrupt transition, the cooled vessel 410 may have a tendency to sink or reside lower in its surrounding water. To account for this, embodiments of the present invention comprise means for taking in additional air and increasing buoyancy. For example, ports 414 comprise manually activated or logic driven motors to adjust buoyancy while the device is in operation. A manually activated motor may be controlled from within a towing vessel or from another remote location and may allow a user to increase the volume of air contained within a vessel 410 based on the visual appearance of the vessel 410 or other indicia. Logic driven motors may be comprised of devices which sense one of: a difference between the temperate of water within the vessel 410 and the vessel 410 itself, a sudden change in the temperature of the water within which the vessel 410 is being towed, or the amount of submersion of the vessel 410 within its surroundings. For example, a sensor may be employed at a certain location of the vessel 410 which senses the presence of an unacceptably high level of submersion and triggers motor(s) within one or more ports 414 to intake air and thereby increase the buoyancy of the vessel 410.

It will be recognized that it is often desirable to prevent materials, such as rain, sea water, and other contaminants from entering the ports 414 and thus impacting the purity of water or fluids to be transported. Accordingly, the present invention contemplates means to secure the ports 414 when venting or adding fluid or gas is not desired. For example, covers suitable for preventing the unwanted entrance of materials may be selectively actuated, such as by a remote user. Alternatively, ports 414 for venting air may be connected solely to a bladder which is not interconnected to a main fluid containing portion of the device 410. In one embodiment, physical barriers may be constructed around ports 414 which allow for the entrance and exhaust of gas, but prevent the unwanted entrance of various fluids and contaminates.

In one embodiment, one or more one-way valves may be constructed on a portion of the vessel 410 that is to reside above the water line. One-way valves are known to those of skill in the art and may be provided to allow for the venting of gases, yet still prevent the unwanted entrance of other fluids or contaminants. For example, one one-way valve may be employed to allow for the release of air when less buoyancy is desired and another may be provided to allow for the opposite flow of air into a vessel 410 when greater buoyancy is desired. In one embodiment, one or more of these valves are selectively controlled by a user. In this manner, a user may have discretion as to when to insert air (i.e., a user may elect to insert air during optimal conditions when the risk of taking sea or rainwater is low) and/or remove air.

As shown, one or more fins or skegs 434 may be included on a vessel at a location below the water line 430 to increase directional stability of the vessel 410 while being towed. In one embodiment, one or more skegs 434 may be selectively controlled to assist in steering and/or maneuvering the potentially cumbersome vessel.

In one embodiment, the present invention comprises locating means. As will be recognized, submerged or partially submerged vessels may be difficult to identify, particularly in poor lighting conditions or at night. Additionally, it is a known risk that vessels 410 of the present invention and similar objects may become dislodged from their towing vessel. In such circumstances, these vessels 410 may pose significant safety risks. While it is an aspect of the present invention that damage to or loss of devices 410 of the present invention pose reduced risk to the environment, vessels 410 separated from their host or towing vessel may still pose a collision risk. Accordingly, a transmitting device, such as a Global Positioning System ("GPS") transmitter is incorporated into one embodiment of the present invention. The GPS transmitter may, for example, transmit the coordinates of a vessel 410 at specified temporal increments or when another related device requests such information. Additionally, other vessels or remote locations may be equipped with GPS sensing means to detect and convey the transmitted location of a vessel 410.

The vessel 410 may comprise reinforcing seams 426 that extend a longitudinal length of the towable vessel 410. In one embodiment, the vessel 410 may comprise an upper reinforcing seam 426a along the top of the vessel 410, an equatorial reinforcing seam 426b along the equator of the vessel 410, and one or more side reinforcing seams 426c either above or below the equatorial reinforcing seam 426b. The side reinforcing seam 426c may be an angle A1 away from the equatorial reinforcing seam 426b.

The towable vessel 410 may experience various forces on the front end of the bag when it is being towed. These forces may vary along the surface of the bag.

Figure 32:
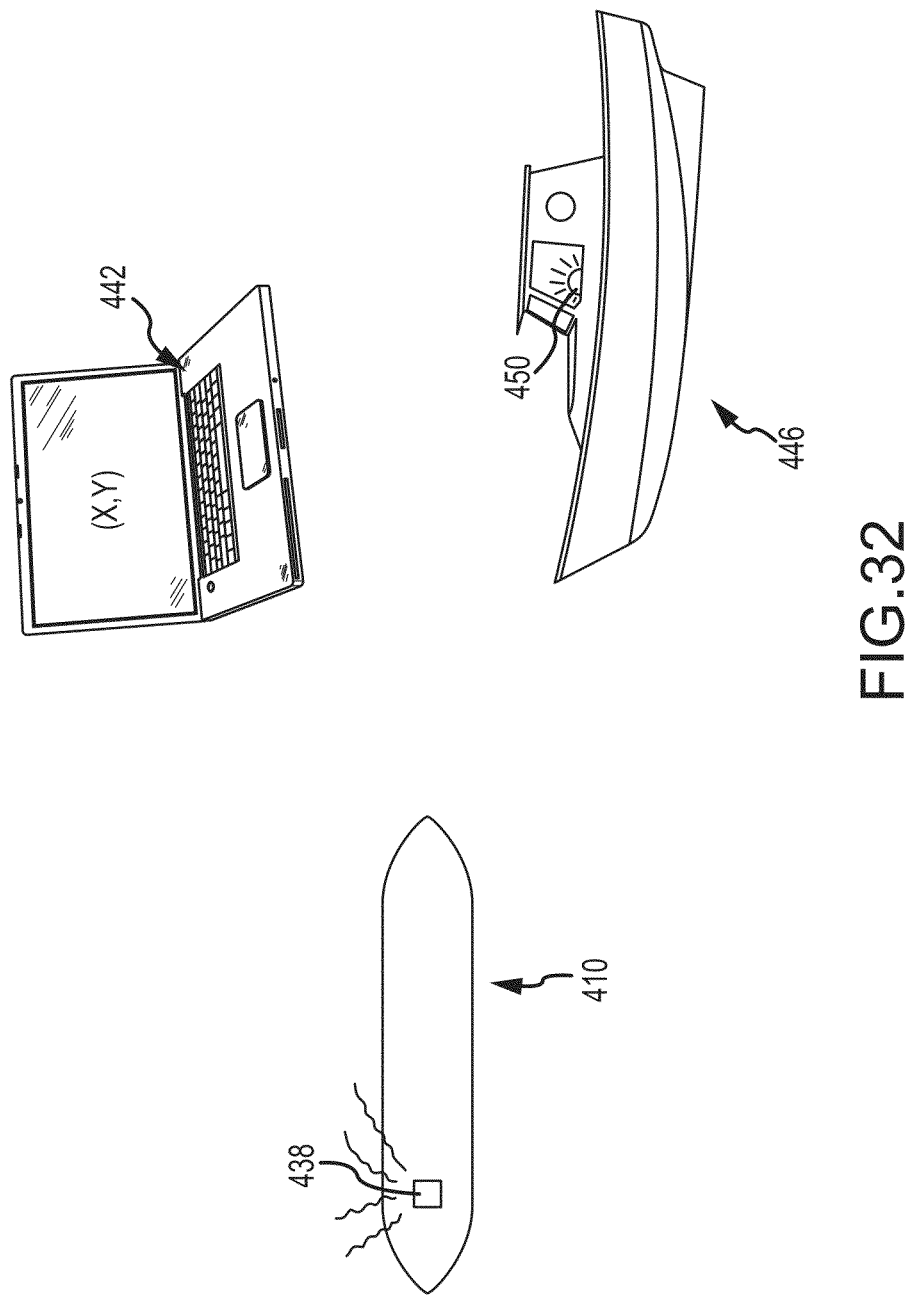
FIG. 32 is a diagram depicting various features of a towed vessel suitable for transporting liquids or ice according to one embodiment.

FIG. 32 depicts a towed vessel 410 for fluent cargo transport equipped with a GPS transponder 438. In one embodiment, the GPS transponder 438 may be activated remotely, such as when a towing vessel recognizes that it has lost contact with the towed vessel 410. In another embodiment, the towed vessel 410 may constantly transmit information regarding its own coordinates. For example, the vessel 410 may transmit information regarding its location at predetermined time intervals whether or not it is detached from a towing vessel. In yet another embodiment, a vessel 410 may transmit information regarding its location upon request (i.e., at the receipt of a signal from another location or device). Information regarding a vessel's 410 position may be transmitted to and received by various different locations and objects. For example, the signal and information transmitted by a GPS transmitter 438 may be obtained by a remote computing station 442 for processing and displaying the information. A remote computing station 442 may reside in a variety of locations, including on other vessels and various fixed on-shore locations. Information transmitted by a GPS transmitter 438 may also be received by various other vessels 446 potentially in the vicinity of the towed (or misplaced) vessel 410. Vessels 446 may be equipped with indicator means 450 capable of alerting crew members that a partially submerged object 410 is present in their vicinity and may pose a safety risk.

Various other advantages of equipping a vessel 410 with GPS locating means 438 will be recognized by those of skill in the art. For example, the status and progress of a fluid containing vessel 410 may be tracked remotely by interested parties to determine logistical information.

A vessel 410 may comprise visual indicia of its location and size, such as conventional lighting members positioned at various locations on the vessel 410. Additionally, given the significant width that floating vessels of the present invention may comprise, it is further contemplated that a vessel 410 may be equipped with port and starboard indicator lights to indicate the lateral boundaries of a vessel 410 (i.e., conventionally, green lights are used to indicate the starboard side and red lights to indicate the port side).

One of skill in the art will recognize that it may be desirable to transport a vessel 410 of the present invention in an emptied state, such as when a vessel 410 has been transported from a source to a delivery site and must thereafter be returned. In these circumstances, it is desirable to transport the vessel 410 in a manner requiring the least amount of storage space, weight and fuel costs. Accordingly, one embodiment of the present invention comprises the ability to at least partially deflate or extract a volume of air from a vessel 410 either during emptying operations or subsequent thereto. For example, vacuum powered means for emptying a vessel 410 may be attached to ports 414 to enable the extraction of an internal volume of fluid. Once all or most of an internal volume of fluid has been removed, the same or similar vacuum powered devices may be utilized to further extract a remaining internal volume of air from the vessel 410. It will be recognized that in such operations, measures may need to be taken to prevent a fully deflated vessel from sinking. Accordingly, the device 410 may be tethered to various objects, such as a towing vessel or fixed on-shore objects via attachment means 418 or other similar structures on the device 410. Deflating a vessel 410 as described offers the benefits of reducing the overall weight and volume of a device 410 to be transported, as well as reducing the potential for mold and other contaminants to grow inside of an otherwise damp and dark internal volume.

Once deflated, a vessel 410 may be further compacted by folding or rolling the vessel 410 onto a storage drum or wheel. Devices for rolling a large vessel 410 onto a storage drum are described in, for example, U.S. Pat. No. 6,550,410 to Reimers, which is hereby incorporated by reference in its entirety.

As an alternative to deflation, it is contemplated that vessels of the present invention may be alternatively filled with an air or gas of a sufficiently lower density than water to provide adequate buoyancy. In this manner, vessels 410 may then be towed in an "empty" state with minimal drag and associated fuel consumption needed to return a vessel 410 to another location for further filling or recycling. For example, helium and/or ambient air may be inserted into an emptied vessel 410 to provide sufficient buoyancy and minimal drag upon the vessel when towed without fluent cargo. In one embodiment, after most of the water has been drained from the towable vessel 410, the vessel is towed back to its point of origin with just a small amount of water remaining in the bag. Accordingly, the mostly-empty towable vessel 410 is towed behind a ship like a noodle.

Embodiments of the present invention may take the form or appearance of various objects which, for example, may hold commercial appeal or value. For example, at least a portion (e.g., a non-submerged portion) of towed vessels 410 of the present invention may comprise specific shapes or form specific characters for the purpose of displaying an image or a message. Images contemplated by the present invention include, but are not limited to, those with commercial appeal, such as trademarked or otherwise recognizable images or slogans which can be viewed by individuals including cruise passengers, airline passengers, and extraterrestrial image sensors (e.g., satellite photography).

It is further contemplated to provide vessels 410 of the present invention with the ability to selectively or temporarily display various images or messages. For example, portions of a vessel 410 which are inflated may be selectively inflated or positioned to display various images or text. In this manner, customizable messages may be displayed to various viewers. Alternatively, a portion of a vessel 410 of the present invention may include the ability to display written or marked images. For example, various inks, dyes, and similar materials may be placed upon a visible portion of the present invention. Such materials may be used to display, for example, the name of a company transporting contents, a third-party advertiser, or personal messages (e.g., a marriage proposal or a birthday wish).

In one embodiment, the present invention contemplates preserving the integrity and purity of fluids to be contained within a vessel 410 by incorporating various features and materials of the fluids original natural surroundings. For example, embodiments of the present invention may be utilized in transporting water from remote and pristine regions of the Earth. In such applications, various natural features of these regions, such as natural soils and clays, may be incorporated into in the towed vessel 410. U.S. Provisional Patent Application 61/251,912 to Szydlowski, which is hereby incorporated by reference in its entirety, discloses various benefits of naturally occurring soils when used for water filtration purposes.

Figure 33:
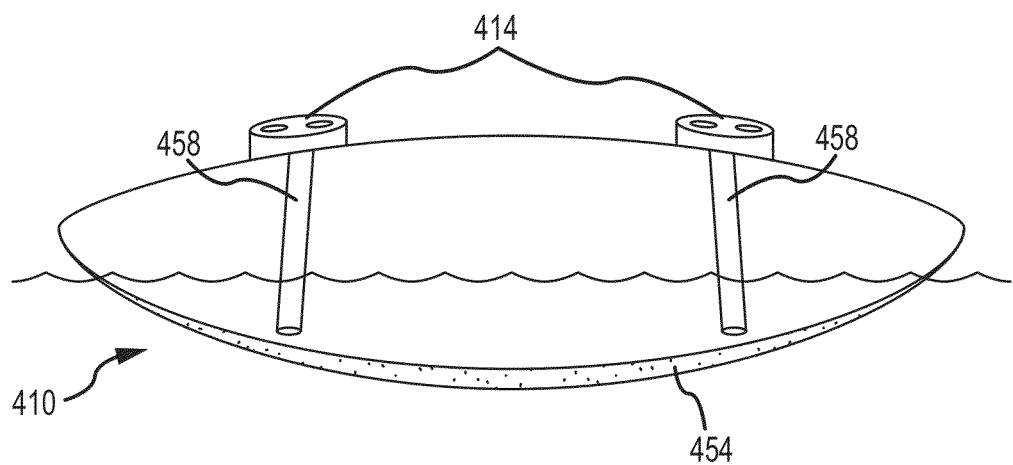
FIG. 33 is a cross-sectional side elevation view of a towed vessel suitable for transporting liquids or ice according to one embodiment.

In applications where water to be transported is desired for its natural characteristics, including purity, mineral content, and other attributes, it is often desirable to maintain those characteristics throughout filling, transporting, and emptying a vessel 410. Accordingly, the present invention contemplates various means to preserve purity of a transported fluid, particularly when polyurethane, polyethylene, XR-5 vinyl plasticizer, woven cloth, and other materials are employed as the structure of a vessel 410. As shown in FIG. 33, natural sediment 454 may be deposited within a towed vessel 410 which may act to isolate vessel contents from an inner surface of the vessel 410 as well as provide for filtration of the vessel contents upon entrance or exit from the vessel 410. Natural sediment 454 may be comprised of a variety of known soils, preferably those indigenous to the source of the water or fluid to be transported. For example, native clay minerals may be disposed within a vessel 410 to serve this function. Those of skill in the art will recognize the benefits offered by clay, including, but not limited to, its ability to isolate fluids from a vessel's inner surface and its effectiveness in filtration.

In one embodiment, the vessel 410 may comprise a coating on the top of the bag that is UV resistant to protect the integrity of the vessel's 410 material and vessel's contents. For example, Tedlar may be used on the top of the vessel 410.

In addition to acting as an isolating barrier between fluid to be transported and at least a portion of vessel's inner surface, the sediment 454 may also be useful in filtering fluids contained within the vessel 410. For example, where emptying of the vessel 410 is accomplish by connecting vacuum powered means to ports 414, sediment 454 may be allowed to be drawn toward the ports 414. In one embodiment, this may be accomplished through the use of one or more flexible tubes or conduits 458. Upon reaching the ports 414, the sediment 454 may be allowed to be trapped by any number of known filter devices. Such filter devices may include, for example, various mesh screens which may trap sediment particles and create a sedimentary filtration mechanism at an outlet 414 of the vessel 410.

In addition to or in lieu of depositing a layer of sediment 454 within a vessel 410, the interior surface area of a vessel 410 may be coated with a substance known to preserve the integrity and purity of fluid to be transported. Various coating methods and substances are known and described in, for example, U.S. Pat. No. 6,808,808 to Freeman et al., which is hereby incorporated by reference in its entirety. One embodiment of the vessel 410 includes a surface generally known as Sharklet™, which inhibits bacterial survival, growth, transfer and migration through pattern alone. Specific patents and publications describing the Sharklet surface technology are listed above.

Figure 34:
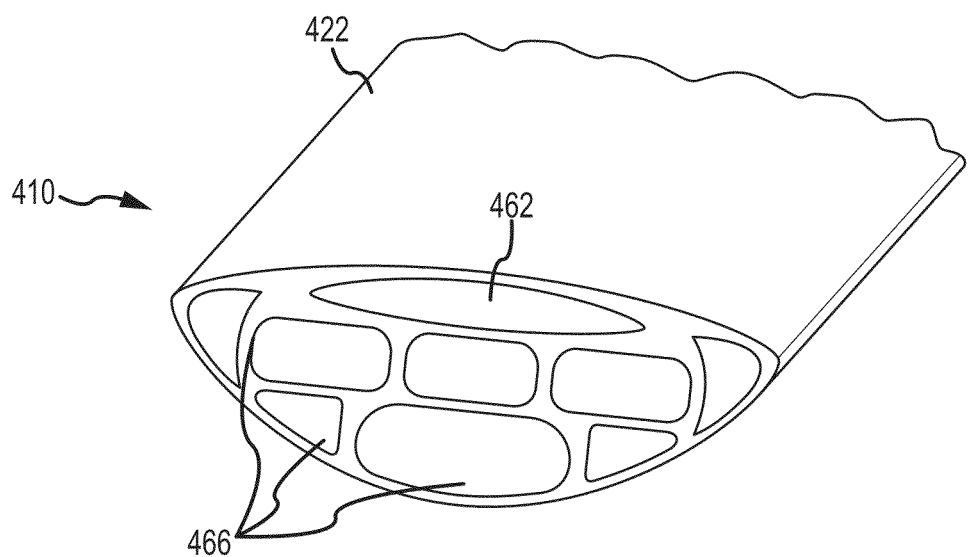
FIG. 34 is a cross-sectional perspective view of a towed vessel suitable for transporting liquids or ice according to one embodiment.

FIG. 34 is a cross-sectional perspective view depicting one embodiment where a towed vessel 410 is comprised of various different internal compartments. Embodiments of the present invention may include, for example, a bladder 462 which may be used to provide buoyancy for the vessel 410 as well as assist in maintaining the vessel 410 in a substantially upright position. In addition to a bladder 462, embodiments of the present invention may further comprise various compartments 466 within a larger vessel body 422. Various sizes and shapes of additional compartments 466 may be useful, for example, where a variety of different fluids are to be transported and comingling of these fluids is undesirable. Embodiments of the present invention comprising multiple internal compartments 466 allow for the simultaneous transport of, for example, fresh water, juice, wine, and a variety of other fluids. To allow access to various different compartments 466, embodiments of the present invention provide for a variety of ports 414 which allow for exclusive access to specific compartments 466. For example, each compartment 466 may have its own port 414. Ports 414 may be connected to compartments 466 through previously described flexible tubes or conduits. Embodiments of the present invention further contemplate marking systems to identify which ports 414 are associated with which compartments 466. For example, where cross-contamination of ports 414, associated tubes or conduits 458, and compartments 466 is undesired (i.e., where one or more port 414, conduit 458, and compartment 466 should be used only for a single type of fluent cargo), marking means such as text and color indicators are provided on a portion of the port 414 or vessel structure 422 to indicate to a user which materials should or should not be associated with a port 414. Those of skill in the art will recognize that the present invention is not limited to any number, sizes, or types of internal compartments 466. Indeed, the present invention contemplates the use of a single internal volume within a towed vessel as well as numerous compartments 466.

In one embodiment of the present invention, a towed vessel 410 further comprises mooring devices or means for attaching to mooring devices. For example, a towed vessel 410 includes fasteners, rigid members, and/or connecting devices to allow for a towed vessel 410 to be moored. Devices, and rigid members which may be connected to various portions of a mooring device include those disclosed in U.S. Patent Application Publication No. 2004/0157513 to Dyhrberg and U.S. Pat. No. 4,627,375 to Davis et al., which are hereby incorporated by reference in their entireties, and other similar known mooring devices. Including mooring devices as part of a towed vessel 410 or, alternatively, providing means to attach a towed vessel 410 to various mooring devices allows for the ability to fill or empty devices of the present invention in a number of locations or orientations, store the towable vessel 410 in a docked or off-shore location, and generally stabilize the structure 410 when transport is not desired.

Figure 35:
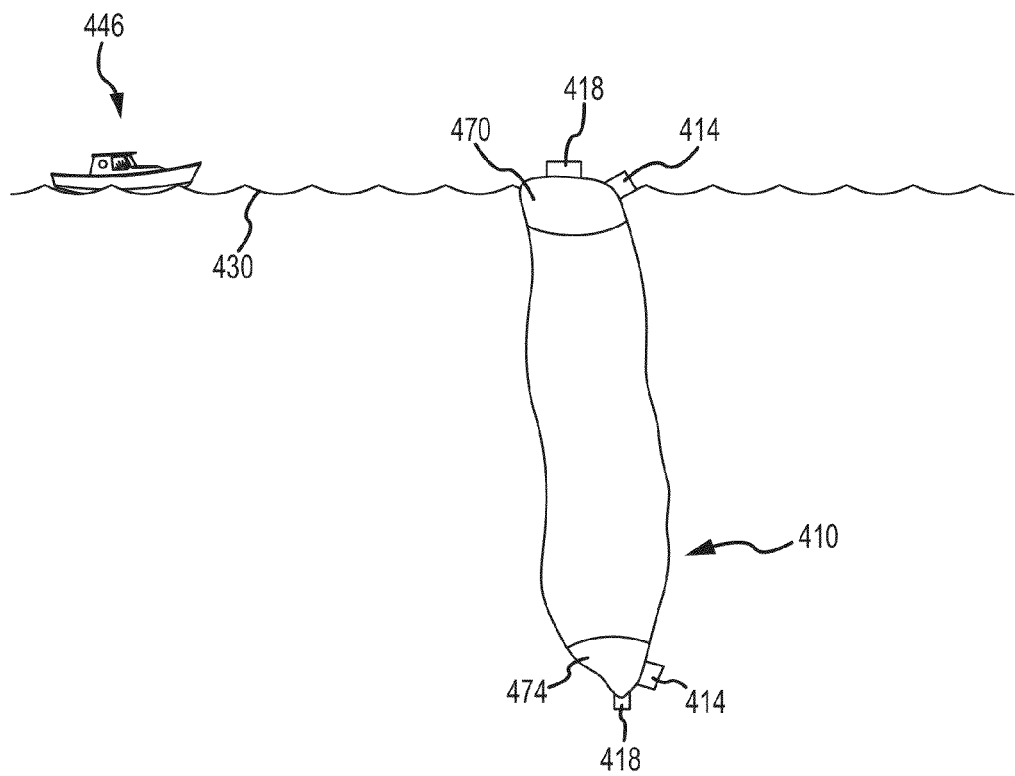
FIG. 35 is a side elevation view of a towed vessel suitable for transporting liquids or ice according to one embodiment.

Referring now to FIG. 35, one embodiment of the present invention is shown for storing a towed vessel 410 in a marine environment in a substantially vertical position with respect to a water line 430. Other vessels 446 may use means described herein to locate or avoid the towed vessel 410. In one embodiment, the present invention is capable of carrying up to 1,000,000 m$^3$ of bulk water. Accordingly, those of skill in the art will recognize that such an object, particularly when oriented in a generally horizontal position, will occupy a significant surface area. In one embodiment, the vessel 410 may be over 700 meters long. Therefore, one embodiment of the present invention contemplates devices and methods for storing a towed vessel 410 in a generally vertical position with respect to a water line 430. A first portion 470 of a towed device is inflated or similarly experiences an increase in buoyancy while an additional portion 474, preferably disposed at the distal longitudinal end, is filled with water or similarly experiences a decrease in buoyancy/density. In this manner, the device 410 may be allowed to float on-end and occupy substantially less volume than it would if docked or allowed to remain horizontal. In one embodiment, the contents and associated buoyancy of compartments 470, 474 are varied and/or controlled by one or more one-way or two-way valves 414. For example, compartment 474 may be filled with water via the control of valve 414. The volume of water taken in by valve 414 is then allowed to cool due to its position in a deeper portion of a body of water which is known to generally be colder than areas disposed closer to the surface 430. In one embodiment, valve 414 comprises a two-way valve capable of dispelling water from a compartment 474 and facilitating the repositioning of the device 410 to a surfaced position.

In an alternative embodiment, a towed vessel 410 may be stored in a generally vertical position either when it is an emptied or full state. Such a device is capable of being attached to various fixed and/or floating objects (e.g., mooring devices, which includes buoys) via a reinforcing member 418, while a distal end of the device 410 is allowed to sink. In one embodiment, the distal end is allowed to sink by decreasing the buoyancy of a portion 474 of the vessel 410 through the addition of water, sand, ballast, etc., which is further capable of being expelled from the device via two-way valve 414 in order to restore the vessel 410 to a generally horizontal position.

Figure 36:
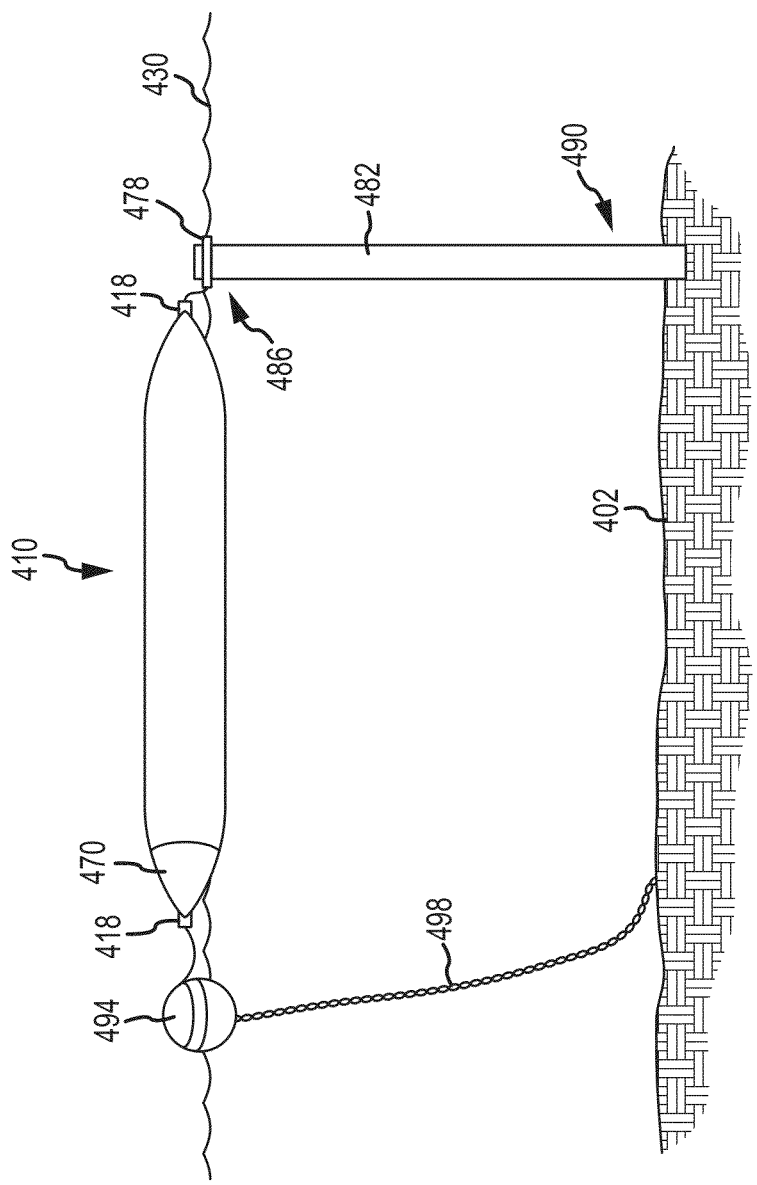
FIG. 36 is a side elevation view of the present invention according to one embodiment.
Figure 37:
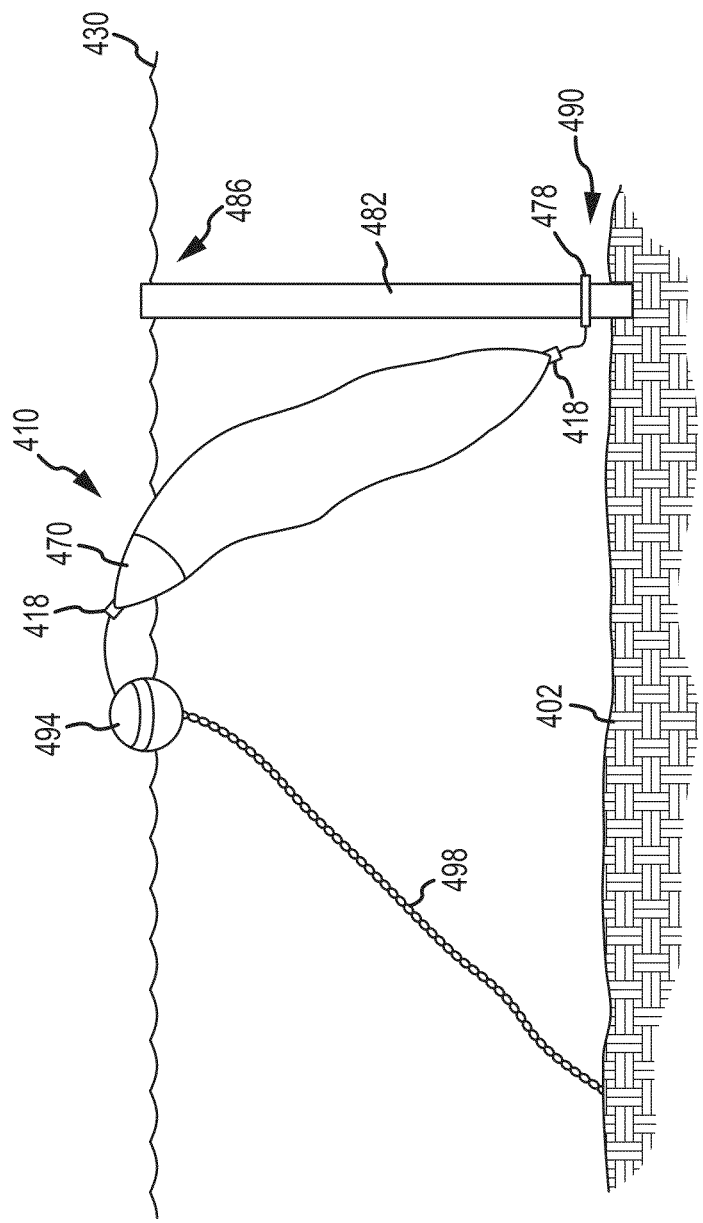
FIG. 37 is a side elevation view of the present invention according to one embodiment.

Referring now to FIGS. 36-37, a towed vessel 410 and associated storage means are depicted. When a vessel 410 is to be stored, a reinforcing member 418 may be attached to a securing device, such as a mooring buoy 494 and associated anchor line/chain 498 which may be securely fixed to a floor 402 of a marine environment. Additionally, a second end may be secured to a translatable device 478 positioned on a fixed member 482. Thus, in one embodiment, the vessel 410 resides at the surface 430 of a body of water in a substantially immobile position when the translatable device 478 is located at or near a surface position 486. Towed vessels 410 of the present invention may be selectively positioned in a substantially vertical position by translating the translatable device 478 along a vertical length of the fixed member 482 so that the translatable device 478 and second end of the vessel 410 is disposed in a submerged position 490. One of skill in the art will recognize that mooring devices 494, 498 of embodiments of the present invention, although generally fixed, may be free to translate within a given radius. Thus, when one end of a vessel 410 is submerged, an end attached to a mooring buoy 494 may reposition itself to a location proximal to the fixed member 482, thus allowing the vessel 410 to reside in a substantially vertical position for storage. The vertical positioning of vessels 410 of the present invention may be facilitated by the inclusion of a portion 470 of the vessel 410 which retains a sufficient amount of buoyancy so as to prevent the entire vessel 410 from sinking. Alternatively, mooring buoys 494 of the present invention may comprise sufficient buoyancy to support a load applied by a partially submerged vessel 410.

Vertical positioning devices 482 of the present invention may comprise various known devices useful in the linear translation of objects. For example, worm gears adapted for use in translating associated nuts, pulley systems, hydraulic jack or elevator devices, rail actuators, and various other known devices useful for translating a device 478 between a raised 486 and lowered 490 position may be incorporated into embodiments of the present invention.

Figure 38:
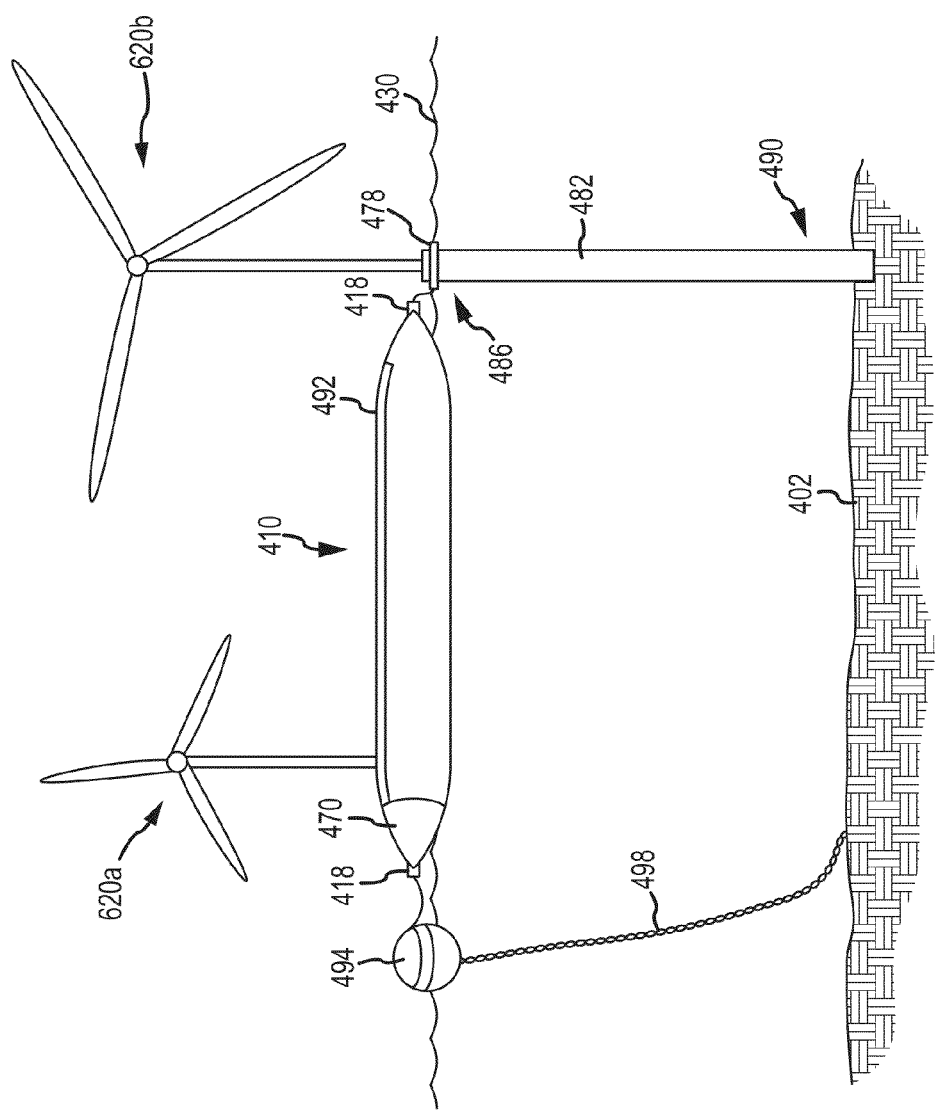
FIG. 38 is a side elevation view of an embodiment of a towed vessel in an anchored position.

FIG. 38 shows a towed vessel 410 with solar cells 492 on a top surface of the vessel 410. The solar cells 492 may be photovoltaic solar cells in one embodiment and allow the vessel 410 to collect solar energy for various functions, as described above. Thus, the vessel 410 may have photovoltaic cells 492 on a surface to convert solar energy to electrical power that may be utilized on-board a tug 446 or towing vessel. The towable vessel 410 may also comprise a windmill 620*a* to collect wind energy for uses described above. The vessel 410 may only have solar cells 492 in one embodiment, may only have a windmill 620*a* in another embodiment, or may have both solar cells 492 and one or more windmills 620*a* in a further embodiment. In some embodiments, the vertical positioning device 482 may comprise a windmill 620*b*. Any windmill 620 known in the art may be used.

Figure 39:
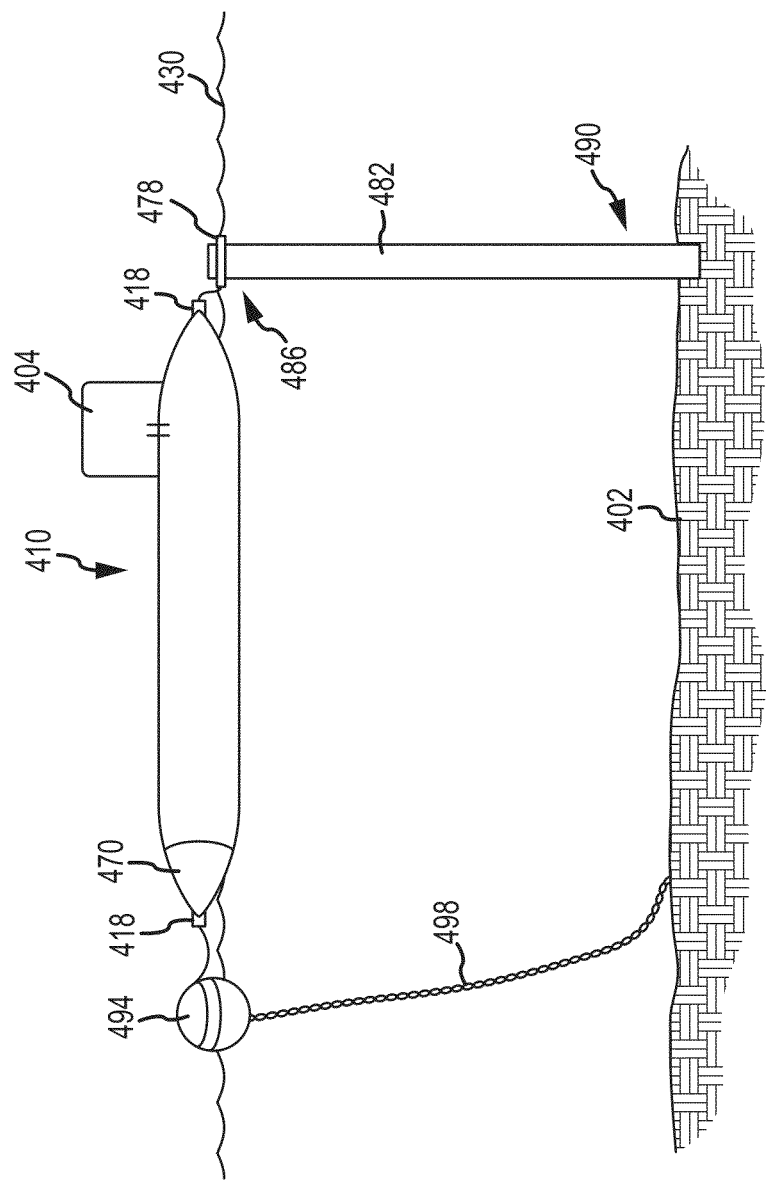
FIG. 39 is a side elevation view of another embodiment of a towed vessel in an anchored position.

FIG. 39 shows a towed vessel 410 with a purification/filtration system 404. The purification system 404 may treat the liquid or water in the vessel 410 by circulating the water or liquid through a port interconnecting the contents of the vessel 410 and the purification system 404. The purification system 404 may operate continuously or on an as-needed basis, which may be determined by sensors within the vessel 410. In an alternate embodiment, the purification system 404 may only treat the liquid as it is exiting the vessel 410, i.e., as a boat or vessel 446 takes water from the towable vessel 410. The purification system 404 may be powered by solar energy, wind energy, or any other means described herein or known in the art. Thus, in one embodiment, the vessel 410 may comprise solar cells 492 or a windmill 620 to power the purification system 404.

Figure 40:
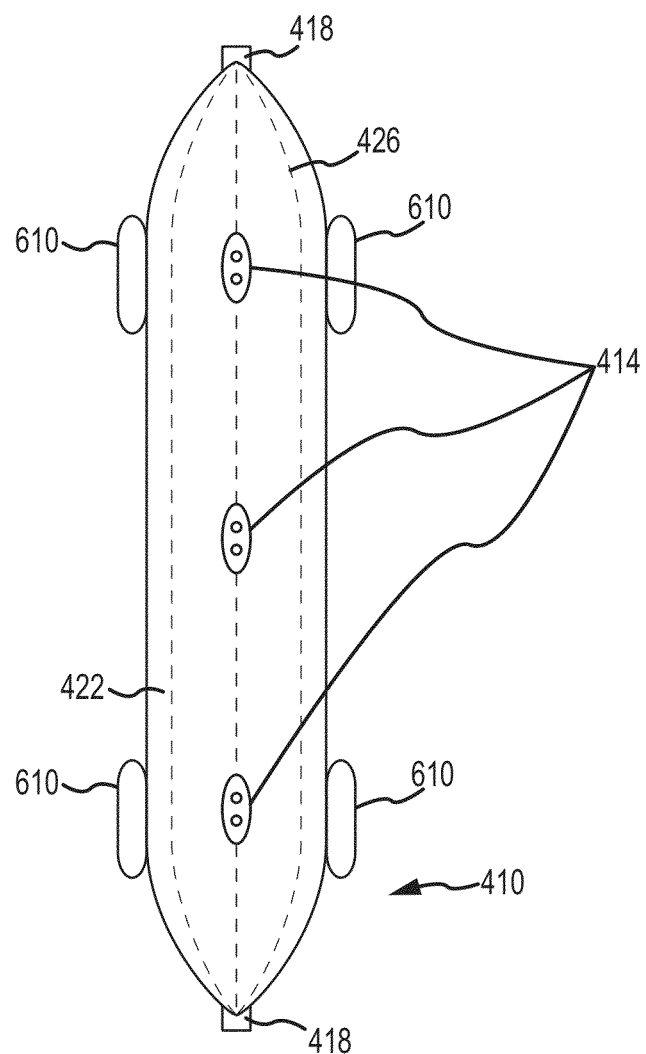
FIG. 40 is a top plan view of an embodiment of a towed vessel with drones.

FIG. 40 shows a towed vessel 410 with drones 610 secured thereto. The drones 610 may comprise an engine and propulsion mechanisms to maneuver the vessel 410. The drones 610 may also have sensors, a positioning system, and a control system that is remotely operated. Any known water drones may be used in embodiments of the present invention.

In one embodiment of the present invention, water is transported in a large water bag. Such bags are made of a suitable material, such as plastic, rubber, nylon, combinations thereof, and the like, and can vary in size depending on the amount of water being transported. Such bags have the advantage of not altering the quantity or characteristic of the water contained therein. To transfer water using such devices, the bags are filled with the water to be transported, sealed and then transferred to the final destination. Any method of moving such bags can be employed. A particularly useful method is to tow such bags through the ocean, rivers, or lakes using ships, barges, tankers, boats, and the like. In one embodiment, unmanned GPS-guided boats tow the bags. Other space-based and terrestrial guidance systems may also be used to guide vessels towing such bags. In some embodiments, the vessels operate autonomously. In still other embodiments, the vessels operate autonomously but can receive updated commands and instructions from remotely located operators. Such transport mechanisms would reduce the cost associated with a crew. FIG. 15 is a side view of a towing and attachment arrangement for a transporter embodiment.

Figure 41:
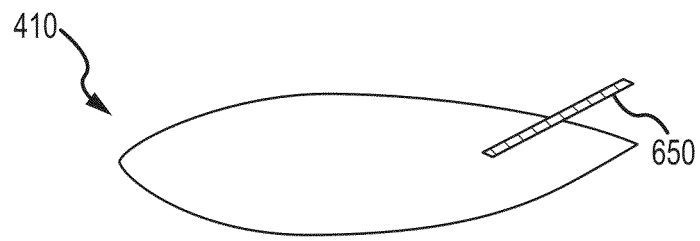
FIG. 41 is a cross-sectional side elevation view of a towed vessel suitable for transporting liquids and/or ice according to one embodiment.

FIG. 41 shows a towable vessel 410 with a straw-like draining mechanism 650. The straw 650 allows liquid to be removed from the bag. The vessel 410 may also comprise pumps and vacuums to suck liquid out of the bag more quickly. In another embodiment, a plurality of straws 650 may be used to evacuate the liquid quicker.

Figure 42:
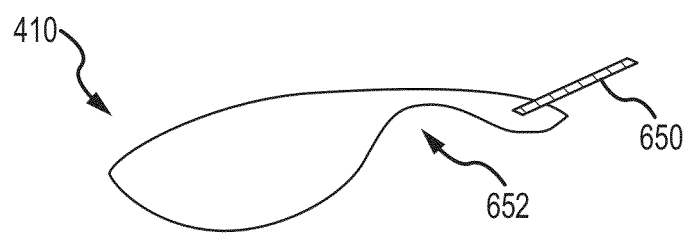
FIG. 42 is a cross-sectional side elevation view of a towed vessel suitable for transporting liquids and/or ice according to one embodiment.

FIG. 42 shows the vessel 410 with a fold 652 and a straw-like draining mechanism 650. The vessel 410 may purposefully be folded to increase the pressure of the contents within the vessel 410 such that the liquid is evacuated quicker than without the fold 652. In other embodiments, the straw 650 may be a mechanism to release liquid in the vessel 410 and thus reduce the internal pressure of the vessel 410 if the vessel should get a fold 652. Air inlets may also be included in the vessel 410 to increase the speed of the liquid evacuation.

Figure 43:
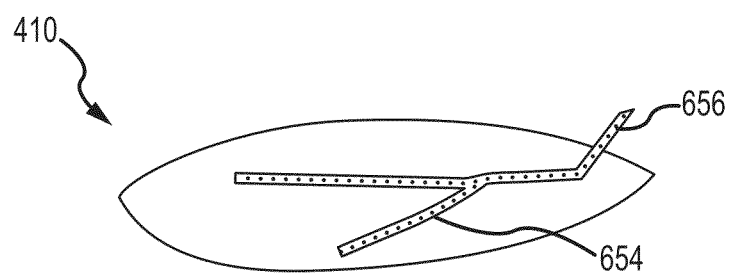
FIG. 43 is a cross-sectional side elevation view of a towed vessel suitable for transporting liquids and/or ice according to one embodiment.

FIG. 43 shows a vessel 410 with a French drain 654. The French drain 654 may comprise more than one draining member along the interior of the vessel 410. The French drain 654 also has an outlet 656 to allow the liquid to exit the vessel 410.

Figure 44:
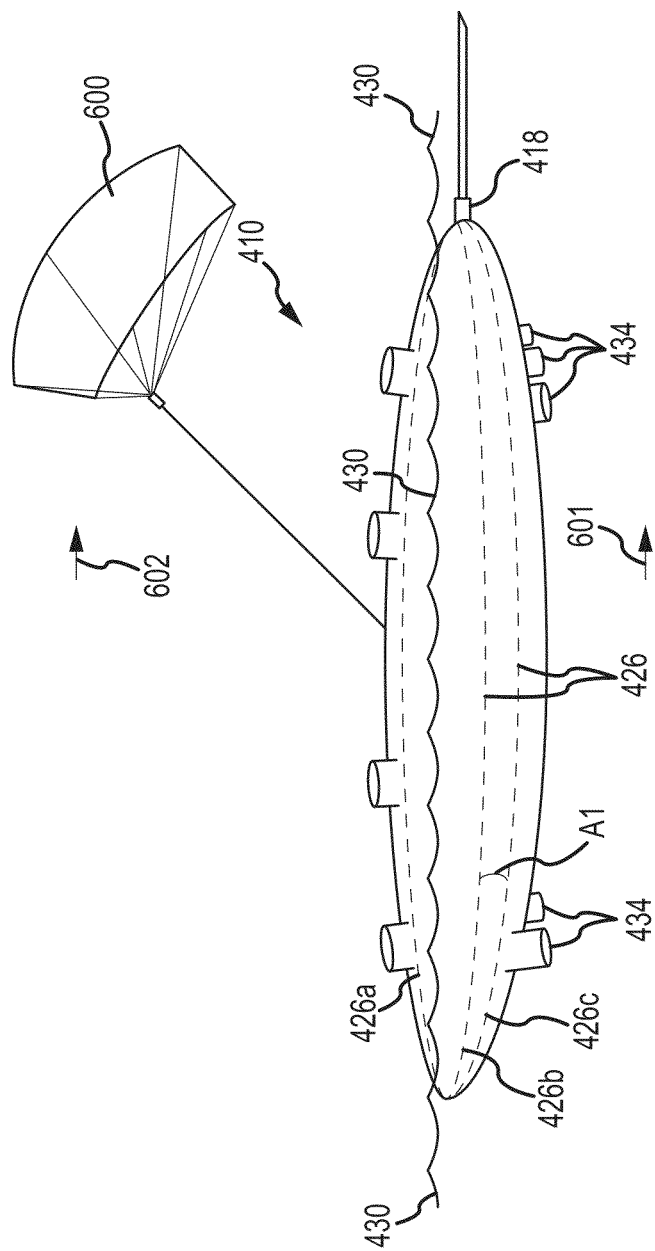
FIG. 44 is a side perspective view of a towed vessel suitable for transporting liquids and/or ice according to one embodiment.

FIG. 44 shows a vessel 410 being towed. An arrow 601 shows the direction of travel of the vessel 410. The vessel 410 may comprise a sail 600 that uses wind, shown by arrow 602, to further assist in the towing of the bag. The sail 600 may function similar to a sail on a sail boat and catch the wind 602 to pull the vessel 410.

Figure 45:
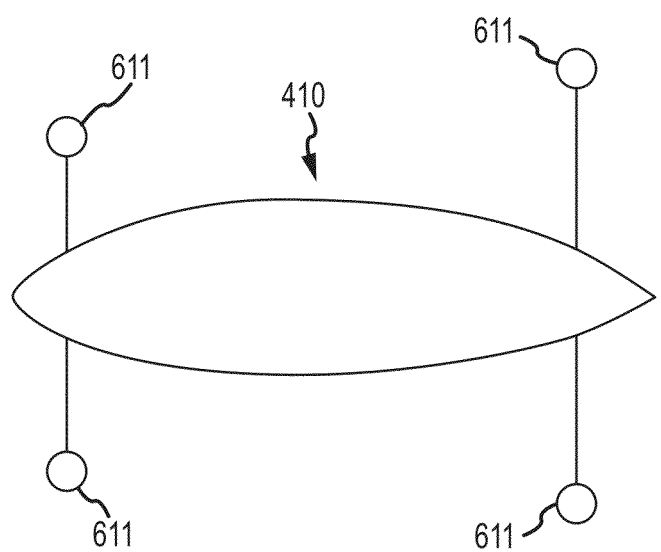
FIG. 45 is a top plan view of a towed vessel suitable for transporting liquids and/or ice in a stationary and secured position according to one embodiment.

FIG. 45 shows a towable vessel 410 filled with a liquid and secured by 4 ocean buoys 611. The 4 ocean buoys 611 keep the vessel 410 in the same location and do not allow the vessel 410 to rotate onto its side.

Figure 46:
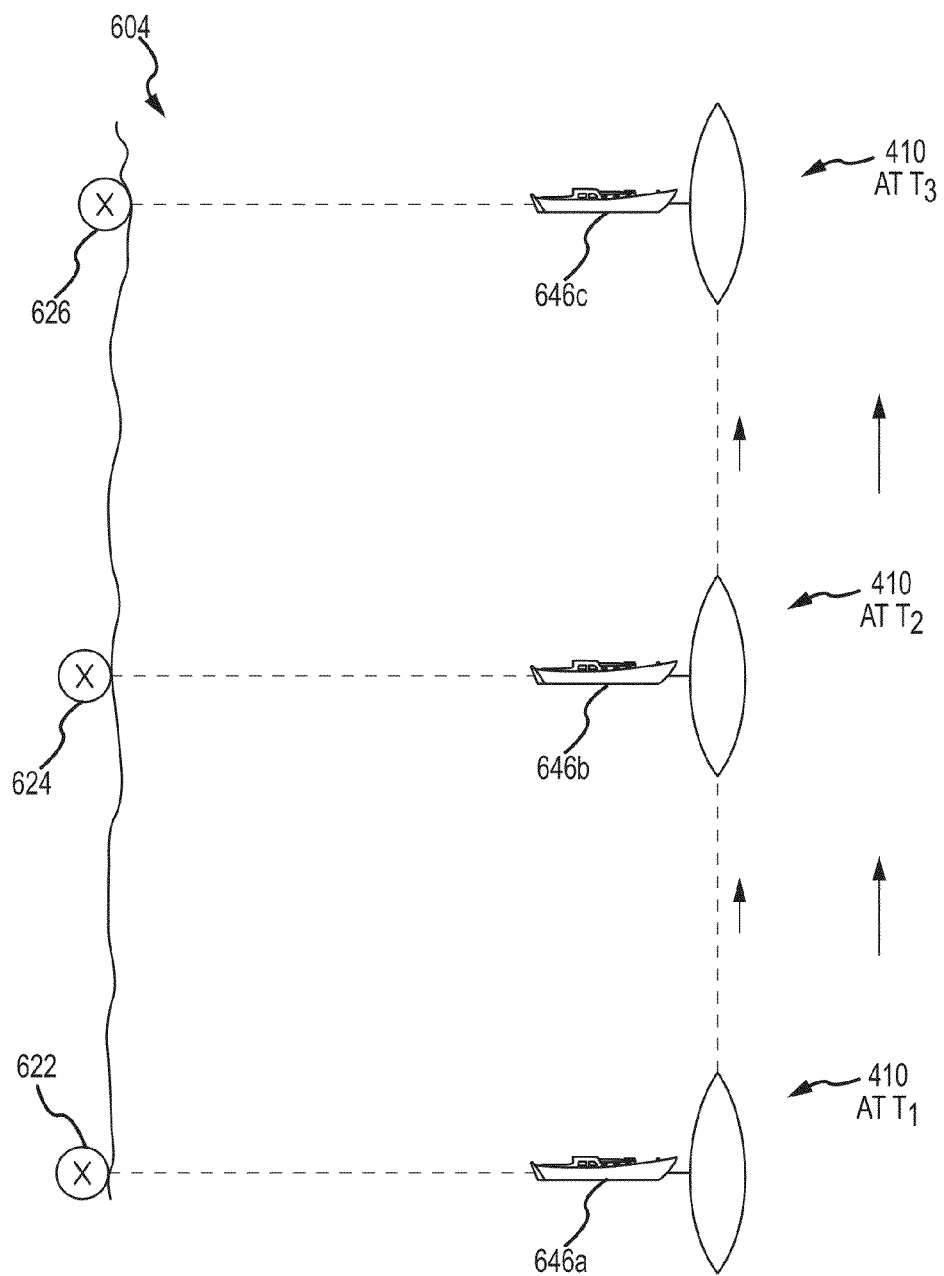
FIG. 46 shows a moving vessel transporting liquids and/or ice according to one embodiment.

FIG. 46 shows one embodiment of a water transport system 604. In the system 604 shown, three cities or ports 622, 624, 626 need fresh water. The towable vessel (VLB) 410 comprising fresh water travels along a coast line. At time T1 the VLB 410 is proximate to a first city 622. A first boat or other vessel 646*a* travels from the first city 622 to the VLB 410. At time T1 the first boat 646*a* gets fresh water from the VLB 410 and then returns to the first city 622. The entire time the VLB 410 is moving at approximately 3 knots (the direction of travel is shown by the arrows). At time T2 the VLB 410 is proximate to a second city 624. A second boat or other vessel 646*b* travels from the second city 624 to the VLB 410. At time T2 the second boat 646*b* gets fresh water from the VLB 410 and then returns to the second city 624 with the fresh water. At time T3 the VLB 410 is proximate to a third city 626. A third boat or other vessel 646*c* travels from the third city 626 to the VLB 410. At time T3 the third boat 646*c* gets fresh water from the VLB 410 and then returns to the third city 626 with the fresh water.

In some embodiments, solar-powered mooring stations for VLB water islands are provided. Similar to the example shown in FIG. 46, boats or vessels may come to a stationary VLB water island to get water. The VLB water island may have solar cells or windmills to collect solar and/or wind energy. Thus, the boats may use the VLB water islands as a sea anchor, a docking station, a charging station, and a fresh water source.

Figure 47A:
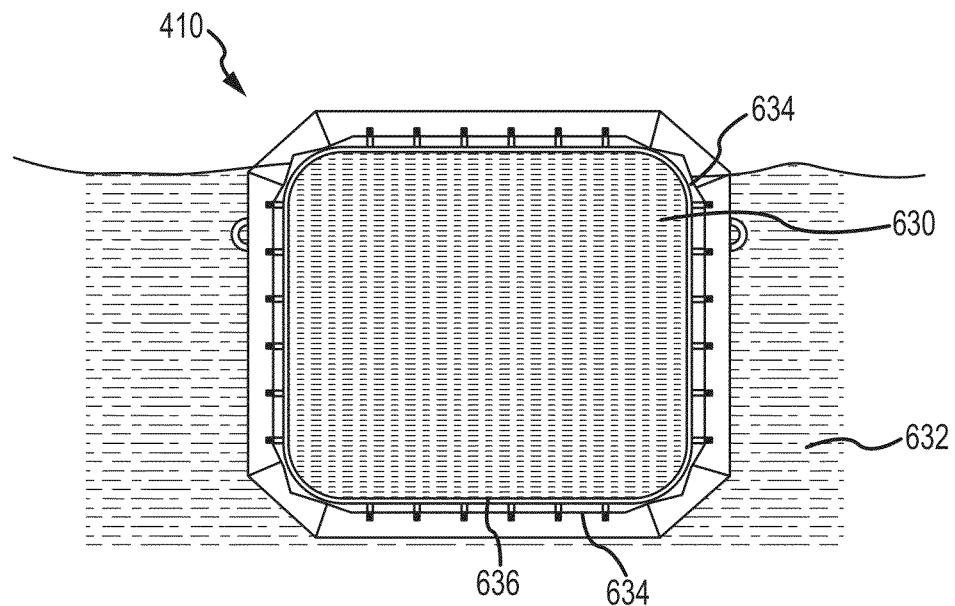
FIGS. 47A-B show a vessel comprising two liquids of different densities according to one embodiment.
Figure 47B:
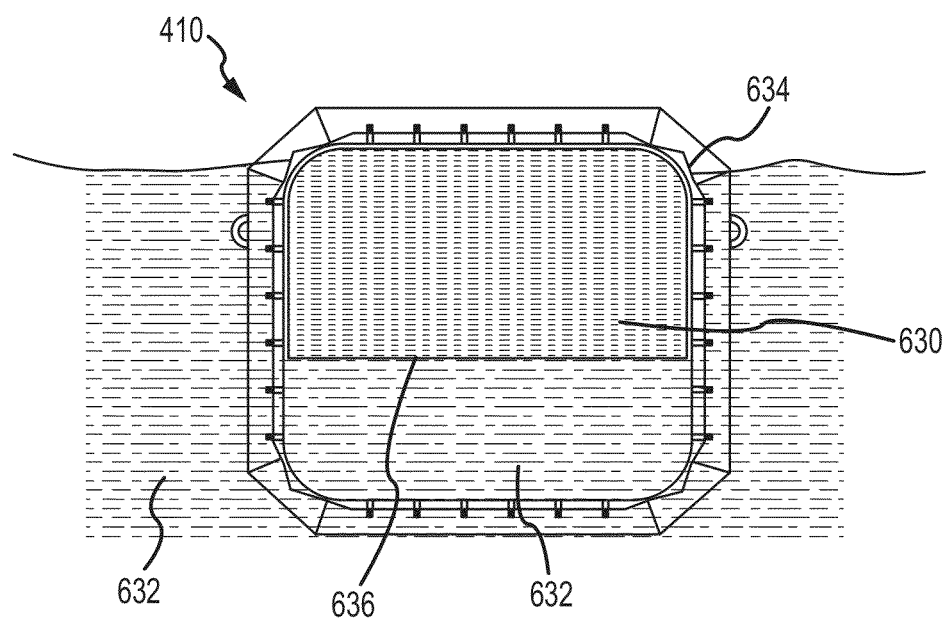

FIGS. 47A-B show a VLB 410 being filled with salt water 632 to push the fresh water 630 to the top of the bag because fresh water 630 is approximately 2.5% lighter (i.e., less dense) than salt water 632 and thus floats on salt water 632. Membranes 634, 636 within the VLB 410 may be used to keep the salt water 632 separated from the fresh water 630. Additionally, the salt water 632 may be fully contained within a bladder 636 within the VLB 410 such that the salt water 632 does not contaminate the VLB 410 for future use with fresh water 630. For example, various liners 636 available from Fab-Seal Industrial Liners, Inc. may be provided to accommodate water to be stored within a VLB 410 and isolate the clean, non-salt water from salt water, dirty water, or various materials, gases, debris, etc. Liners suitable for use in some embodiments of the present invention include, but are not limited to, P.V.C. flexible membrane liner materials. In various embodiments, liners or bags 634, 636 may also be made of similar materials to the shipping container bags or very large bags 410 towed by a ship.

In various embodiments, bags or liners for isolating water or liquids may be fabricated in any desired manner, including in a completely flattened conformation. For example, two sheets of fabric may be cut to the desired plan shape and joined at their adjacent edges by suitable means consistent with the material of construction. For example, heat welding or solvent welding may be used if certain polymeric materials have been employed as the substance coating the fabric. Sewing may be necessary in addition. It is possible that the overall cost of a bag may be reduced if the center section and the edges are fabricated separately, i.e., not the flattened conformation.

In one embodiment, internal surfaces or portions may be coated with various materials to prevent or minimize risk of cross-contamination. For example, various spray-coatings may be applied once a quantity of water is emptied from a portion or section of the VLB to create a virgin surface for the holding and contacting with water or similar fluid cargoes. By way of example, industrial water-proof coatings provided by the Procachem Corporation may be provided to coat, cover, or seal a surface that was exposed to or in contact with salt water, dirty water, or a different type of water so as to render the surface capable of accommodating water without significant risk of cross-contamination. In various embodiments, internal volumes of bladders or similar structures are coated with a layer of material, the layer of material comprising an appropriate thickness to substantially eliminate the risk of cross-contamination between a liquid or material to be stored and a liquid or material previously stored in the same tank. In various embodiments, the layer of material applied is not so thick as to substantially impact the overall internal volume of the container, tank, vessel, etc.

It will be recognized that various different liquids and gases may be contained and transported within embodiments of the present invention. Accordingly the present invention is not limited to the transport of water, wine, or human potable substances.

The foregoing discussion of the invention has been presented for purposes of illustration and description. Further the description is not intended to limit the invention to the form disclosed herein. Consequently, variations and modifications commensurate with the above teachings, within the skill or knowledge of the relevant art, are within the scope of the present invention. The embodiments described above are further intended to explain the best mode presently known of practicing the invention and to enable others skilled in the art to utilize the invention in other embodiments and with various modifications required by their particular application or use of the invention. It is intended that the appended claims be construed to include alternative embodiments to the extent permitted by the prior art.

What is claimed is:

1. A method for preparing water obtained from a glacial ice source, comprising:
    dividing a glacial ice source into at least two glacial ice segments;
    determining characteristics relating to the at least two segments of the glacial ice source, wherein the characteristics between the at least two segments are different;
    in response to determining characteristics, grouping the at least two segments;
    processing one of the at least two segments separately; and
    directing recovered water from the one of the at least two segments to a flexible liquid containment container, wherein characteristics of the water from the one of the at least two segments remains substantially the same, and wherein the characteristics of the one of the at least two segments relates to at least one of age, purity, density, chemical content, and physical properties of water.

2. The method of claim 1, wherein the processing step comprises transforming the water from a solid state to a liquid state.

3. The method of claim 1, further comprising packaging the one of the at least two processed segments separately.

4. The method of claim 3, wherein the packaging step includes partitioning the one of the at least two segments into two flexible liquid containment containers.

5. The method of claim 1, wherein the flexible liquid containment container is sized to fit in a shipping container such that the flexible liquid containment container substantially fills the shipping container.

6. The method of claim 5, further comprising conveying water within the flexible liquid containment container.

7. The method of claim 1, wherein the determining step comprises at least one of ice core sampling, carbon dating, and measuring pH.

8. The method of claim 1, wherein the determining step comprises analyzing gas trapped within the at least two segments.

9. The method of claim 1, wherein the ice source is a glacier adjacent a navigable waterway.

10. The method of claim 1, wherein the liquid containment container comprises one or more ports for intake and exhaust of the water.

11. A method for preparing water obtained from a glacial ice source, comprising:
    determining characteristics relating to at least two ice segments of the glacial ice source, wherein the characteristics between the at least two segments are different;
    in response to determining characteristics, grouping the at least two segments;
    transforming the ice from the at least two segments from a solid state to water in a liquid state;
    recovering water derived from the ice from the at least two segments separately; and
    directing water after said recovering step to a non-rigid, water-impermeable device with an elongate shape having a first end, a second end and having a generally streamlined shape in plan view.

12. The method of claim 11, wherein the characteristics of the at least two ice segments relate to least one of age, purity, density, chemical content, and physical structure of the ice.

13. The method of claim 11, wherein the determining step comprises analyzing gas trapped within the at least two ice segments.

14. The method of claim 11, further comprising storing water in the non-rigid water-impermeable device.

15. The method of claim 11, wherein said non-rigid, water-impermeable device is a towable bag with a total surface area of 60,000 square meters.

16. The method of claim 11, further comprising providing one or more photovoltaic arrays to collect solar energy on said non-rigid, water-impermeable device.

17. The method of claim 16, further comprising conveying said non-rigid, water-impermeable device to a predetermined destination through salt water, wherein said photovoltaic solar arrays are adapted to contact a non-submerged surface of said non-rigid, water-impermeable device during said conveying step.

* * * * *